US012618798B2

(12) United States Patent
Watanabe et al.

(10) Patent No.: US 12,618,798 B2
(45) Date of Patent: May 5, 2026

(54) GAS SENSOR ELEMENT AND GAS SENSOR

(71) Applicant: NGK INSULATORS, LTD., Nagoya (JP)

(72) Inventors: Yusuke Watanabe, Nagoya (JP); Daichi Ichikawa, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 350 days.

(21) Appl. No.: 18/353,938

(22) Filed: Jul. 18, 2023

(65) Prior Publication Data

US 2024/0027393 A1 Jan. 25, 2024

(30) Foreign Application Priority Data

Jul. 20, 2022 (JP) ................................. 2022-115399
Jun. 8, 2023 (JP) ................................. 2023-094953

(51) Int. Cl.
*G01N 27/407* (2006.01)
*G01N 33/00* (2006.01)

(52) U.S. Cl.
CPC ..... *G01N 27/4072* (2013.01); *G01N 27/4077* (2013.01); *G01N 27/4078* (2013.01); *G01N 33/0037* (2013.01); *G01N 33/0059* (2013.01)

(58) Field of Classification Search
CPC ........... G01N 27/4072; G01N 27/4077; G01N 27/4078; G01N 33/0037; G01N 33/0059
See application file for complete search history.

(56) References Cited

U.S. PATENT DOCUMENTS

| | | | | |
|---|---|---|---|---|
| 4,579,643 A | * | 4/1986 | Mase ................... | G01N 27/417 |
| | | | | 204/429 |
| 2008/0210575 A1 | * | 9/2008 | Nonogaki .......... | G01N 27/4071 |
| | | | | 204/429 |
| 2011/0083490 A1 | | 4/2011 | Murakami et al. | |
| 2017/0284958 A1 | * | 10/2017 | Watanabe .......... | G01N 27/4074 |

FOREIGN PATENT DOCUMENTS

JP 2011-102793 A 5/2011

* cited by examiner

*Primary Examiner* — Paul M. West
(74) *Attorney, Agent, or Firm* — MATTINGLY & MALUR, PC

(57) ABSTRACT
Provided is a gas sensor element or the like in which a diffusion mode of $NO_x$ reaching a measurement electrode is changed from molecular diffusion to a mode of diffusing while repeatedly colliding with a wall face of a sufficiently narrow flow path. In a gas sensor element according to one aspect of the present invention, a porous diffusion layer covering a measurement electrode has a porosity that is lower than the porosity of a leading end protection layer covering at least a face of an element substrate in which a gas inlet is open, and that is 5% or more and 25% or less.

19 Claims, 12 Drawing Sheets

GAS SENSOR ELEMENT AND GAS SENSOR

CROSS-REFERENCE TO RELATED APPLICATION

The present application claims priority from Japanese application JP 2022-115399, filed on Jul. 20, 2022, and JP 2023-094953, filed on Jun. 8, 2023, the contents of which are hereby incorporated by reference into this application.

TECHNICAL FIELD

The invention relates to a gas sensor element and a gas sensor.

BACKGROUND ART

Various attempts at applying predetermined diffusion resistance to a measurement target gas introduced into an internal space in a gas sensor element, which is used to measure the concentration of a specific gas component in the measurement target gas are conventionally known. For example, JP 2011-102793A discloses a gas sensor element that includes a diffusion control portion that applies predetermined diffusion resistance to the measurement target gas introduced into the internal space.

JP 2011-102793A is an example of related art.

SUMMARY OF THE INVENTION

The inventors found the following problem with the conventional gas sensor element that includes a diffusion control portion such as the aforementioned one. Specifically, the concentration of $H_2O$ in exhaust gases is higher in gasoline vehicles than in diesel vehicles. In addition, hydrogen engine vehicles are expected to be used under highly lean conditions for environmental reasons, and the concentration of $H_2O$ in exhaust gases is also expected to be high. $H_2O$ has a smaller molecular weight than $NO_x$ and $O_2$. The inventors found that the following problem will occur in such an environment with high $H_2O$ concentration.

FIG. 11 shows an example of molecular diffusion in which one molecule is diffused in response to collision with another molecule. The inventors conceived that the following event will occur in a region where molecular diffusion of such a type as that illustrated in FIG. 11 is dominant. That is, since diffusion of molecules proceeds as a result of one molecule colliding with another molecule in molecular diffusion, as illustrated in FIG. 11, the diffusion coefficient changes due to the other molecule with which one molecule collides, i.e. the diffusion coefficient changes depending on the gas composition of a measurement target gas. Thus, the presence of $H_2O$, which has a smaller molecular weight, in the measurement target gas allows $NO_x$ and $O_2$ molecules to diffuse easily between $H_2O$ molecules, and it is conceivable that the amount of $NO_x$ and $O_2$ gases reaching a measurement electrode for measuring the concentration of a specific gas component in the measurement target gas will increase. The inventors conceived that, consequently, $NO_x$ output may vary and the measurement electrode may be more susceptible to deterioration depending on the $H_2O$ concentration (e.g. as the $H_2O$ concentration increases). The inventors confirmed through experiments that $NO_x$ output is more likely to vary and the deterioration of the measurement electrode is accelerated at higher $H_2O$ concentration than at lower concentration.

FIG. 12 shows an example of Knudsen diffusion, which is a diffusion mode different from molecular diffusion. In Knudsen diffusion, diffusion of a certain molecule is promoted as a result of the molecule colliding with a porous wall (a wall face of a flow path), as illustrated in FIG. 12. Since the pore size in the wall face is determined during burning, the diffusion coefficient does not change even if the gas composition in the measurement target gas changes. The inventors then found the following method useful as a solution to the aforementioned problem that is considered to be caused by molecular diffusion of $NO_x$ under high $H_2O$ concentration. That is, the inventors found it useful to adopt a method of changing the diffusion mode of $NO_x$ that reaches the measurement electrode from molecular diffusion to a mode of diffusing while repeatedly colliding with a wall face of a sufficiently narrow channel, as in Knudsen diffusion illustrated in FIG. 12.

In one aspect, the present invention has been made in view of these circumstances, and an object of the invention is to provide a gas sensor element or the like in which the diffusion mode of $NO_x$ that reaches the measurement electrode is changed from molecular diffusion to a mode of diffusing while repeatedly colliding with a wall face of a sufficiently narrow flow path.

The present invention adopts the following configurations in order to solve the aforementioned problem.

A gas sensor element according to a first aspect includes: an element substrate having a surface in which a gas inlet is open, and including an internal space into which a measurement target gas is introduced from the gas inlet; a leading end protection layer covering at least a face of the element substrate in which the gas inlet is open; a measurement electrode provided in the internal space and containing at least either silica or alumina; and a porous diffusion layer covering the measurement electrode and having a porosity that is 5% or more and 25% or less and is lower than a porosity of the leading end protection layer. In the case where the porous diffusion layer includes a plurality of faces (layers) with different porosities, the average porosity of the porous diffusion layer may be 5% or more and 25% or less, and the average porosity of the porous diffusion layer may be lower than the porosity of the leading end protection layer.

In this configuration, the measurement electrode is covered by the porous diffusion layer having a porosity that is 5% or more and 25% or less and is lower than the porosity of the leading end protection layer. The porous diffusion layer covering the measurement electrode can change the diffusion mode around the measurement electrode to a mode of diffusing while repeatedly colliding with a wall face of a sufficiently narrow flow path, as in Knudsen diffusion. Thus, even if $H_2O$ gas is present in the measurement target gas, the gas sensor element can reduce the impact of the $H_2O$ gas on $NO_x$ gas (and $O_2$ gas) by means of the porous diffusion layer that covers the measurement electrode. Specifically, the gas sensor element can suppress fluctuations in $NO_x$ output and the degradation of the measurement electrode, which are considered to be caused by molecular diffusion of $NO_x$ under high $H_2O$ concentration, by means of the porous diffusion layer that covers the measurement electrode.

Here, if a porous diffusion layer having large diffusion resistance is provided around the measurement electrode, the porous diffusion layer may be clogged with poisonous substances or the like. The gas sensor element includes the leading end protection layer that covers at least the face of the element substrate in which the gas inlet is open. This allows the gas sensor element to trap poisonous substances or the like using the leading end protection layer, i.e. capture poisonous substances or the like using the leading end protection layer.

Particularly, in the gas sensor element, the porosity of the leading end protection layer is higher (larger) than the porosity of the porous diffusion layer that covers the measurement electrode. Making the porosity of the leading end protection layer higher than the porosity of the porous diffusion layer enables the gas sensor element to prevent situations where the leading end protection layer is clogged with poisonous substances or the like, resulting in a decrease in $NO_x$ output.

The measurement electrode of the gas sensor element contains at least either silica or alumina. Here, when $NO_x$ is measured at a high temperature (e.g. 700 to 800 degrees Celsius), the measurement electrode constantly repeats expansion and contraction. Even in such an environment, the gas sensor element can realize the following effects as a result of the measurement electrode containing at least either silica or alumina. That is, the gas sensor element can prevent cracks, splitting, or the like from occurring in the porous diffusion layer that covers the measurement electrode and also prevent the measurement electrode from peeling away from the element substrate, by suppressing the expansion and contraction of the measurement electrode.

A gas sensor element according to a second aspect may be the gas sensor element according to the first aspect wherein the porous diffusion layer has two faces in a thickness direction that are an internal face opposing the measurement electrode and an external face, and the internal face has a porosity higher than a porosity of the external face.

In this configuration, of the two faces of the porous diffusion layer in the thickness direction, the internal face (i.e. the face on the side closer to the measurement electrode) that opposes the measurement electrode has a porosity higher than the porosity of the external face (i.e. the face on the side farther from the measurement electrode).

Here, if $H_2O$ on the surface of the measurement electrode decomposes to generate $H_2$ immediately after the sensor is driven, $H_2$ around the measurement electrode may increase the light-off time that is required from when the gas sensor starts until when it enters a steady operation state.

In the gas sensor element, $H_2$ generated in the vicinity of the surface of the measurement electrode is quickly diffused, as a result of the porosity of the internal face opposing the measurement electrode, of the two faces of the porous diffusion layer in the thickness direction, being higher than the porosity of the external face. Thus, even if $H_2O$ on the surface of the measurement electrode decomposes to generate $H_2$, the gas sensor element can reduce the impact of $H_2$ and prevent an increase in the light-off time.

A gas sensor element according to a third aspect may be the gas sensor element according to the first or second aspect that further includes a diffusion control portion configured to apply predetermined diffusion resistance to the measurement target gas in the internal space, wherein the measurement electrode is disposed in an internal cavity that is demarcated by the diffusion control portion on an upstream side in a flow direction of the measurement target gas.

In this configuration, the gas sensor element includes the diffusion control portion, and the measurement electrode is disposed in the internal cavity that is demarcated by the diffusion control portion on the upstream side in the flow direction of the measurement target gas. With this configuration, the gas sensor element can further bring the diffusion mode of $NO_x$ that reaches the measurement electrode closer to a mode of diffusing while repeatedly colliding with a wall face of a sufficiently narrow flow path, as in Knudsen diffusion, than in the case of not including the diffusion control portion.

A gas sensor element according to a fourth aspect may be the gas sensor according to any one of the first to third aspects wherein the measurement electrode and the porous diffusion layer are not in contact with each other, and a distance between the measurement electrode and the porous diffusion layer is 0.15 mm or less.

In this configuration, the measurement electrode is not in contact with the porous diffusion layer, and the distance between the measurement electrode and the porous diffusion layer is 0.15 mm or less. If $H_2O$ on the surface of the measurement electrode decomposes to generate $H_2$ immediately after the sensor is driven, $H_2$ around the measurement electrode may increase the light-off time that is required from when the gas sensor starts until when it enters a steady operation state, as mentioned above. In the gas sensor element, $H_2$ generated in the vicinity of the surface of the measurement electrode is quickly diffused as a result of a space (gap) being provided between the measurement electrode and the porous diffusion layer. This enables the gas sensor element to reduce the impact of $H_2$ and avoid an increase in the light-off time, even if $H_2O$ on the surface of the measurement electrode decomposes to generate $H_2$.

Here, excessively increasing the distance between the measurement electrode and the porous diffusion layer will reduce the effect of changing the diffusion mode around the measurement electrode into a mode of diffusing with repeated colliding with a wall face of a sufficiently narrow flow path, as in Knudsen diffusion, that is achieved by the porous diffusion layer. In the gas sensor element, the distance between the measurement electrode and the porous diffusion layer is 0.15 mm or less. The inventors confirmed that setting the distance between the measurement electrode and the porous diffusion layer to 0.15 mm or less can make the diffusion mode around the measurement electrode favorable by means of the porous diffusion layer, as in the case where the measurement electrode and the porous diffusion layer are in contact with each other. That is, it was confirmed that the porous diffusion layer that is separated from the measurement electrode by a distance of 0.15 mm or less can make the diffusion mode around the measurement electrode a mode of diffusing while repeatedly colliding with a wall face of a sufficiently narrow flow path, as in Knudsen diffusion. Therefore, the gas sensor element can suppress fluctuations in $NO_x$ output and the degradation of the measurement electrode, which are considered to be caused by molecular diffusion of $NO_x$ under high $H_2O$ concentration, by means of the porous diffusion layer that is separated from the measurement electrode by a distance of 0.15 mm or less.

A gas sensor element according to a fifth aspect may be the gas sensor element according to any one of the first to fourth aspects wherein the porous diffusion layer has two faces in a thickness direction that are an internal face opposing the measurement electrode and an external face, and the internal face has a porosity that is 10% or more higher than a porosity of the external face.

In this configuration, of the two faces of the porous diffusion layer in the thickness direction, the internal face opposing the measurement electrode has a porosity that is at least 10% higher than the porosity of the external face. As mentioned above, the following effects can be achieved as a result of the porosity of the internal face opposing the measurement electrode, of the two faces of the porous diffusion layer in the thickness direction, being higher than the porosity of the external face. That is, making the porosity of the internal face higher than the porosity of the external face can quickly diffuse $H_2$ generated in the vicinity of the surface of the measurement electrode and prevent an increase in the light-off time. Further, the inventors confirmed that the light-off time is shorter when the porosity of the internal face of the porous diffusion layer is 10% or more higher than the porosity of the external face, than when the porosity of the internal face is less than 10% higher than the porosity of the external face. Hence, the gas sensor element can shorten the light-off time as a result of the porosity of the internal face opposing the measurement electrode, of the two faces of the porous diffusion layer in the thickness direction, being 10% or more higher than the porosity of the external face, compared to when the porosity of the internal face is less than 10% higher than the porosity of the external face.

A gas sensor element according to a sixth aspect may be the gas sensor element according to any one of the first to fifth aspects wherein a distance from an outermost face of the leading end protection layer to the gas inlet is 0.2 mm or more.

In the gas sensor element of this configuration, the distance from the outermost face of the leading end protection layer to the gas inlet is 0.2 mm or more. The gas sensor element can achieve the following effects as a result of the distance from the outermost face of the leading end protection layer to the gas inlet being sufficiently long (specifically, 0.2 mm or more), i.e. the thickness of the leading end protection layer being sufficiently large. That is, the gas sensor element can reliably capture poisonous substances or the like in the leading end protection layer and prevent clogging caused by poisonous substances or the like in the vicinity of the gas inlet and avoid a decrease in $NO_x$ sensitivity, even in a harsh environment with a large amount of poisonous substances or the like.

A gas sensor element according to a seventh aspect may be the gas sensor element according to any one of the first to sixth aspects wherein the leading end protection layer includes at least: an internal leading end protection layer in contact with the face of the element substrate in which the gas inlet is open; and an external leading end protection layer constituting an outermost face of the leading end protection layer. The internal leading end protection layer has a porosity larger than a porosity of the external leading end protection layer. The internal leading end protection layer has a thickness that is 30% or more and 90% or less of a thickness of the leading end protection layer.

In this configuration, the leading end protection layer includes at least the internal leading end protection layer that is in contact with the face of the element substrate in which the gas inlet is open, and the external leading end protection layer that constitutes the outermost face of the leading end protection layer. The porosity of the internal leading end protection layer is larger than the porosity of the external leading end protection layer, and the thickness of the internal leading end protection layer is 30% or more and 90% or less of the thickness of the leading end protection layer.

The gas sensor element can prevent clogging caused by poisonous substances or the like in the vicinity of the gas inlet and avoid a decrease in $NO_x$ sensitivity, as a result of the porosity of the internal leading end protection layer being larger than the porosity of the external leading end protection layer.

Particularly, the gas sensor element can achieve the following effects due to an increased thickness of the internal leading end protection layer that has a porosity larger than the external leading end protection layer, i.e. an increased proportion of the thickness of the internal leading end protection layer to the thickness of the leading end protection layer. That is, securing a sufficient thickness of the internal leading end protection layer having a large porosity makes it possible to prevent clogging caused by poisonous substances or the like in the vicinity of the gas inlet, particularly to reduce the likelihood of clogging in a layer close to the gas inlet (i.e. the internal leading end protection layer). Specifically, the internal leading end protection layer that is in contact with the gas inlet can be prevented from clogged with poisonous substances or the like, due to the proportion of the thickness of the internal leading end protection layer having a larger porosity to the thickness of the leading end protection layer being 30% to 90%.

A gas sensor according to one aspect of the invention may be configured to measure an amount of a specific gas component in the measurement target gas, using the gas sensor element according to each of the above aspects. This gas sensor changes the diffusion mode of $NO_x$ that reaches the measurement electrode from molecular diffusion to a mode of diffusing while repeatedly colliding with a wall face of a sufficiently narrow flow path. Thus, in this gas sensor, the porous diffusion layer covering the measurement electrode can suppress fluctuations in $NO_x$ output and deterioration of the measurement electrode, which are considered to be caused by molecular diffusion of $NO_x$ under high $H_2O$ concentration.

According to the present invention, it is possible to provide a gas sensor element or the like in which the diffusion mode of $NO_x$ that reaches the measurement electrode is changed from molecular diffusion to a mode of diffusing while repeatedly colliding with a wall face of a sufficiently narrow flow path.

EMBODIMENT OF THE INVENTION

Figure 1:
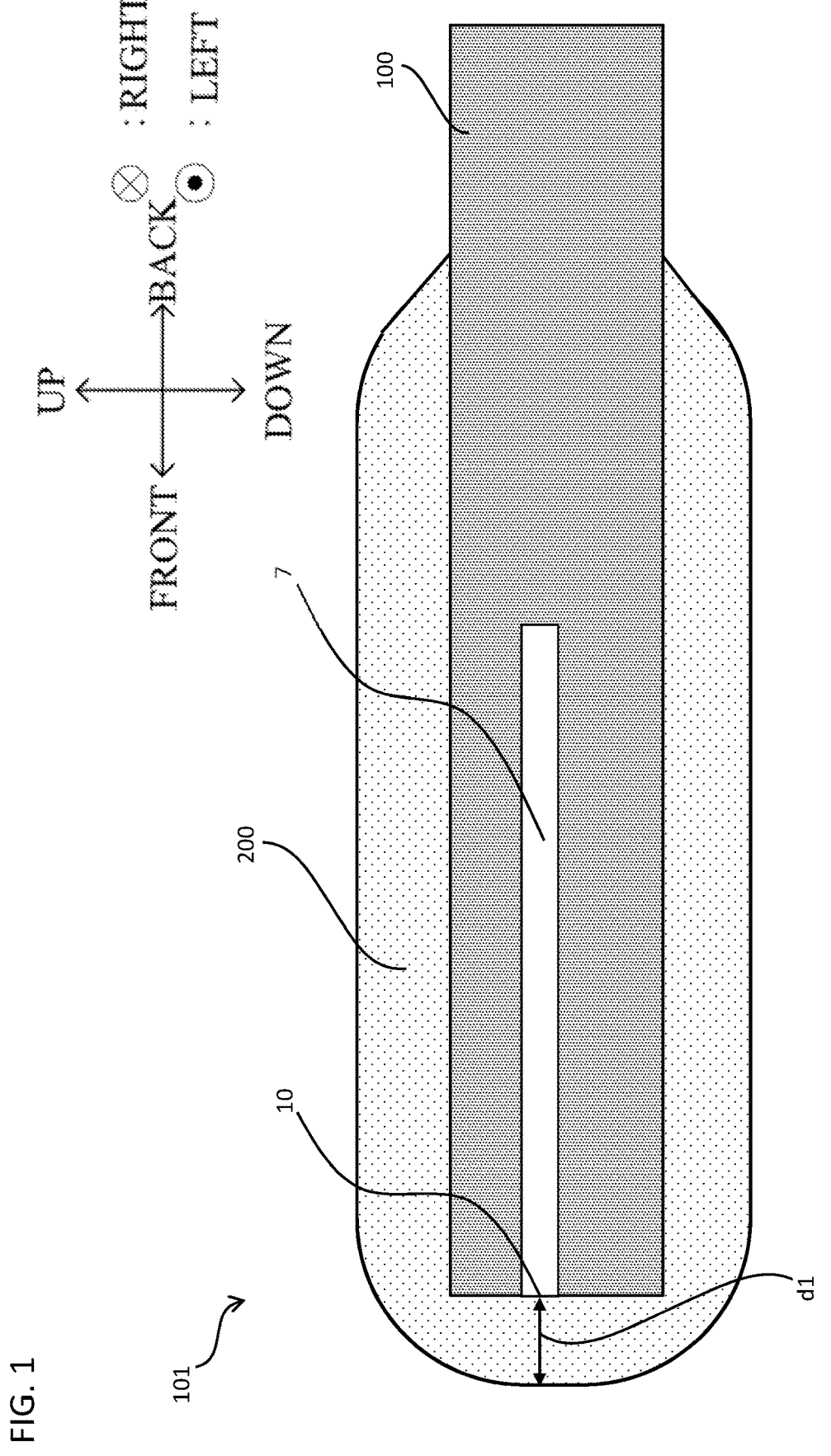
FIG. 1 is a cross-sectional schematic view that schematically shows an example of a configuration of a sensor element according to an embodiment.

An embodiment of one aspect of the present invention (hereinafter also referred to as "the present embodiment") will be described below with reference to the drawings. Note that the following embodiment is in all respects merely illustrative of the invention. It goes without saying that various modifications and variations can be made without departing from the scope of the invention. That is, specific configurations according to the embodiment may be adopted, as appropriate, to implement the invention.

The inventors confirmed that the higher the $H_2O$ concentration in a measurement target gas is, the more likely $NO_x$ output is to vary, and the quicker the measurement electrode degrades. For example, it was confirmed that $NO_x$ output is more likely to vary and the measurement electrode deteriorates more quickly in an environment with higher $H_2O$ concentration (under higher $H_2O$ concentration) where the $H_2O$ concentration in the measurement target gas is 20% or more (specifically, around 25%). One possible contributing factor to this problem, namely fluctuations in $NO_x$ output and the deterioration of the measurement electrode under high $H_2O$ concentration, is that the diffusion mode around a measurement electrode 44 is molecular diffusion. The inventors then confirmed that the aforementioned problem could be solved by changing the diffusion mode around the measurement electrode 44 from molecular diffusion to a mode of diffusing while repeatedly colliding with a wall face of a sufficiently narrow flow path, as in Knudsen diffusion.

In a gas sensor element 101 according to the present embodiment, a measurement electrode 44 is covered by a porous diffusion layer 91 having a porosity of 5% or more and 25% or less. Specifically, the measurement electrode 44 is covered by the porous diffusion layer 91 that has a porosity of 5% or more and 25% or less and is disposed at a position where a distance d2 to the measurement electrode 44 is 0.15 mm or less. The gas sensor element 101 changes the diffusion mode around the measurement electrode 44 by means of the porous diffusion layer 91 covering the measurement electrode 44. Specifically, the gas sensor element 101 changes the diffusion mode around the measurement electrode 44 from molecular diffusion to a mode of diffusing while repeatedly colliding with a wall face of a sufficiently narrow flow path, as in Knudsen diffusion, by means of the porous diffusion layer 91. This allows the gas sensor element 101 to reduce the impact of $H_2O$ gas on $NO_x$ gas (and $O_2$ gas) even if $H_2O$ gas is present in the measurement target gas, and to suppress fluctuations in $NO_x$ output and the deterioration of the measurement electrode 44, by means of the porous diffusion layer 91. That is, the gas sensor element 101 suppresses the deterioration of the measurement electrode 44 under high $H_2O$ concentration, e.g. when the measurement electrode 44 is driven for a long period of time under high $H_2O$ concentration. The gas sensor element 101 also suppresses fluctuations in $NO_x$ output under high $H_2O$ concentration, e.g. reduces $H_2O$ dependence of $NO_x$ output while the $NO_x$ gas is flowing, and thus increases the accuracy of $NO_x$ concentration measurements. Although the details will be described later, the porosity in the present embodiment is a value derived, for example, by applying a known image processing method (e.g. binarization) to an image (SEM image) observed and obtained using a scanning electron microscope (SEM). For example, the gas sensor element 101 is cut to obtain a face to be observed that is a cross-section of a certain layer, and the cut face is resin-filled and polished to make an observation sample. The SEM image of this layer is then obtained by capturing an image of the face to be obtained of the observation sample using a SEM photograph (secondary electron image with an accelerating voltage of 15 kV, a magnification of 1000×; however, if a magnification of 1000× is not appropriate, a magnification greater than 1000× and 5000× or less is used). Next, the obtained image is subjected to image analysis to determine a threshold value using a discriminant analysis method (Otsu binarization) based on the luminance distribution of luminance data of pixels in the image. Thereafter, each pixel in the image is binarized into an object part and a pore part based on the determined threshold value, and the area of the object part and the area of the pore part are calculated. Then, the ratio of the area of the pore part to the total area (total area of the object part and the pore part) is derived as the porosity [%] of the layer.

Further, in the gas sensor element 101 according to the present embodiment, a leading end protection layer 200 covers at least a face of an element substrate 100 in which a gas inlet 10 is open. The leading end protection layer 200 traps (captures) poisonous substances or the like that cause clogging in the porous diffusion layer 91 covering the measurement electrode 44. Specifically, the gas sensor element 101 traps poisonous substances or the like by means of the leading end protection layer 200 whose porosity is larger than that of the porous diffusion layer 91, thus preventing clogging around the measurement electrode 44, e.g. clogging in the porous diffusion layer 91. Hence, the gas sensor element 101 can prevent the porous diffusion layer 91 covering the measurement electrode 44 from being clogged with poisonous substances or the like, resulting in lower $NO_x$ output and lower measurement accuracy. The gas sensor element 101 according to the present embodiment will be described below in detail with reference to FIG. 1.

Example Configuration

FIG. 1 is a cross-sectional schematic view that schematically shows an example of a configuration of the gas sensor element 101 according to the present embodiment. As illustrated in FIG. 1, the gas sensor element 101 includes an element substrate 100 and a leading end protection layer 200. The element substrate 100 has a gas inlet 10 that is open in a surface thereof, and a measurement target gas is introduced from the gas inlet 10 to a measurement target gas flow portion 7, which is an internal space in the element substrate 100. In the example shown in FIG. 1, the gas inlet 10 is open in a front surface (on the leading end side) of the element substrate 100. In the following description, there are cases where the front surface (on the leading end side) of the element substrate 100 is referred to as a "leading end face" of the element substrate 100. In FIG. 1, the front (the leading end) side of the element substrate 100 corresponds to the left side of the sheet.

Leading End Protection Layer

The leading end protection layer 200 covers at least the face of the element substrate 100 (the leading end face of element substrate 100) in which the gas inlet 10 is open. In the example shown in FIG. 1, the leading end protection layer 200 covers the leading end face of the element substrate 100 and four side faces of the element substrate 100 that are continuous with the leading end face.

As will be described later in detail, providing the leading end protection layer 200 enables poisonous substances or the like that cause clogging in the porous diffusion layer 91 provided around the measurement electrode 44 to be trapped (captured) by the leading end protection layer 200. That is, the gas sensor element 101 can prevent the porous diffusion layer 91 from being clogged, as a result of the leading end protection layer 200 capturing poisonous substances or the like. Further, the porosity of the leading end protection layer 200 is higher than the porosity of the porous diffusion layer 91 that is provided around the measurement electrode 44. The gas sensor element 101 can thus prevent a situation where the leading end protection layer 200 itself is clogged with poisonous substances or the like, resulting in a decrease in $NO_x$ output of the gas sensor element 101.

The leading end protection layer 200 has a predetermined thickness; specifically, a distance d1 from the outermost face of the leading end protection layer 200 to the gas inlet 10 is 0.2 mm or more. The gas sensor element 101 can achieve the following effects as a result of the distance d1 from the outermost face of the leading end protection layer 200 to the gas inlet 10 being sufficiently long (specifically, 0.2 mm or more), i.e. the leading end protection layer 200 being sufficiently thick. That is, even in a harsh environment with a large amount of poisonous substances or the like, the leading end protection layer 200 can reliably trap (capture) the poisonous substances or the like can, thus preventing clogging caused by the poisonous substances or the like in the vicinity of the gas inlet 10 and avoiding a decrease in $NO_x$ sensitivity.

Element Substrate

Figure 2:
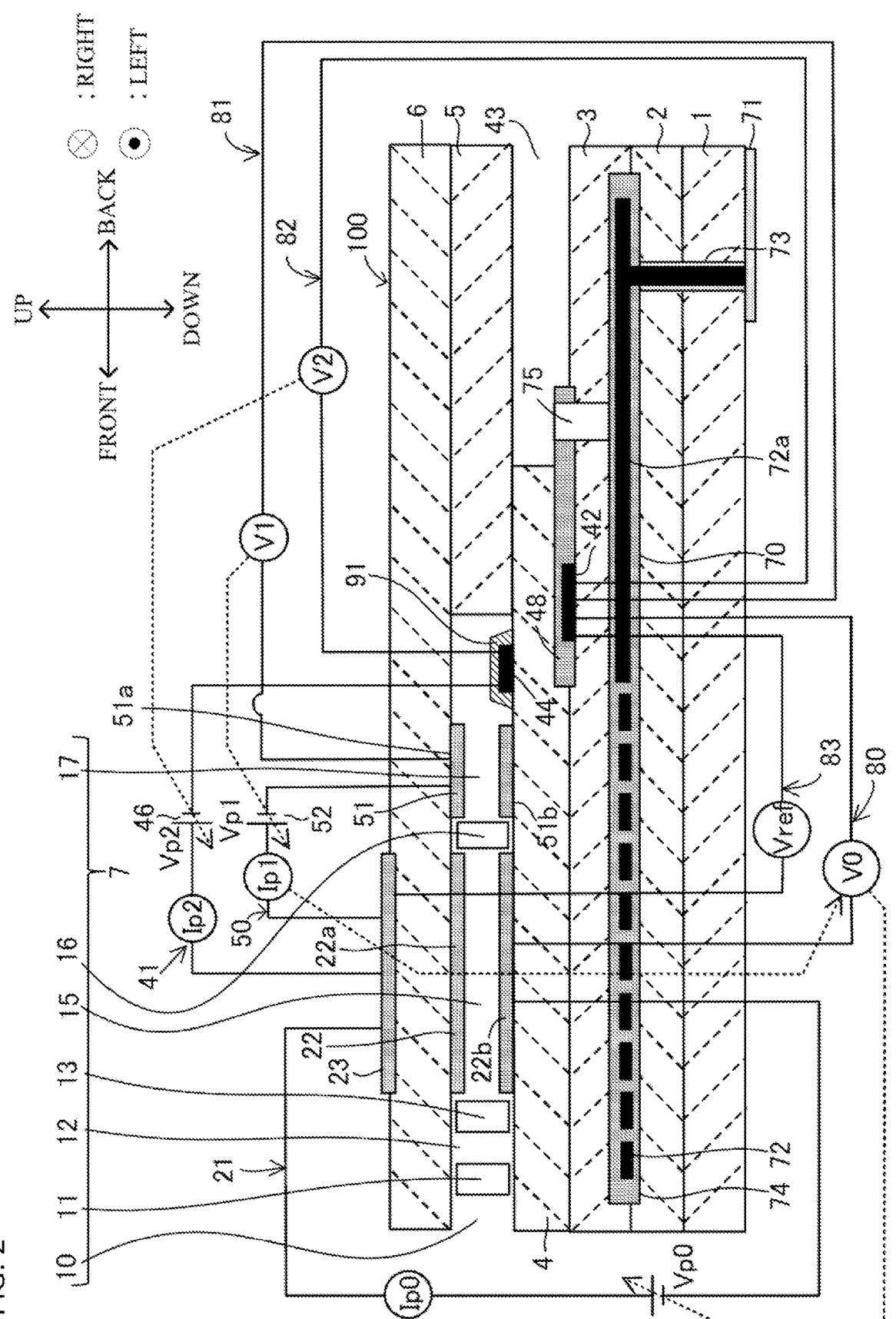
FIG. 2 shows a cross-sectional schematic view that shows an example of a configuration of an element substrate included in the sensor element in FIG. 1.

FIG. 2 is a cross-sectional schematic view that schematically shows an example of a configuration of the element substrate 100 of the gas sensor element 101. The element substrate 100 has a slender and elongated plate shape extending in a lengthwise direction (axial direction), for example, and also has a rectangular shape, for example. The element substrate 100 illustrated in FIG. 2 has a leading end portion and a rear end portion as end portions in the lengthwise direction. In the following description, the leading end portion corresponds to the left end portion (i.e. front end portion) in FIG. 2, and the rear end portion corresponds to the right end portion (i.e. rear end portion) in FIG. 2. Note that the shape of the element substrate 100 need not be limited to this example, and may be selected as appropriate, according to the mode of implementation. In the following description, the distal side of the sheet of FIG. 2 corresponds to the right side of the element substrate 100, and the proximal side of the sheet corresponds to the left side of the element substrate 100.

As illustrated in FIG. 2, the element substrate 100 includes a laminate formed by stacking a first substrate layer 1, a second substrate layer 2, a third substrate layer 3, a first solid electrolyte layer 4, a spacer layer 5, and a second solid electrolyte layer 6, in this order from the bottom. The layers 1 to 6 are each constituted by an oxygen-ion-conductive solid electrolyte layer made of zirconia ($ZrO_2$) or the like. The solid electrolyte that forms the layers 1 to 6 may be dense. Being dense means having a porosity of 5% or less.

For example, the element substrate 100 is produced by performing steps of predetermined processing, wiring pattern printing, and the like, on a ceramic green sheet corresponding to each layer, then stacking the processed layers, and firing and integrate the layers. As an example, the element substrate 100 is a laminate of a plurality of ceramic layers. In the present embodiment, an upper face of the second solid electrolyte layer 6 constitutes an upper face of the element substrate 100, a lower face of the first substrate layer 1 constitutes a lower face of the element substrate 100, and side faces of the layers 1 to 6 constitute side faces of the element substrate 100.

In the present embodiment, an internal space that receives the measurement target gas (i.e. into which the measurement target gas is introduced) from an external space is present at one leading end portion of the element substrate 100, between the lower face of the second solid electrolyte layer 6 and the upper face of the first solid electrolyte layer 4. The internal space according to the present embodiment includes the gas inlet 10, a first diffusion control portion 11, a buffer space 12, a second diffusion control portion 13, a first internal cavity 15, a third diffusion control portion 16, and a second internal cavity 17, which are adjacent to each other and connected in this order. In other words, the internal space according to the present embodiment has a two-cavity structure (the first internal cavity 15 and the second internal cavity 17).

In one example, the internal space is provided by hollowing out a portion of the spacer layer 5. An upper portion of the internal space is demarcated by the lower face of the second solid electrolyte layer 6. A lower portion of the internal space is demarcated by the upper face of the first solid electrolyte layer 4. Side portions of the internal space are demarcated by the side faces of the spacer layer 5.

The first diffusion control portion 11 is a member (portion) that applies predetermined diffusion resistance to the measurement target gas. In the example shown in FIG. 2, the first diffusion control portion 11 forms two laterally elongated slits (flow paths through which the measurement target gas flows) (i.e. have openings whose lengthwise direction is a direction perpendicular to the drawing). For example, the first diffusion control portion 11 is a bridging portion (a first bridging portion) that bridges the hollowed space in the spacer layer 5, and the space between the first diffusion control portion 11 and the layer 6 and the space between the first diffusion control portion 11 and the layer 4 serve as the slits, i.e. the flow paths CH through which the measurement target gas flows. Similarly, the second diffusion control portion 13 and the third diffusion control portion 16 are members that apply predetermined diffusion resistance to the measurement target gas. In the example shown in FIG. 2, the second diffusion control portion 13 and the third diffusion control portion 16 each form a hole (a flow path through which the measurement target gas flows) whose length in a direction perpendicular to the drawing is shorter than that of the first internal cavity 15 and the second internal cavity 17.

As illustrated in FIG. 2, the second diffusion control portion 13 and the third diffusion control portion 16 may both form two slits that are laterally elongated (i.e. have openings whose lengthwise direction is perpendicular to the drawing), similarly to the first diffusion control portion 11. For example, the second diffusion control portion 13 serves as a bridging portion (a second bridging portion) that bridges the hollowed space in the spacer layer 5, and the space between the second diffusion control portion 13 and the layer 6 and the space between the second diffusion control portion 13 and the layer 4 serve as the slits, i.e. the flow paths CH through which the measurement target gas flows. For example, the third diffusion control portion 16 serves as a bridging portion (a third bridging portion) that bridges the hollowed space in the spacer layer 5, and the space between the third diffusion control portion 16 and the layer 6 and the space between the third diffusion control portion 16 and the layer 4 serve as the slits, i.e. the flow paths through which the measurement target gas flows. The second diffusion control portion 13 and the third diffusion control portion 16 will be described later in more detail. The portion (internal space) from the gas inlet 10 to the second internal cavity 17 is referred to as a measurement target gas flow portion 7.

A reference gas introduction space 43 is located farther from the leading end side (i.e. the front side of the element substrate 100) than the measurement target gas flow portion 7, at a position between the upper face of the third substrate layer 3 and the lower face of the spacer layer 5 at which side portions are demarcated by the side faces of the first solid electrolyte layer 4. A reference gas, such as air, is introduced into the reference gas introduction space 43. Note that the configuration of the element substrate 100 need not be limited to this example. As another example, the first solid electrolyte layer 4 may extend to the rear end of the element substrate 100, and the reference gas introduction space 43 may be omitted. In this case, an air introduction layer 48 may extend to the rear end of the element substrate 100.

The air introduction layer 48 is provided at a portion of the upper face of the third substrate layer 3 adjacent to the reference gas introduction space 43. The air introduction layer 48 is made of porous alumina, and the reference gas is introduced thereinto via the reference gas introduction space 43. In addition, the air introduction layer 48 covers a reference electrode 42.

The reference electrode 42 is sandwiched between the upper face of the third substrate layer 3 and the first solid electrolyte layer 4, and is surrounded by the air introduction layer 48 that is connected to the reference gas introduction space 43. The reference electrode 42 is used to measure the oxygen concentration (oxygen partial pressure) within the first internal cavity 15 and the second internal cavity 17. The details will be described later.

The gas inlet 10 is a portion of the measurement target gas flow portion 7 that is open to the external space. The element substrate 100 takes the measurement target gas thereinto (i.e. the measurement target gas is introduced) from the external space through the gas inlet 10. The gas inlet 10 of the present embodiment is disposed in the leading end face (front face) of the element substrate 100, as illustrated in FIG. 2. In other words, the measurement target gas flow portion 7 has an opening in the leading end face of the element substrate 100. Note that it is not essential for the measurement target gas flow portion 7 to have an opening in the leading end face of the element substrate 100, i.e. to dispose the gas inlet 10 in the leading end face of the element substrate 100. The element substrate 100 need only be capable of taking the measurement target gas into the measurement target gas flow portion 7 from the external space, and the gas inlet 10 may alternatively be disposed in the right side face or the left side face of the element substrate 100, for example.

The first diffusion control portion 11 is a portion that applies predetermined diffusion resistance to the measurement target gas taken in from the gas inlet 10.

The buffer space 12 is a space for guiding the measurement target gas introduced from the first diffusion control portion 11 to the second diffusion control portion 13.

The second diffusion control portion 13 is a portion that applies predetermined diffusion resistance to the measurement target gas introduced into the first internal cavity 15 from the buffer space 12.

When the measurement target gas is introduced from the space outside the element substrate 100 into the first internal cavity 15, there are cases where the measurement target gas is rapidly taken from the gas inlet 10 into the element substrate 100 due to pressure fluctuations in the measurement target gas in the external space (i.e. pulsations in exhaust pressure if the measurement target gas is exhaust gas of an automobile). Even in this case, this configuration causes the measurement target gas to not be introduced directly into the first internal cavity 15, but introduced into the first internal cavity 15 after the concentration fluctuations in the measurement target gas have been cancelled out through the first diffusion control portion 11, the buffer space 12, and the second diffusion control portion 13. This makes the concentration fluctuations in the measurement target gas introduced into the first internal cavity 15 substantially negligible.

The first internal cavity 15 is provided as a space for adjusting the oxygen partial pressure in the measurement target gas introduced through the second diffusion control portion 13 (i.e. through the flow paths formed by the second diffusion control portion 13). The oxygen partial pressure is adjusted by operation of the main pump cell 21.

The main pump cell 21 is an electro-chemical pump cell constituted by the internal pump electrode 22, the external pump electrode 23, and the second solid electrolyte layer 6 that is sandwiched by these electrodes. The internal pump electrode 22 has a ceiling electrode portion 22a provided on substantially the entirety of the lower face of the second solid electrolyte layer 6 adjoining (facing) the first internal cavity 15. The external pump electrode 23 is provided in a region of the upper face of the second solid electrolyte layer 6 that corresponds to the ceiling electrode portion 22a so as to adjoin the external space.

The internal pump electrode 22 is formed so as to extend across the upper and lower solid electrolyte layers that define the first internal cavity 15 (i.e. the second solid electrolyte layer 6 and the first solid electrolyte layer 4), and the spacer layer 5 that forms side walls. Specifically, the ceiling electrode portion 22a is formed on the lower face of the second solid electrolyte layer 6 that forms a ceiling face of the first internal cavity 15, and a bottom electrode portion 22b is formed on the upper face of the first solid electrolyte layer 4 that forms a bottom face. Side electrode portions (not shown) that connect the ceiling electrode portion 22a and the bottom electrode portion 22b are formed on side wall faces (internal faces) of the spacer layer 5 that forms two side wall portions of the first internal cavity 15. In other words, the internal pump electrode 22 is provided in the form of a tunnel in the region in which the side electrode portions are disposed.

The internal pump electrode 22 and the external pump electrode 23 are formed as porous cermet electrodes (e.g. cermet electrodes formed with $ZrO_2$ and Pt containing 1% Au). Note that the internal pump electrode 22, which comes into contact with the measurement target gas, is made of a material that has a lowered capability of reducing a nitrogen oxide ($NO_x$) component in the measurement target gas.

The element substrate 100 is configured such that the main pump cell 21 can apply a desired pump voltage Vp0 between the internal pump electrode 22 and the external pump electrode 23, thereby causing a pump current Ip0 to flow in a positive direction or a negative direction between the internal pump electrode 22 and the external pump electrode 23, so that oxygen in the first internal cavity 15 is pumped out to the external space, or oxygen in the external space is pumped into the first internal cavity 15.

Furthermore, in order to detect the oxygen concentration (oxygen partial pressure) in the atmosphere in the first internal cavity 15, the internal pump electrode 22, the second solid electrolyte layer 6, the spacer layer 5, the first solid electrolyte layer 4, the third substrate layer 3, and the reference electrode 42 constitute an oxygen partial pressure detection sensor cell 80 for main pump control (i.e. an electro-chemical sensor cell).

The element substrate 100 is configured to be capable of identifying the oxygen concentration (oxygen partial pressure) in the first internal cavity 15 by measuring an electromotive force V0 in the oxygen partial pressure detection sensor cell 80 for main pump control. Furthermore, the pump current Ip0 is controlled by performing feedback control on Vp0 such that the electromotive force V0 is kept constant. Accordingly, the oxygen concentration in the first internal cavity 15 can be kept at a predetermined constant value.

The third diffusion control portion 16 is a region that applies predetermined diffusion resistance to the measurement target gas whose oxygen concentration (oxygen partial pressure) has been controlled by operation of the main pump cell 21 in the first internal cavity 15, thereby guiding the measurement target gas to the second internal cavity 17.

The second internal cavity 17 is provided as a space for further adjusting the oxygen partial pressure in the measurement target gas that has been introduced through the third diffusion control portion 16 (i.e. through the flow paths formed by the third diffusion control portion 16). The oxygen partial pressure is adjusted by operation of the auxiliary pump cell 50.

The auxiliary pump cell 50 is an auxiliary electro-chemical pump cell constituted by an auxiliary pump electrode 51, the external pump electrode 23 (which is not limited to the external pump electrode 23, and may be any appropriate electrode outside the element substrate 100), and the second solid electrolyte layer 6. The auxiliary pump electrode 51 has a ceiling electrode portion 51a provided on substantially the entirety of the lower face of the second solid electrolyte layer 6 facing the second internal cavity 17.

The auxiliary pump electrode 51 with this configuration is disposed inside the second internal cavity 17 in the form of a tunnel similar to the above-described internal pump electrode 22 provided inside the first internal cavity 15. That is, the ceiling electrode portion 51a is formed on the lower face of the second solid electrolyte layer 6 that forms the ceiling face of the second internal cavity 17, and a bottom electrode portion 51b is formed on the upper face of the first solid electrolyte layer 4 that forms the bottom face of the second internal cavity 17. Side electrode portions (not shown) that connect the ceiling electrode portion 51a and the bottom electrode portion 51b are formed on two wall faces of the spacer layer 5 that form side walls of the second internal cavity 17. Thus, the auxiliary pump electrode 51 is in the form of a tunnel.

Note that the auxiliary pump electrode 51 is also made of a material that has a lowered capability of reducing a nitrogen oxide component in the measurement target gas, similarly to the internal pump electrode 22.

The element substrate 100 is configured such that the auxiliary pump cell 50 can apply a desired voltage Vp1 between the auxiliary pump electrode 51 and the external pump electrode 23, so that oxygen in the atmosphere in the second internal cavity 17 is pumped out to the external space, or oxygen is pumped from the external space into the second internal cavity 17.

Furthermore, in order to control the oxygen partial pressure in the atmosphere in the second internal cavity 17, the auxiliary pump electrode 51, the reference electrode 42, the second solid electrolyte layer 6, the spacer layer 5, the first solid electrolyte layer 4, and the third substrate layer 3 constitute an oxygen partial pressure detection sensor cell 81 for auxiliary pump control (i.e. an electro-chemical sensor cell).

Note that the auxiliary pump cell 50 performs pumping using a variable power source 52 whose voltage is controlled based on an electromotive force V1 detected by the oxygen partial pressure detection sensor cell 81 for auxiliary pump control. Accordingly, the oxygen partial pressure in the atmosphere in the second internal cavity 17 is controlled to be a partial pressure that is low enough to substantially not affect the $NO_x$ measurement.

Furthermore, a pump current Ip1 is used to control the electromotive force of the oxygen partial pressure detection sensor cell 80 for main pump control. Specifically, the pump current Ip1 is input as a control signal to the oxygen partial pressure detection sensor cell 80 for main pump control, and the electromotive force V0 is controlled so as to keep a constant gradient of the oxygen partial pressure in the measurement target gas that is introduced from the third diffusion control portion 16 into the second internal cavity 17. In the case where the sensor is used as a $NO_x$ sensor, the oxygen concentration in the second internal cavity 17 is kept at a constant value of about 0.001 ppm by operation of the main pump cell 21 and the auxiliary pump cell 50.

That is, in the gas sensor element 101, the oxygen partial pressure is always kept at a fixed low value (a value that has substantially no effect on the $NO_x$ measurement) by operating the main pump cell 21 and the auxiliary pump cell 50.

The $NO_x$ concentration is measured by operation of a measurement pump cell 41. In the present embodiment, after the oxygen concentration (oxygen partial pressure) has been pre-adjusted in the first internal cavity 15, the measurement target gas introduced through the third diffusion control portion is subjected to a further adjustment of the oxygen partial pressure by the auxiliary pump cell 50 in the second internal cavity 17. This allows the oxygen concentration of the measurement target gas in the second internal cavity 17 to be kept constant with high accuracy. Thus, the element substrate 100 according to the present embodiment can measure the $NO_x$ concentration with high accuracy.

The measurement pump cell 41 measures the concentration of nitrogen oxide in the measurement target gas within the second internal cavity 17. That is, the measurement target gas whose oxygen concentration was adjusted by the auxiliary pump cell 50 within the second internal cavity 17 is subjected to measurement of the $NO_x$ concentration by operation of the measurement pump cell 41. The measurement pump cell 41 is an electrochemical pump cell that is constituted by the measurement electrode 44, the external pump electrode 23, the second solid electrolyte layer 6, the spacer layer 5, and the first solid electrolyte layer 4. In one example in FIG. 2, the measurement electrode 44 is provided on the upper face of the first solid electrolyte layer 4, which is adjacent to (faces) the second internal cavity 17. The measurement electrode 44 is surrounded by the porous diffusion layer 91.

The measurement electrode 44 is a porous cermet electrode and contains at least either silica ($SiO_2$) or alumina ($Al_2O_3$). For example, the measurement electrode 44 contains 80 to 90% by weight of Pt, 9.5 to 19.8% by weight of the constituent material of the first solid electrolyte layer 4 (e.g. $ZrO_2$), and 0.2 to 0.5% by weight of a mixture containing at least either silica or alumina. The measurement electrode 44 has a higher content ratio of precious metal than that of the constituent material of the first solid electrolyte layer 4. This strengthen the adhesion between the first solid electrolyte layer 4 and the measurement electrode 44. More-over, the measurement electrode 44 in the present embodiment contains 0.2 to 0.5% by weight of a mixture containing at least either silica or alumina. Here, when NO$_x$ is measured at a high temperature (e.g. 700 to 800 degrees Celsius), the measurement electrode 44 constantly repeats expansion and contraction. Even in such an environment, the following effects can be achieved as a result of the measurement electrode 44 containing at least either silica or alumina. That is, the expansion and contraction of the measurement electrode 44 is suppressed, and cracks, splitting, or the like does not occur in the porous diffusion layer 91 that covers the measurement electrode 44. Furthermore, a phenomenon in which the measurement electrode 44 peels away from the first solid electrolyte layer 4 does not occur.

The measurement electrode 44 also functions as a NO$_x$ reduction catalyst for reducing NO$_x$ present in the atmosphere in the second internal cavity 17. The measurement electrode 44 is surrounded by the porous diffusion layer 91, i.e. covered by the porous diffusion layer 91.

The porous diffusion layer 91 has a porosity that is 5% or more and 25% or less and is lower than the porosity of the leading end protection layer 200. When the porous diffusion layer 91 includes a plurality of faces (layers) with different porosities, the porous diffusion layer 91 has an average porosity that is 5% or more and 25% or less and is lower than the porosity of the leading end protection layer 200. For example, if, the two faces of the porous diffusion layer 91 in the thickness direction, namely the internal face opposing the measurement electrode 44 and the external face not opposing the measurement electrode 44 have different porosities, the average porosity of the porous diffusion layer 91 satisfies the following conditions. That is, the average porosity of the porous diffusion layer 91 is 5% or more and 25% or less and is lower than the porosity of the leading end protection layer 200. In other words, if, of the two faces, in the thickness direction, of the porous diffusion layer 91 covering the measurement electrode 44, the face closer to the measurement electrode 44 (i.e. the internal face) and the opposite face farther from the measurement electrode 44 (i.e. the external face) have different porosities, the average porosity of the porous diffusion layer 91 satisfies the following conditions. Specifically, the average porosity of the porous diffusion layer 91 is 5% or more and 25% or less and is lower than the porosity of the leading end protection layer 200. The face farther from the measurement electrode 44 (i.e. the external face) may be paraphrased as a face facing (opposing) the measurement target gas flow portion 7. In the example shown in FIG. 2 (and FIG. 3 below), the face farther from the measurement electrode 44 may also be paraphrased as a face facing the second internal cavity 17.

The porous diffusion layer 91 covers the measurement electrode 44, thereby making the diffusion mode of the measurement target gas (particularly, NO$_x$ gas) around the measurement electrode 44 a mode of diffusing while repeatedly colliding with a wall face of a sufficiently narrow flow path, as in Knudsen diffusion. The porous diffusion layer 91 also functions as a protective film for the measurement electrode 44. The porous diffusion layer 91 may be constituted by a porous film that mainly contains alumina (Al$_2$O$_3$), for example.

The NO$_x$ concentration is measured by operation of the measurement pump cell 41. That is, the element substrate 100 is configured to be capable of pumping out oxygen generated due to decomposition of nitrogen oxide in the atmosphere surrounding the measurement electrode 44 by means of the measurement pump cell 41, and detecting the amount of generated oxygen as a pump current Ip2.

To detect the oxygen partial pressure around the measurement electrode 44, the second solid electrolyte layer 6, the spacer layer 5, the first solid electrolyte layer 4, the third substrate layer 3, the measurement electrode 44, and the reference electrode 42 constitute an oxygen partial pressure detection sensor cell 82 (i.e. an electro-chemical sensor cell) for measurement pump control. A variable power supply 46 is controlled based on a voltage (electromotive force) V2 detected by the oxygen partial pressure detection sensor cell 82 for measurement pump control.

The measurement target gas that has been guided to the second internal cavity 17 through the flow path formed by the third diffusion control portion 16 reaches the measurement electrode 44 after the oxygen partial pressure has been controlled by the auxiliary pump cell 50. Particularly, the diffusion mode of the measurement target gas is made favorable for measurement of the nitrogen oxide (NO$_x$) concentrations through the porous diffusion layer 91; i.e. the predetermined diffusion resistance is applied to the measurement target gas. Nitrogen oxide in the measurement target gas around the measurement electrode 44 is reduced (2NO→N$_2$+O$_2$) to generate oxygen. The generated oxygen is then pumped by the measurement pump cell 41, and, at that time, a voltage Vp2 of the variable power supply is controlled such that a control voltage V2 detected by the oxygen partial pressure detection sensor cell 82 for measurement pump control is kept constant. The amount of oxygen generated around the measurement electrode 44 is proportional to the concentration of nitrogen oxide in the measurement target gas. Thus, the concentration of nitrogen oxide in the measurement target gas is calculated using the pump current Ip2 in the measurement pump cell 41.

Combining the measurement electrode 44, the first solid electrolyte layer 4, the third substrate layer 3, and the reference electrode 42 to constitute an oxygen partial pressure detection means as an electro-chemical sensor cell makes it possible to detect an electromotive force corresponding to the difference between the amount of oxygen generated due to the reduction of NO$_x$ components in the atmosphere around the measurement electrode 44 and the amount of oxygen in the reference atmosphere. This also makes it possible to obtain the concentration of nitrogen oxide components in the measurement target gas.

Also, the second solid electrolyte layer 6, the spacer layer 5, the first solid electrolyte layer 4, the third substrate layer 3, the external pump electrode 23, and the reference electrode 42 constitute an electro-chemical sensor cell 83. The element substrate 100 is configured to be capable of detecting the oxygen partial pressure in the measurement target gas outside the sensor, based on the electromotive force Vref obtained by this sensor cell 83.

In the element substrate 100 having the above configuration, the measurement target gas whose oxygen partial pressure is always kept at a constant low value (a value that has practically no effect on NO$_x$ measurement) can be brought to to the measurement pump cell 41 by operating the main pump cell 21 and the auxiliary pump cell 50. Accordingly, the element substrate 100 is configured to be capable of identifying the concentration of nitrogen oxide in the measurement target gas based on the pump current Ip2 that flows as a result of oxygen generated in response to the reduction of NO$_x$ being pumped out by the measurement pump cell 41 substantially in proportion to the concentration of nitrogen oxide in the measurement target gas.

Furthermore, the element substrate 100 includes a heater 70, which serves to adjust temperature to heat the element substrate 100 and keep the temperature thereof in order to increase the oxygen ion conductivity of the solid electrolyte. In one example in FIG. 2, the heater 70 includes a heater electrode 71, a heat generating unit 72, a lead portion 73, a heater insulating layer 74, and a pressure dispersing hole 75. The lead portion 73 may be constituted by a through-hole.

The heater 70 of the present embodiment is disposed closer to the lower face of the element substrate 100 than to the upper face of the element substrate 100, in the thickness direction (vertical direction/stacking direction) of the element substrate 100. Note that the arrangement of the heater 70 need not be limited to this example, and may be selected as appropriate, according to the mode of implementation.

The heater electrode 71 is an electrode formed so as to be in contact with the lower face of the first substrate layer 1 (the lower face of the element substrate 100). The heater electrode 71 can be connected to an external power supply to supply power to the heater 70 from the outside.

The heat generating unit 72 is an electrical resistor formed in a manner held between the second substrate layer 2 and the third substrate layer 3 from above and below. The heat generating unit 72 is connected via the lead portion 73 to the heater electrode 71. When electricity is supplied from the outside via the heater electrode 71, the heat generating unit 72 generates heat, thereby heating the solid electrolyte constituting the element substrate 100 and keeping the temperature thereof.

The heat generating unit 72 is buried across the entire region of the first internal cavity 15 to the second internal cavity 17, and enables the entire element substrate 100 to be adjusted at a temperature at which the aforementioned solid electrolyte is activated.

The heater insulating layer 74 is an insulating layer formed with insulators that are made of alumina or the like, over the upper and lower faces of the heat generating unit 72. The heater insulating layer 74 is formed for the purpose of providing electrical insulation between the second substrate layer 2 and the heat generating unit 72, and electrical insulation between the third substrate layer 3 and the heat generating unit 72.

The pressure dispersing hole 75 is a portion that extends through the third substrate layer 3 and is connected to the reference gas introduction space 43, and is formed for the purpose of mitigating the increase in internal pressure caused by a temperature rise in the heater insulating layer 74.

Porous Diffusion Layer

Figure 3:
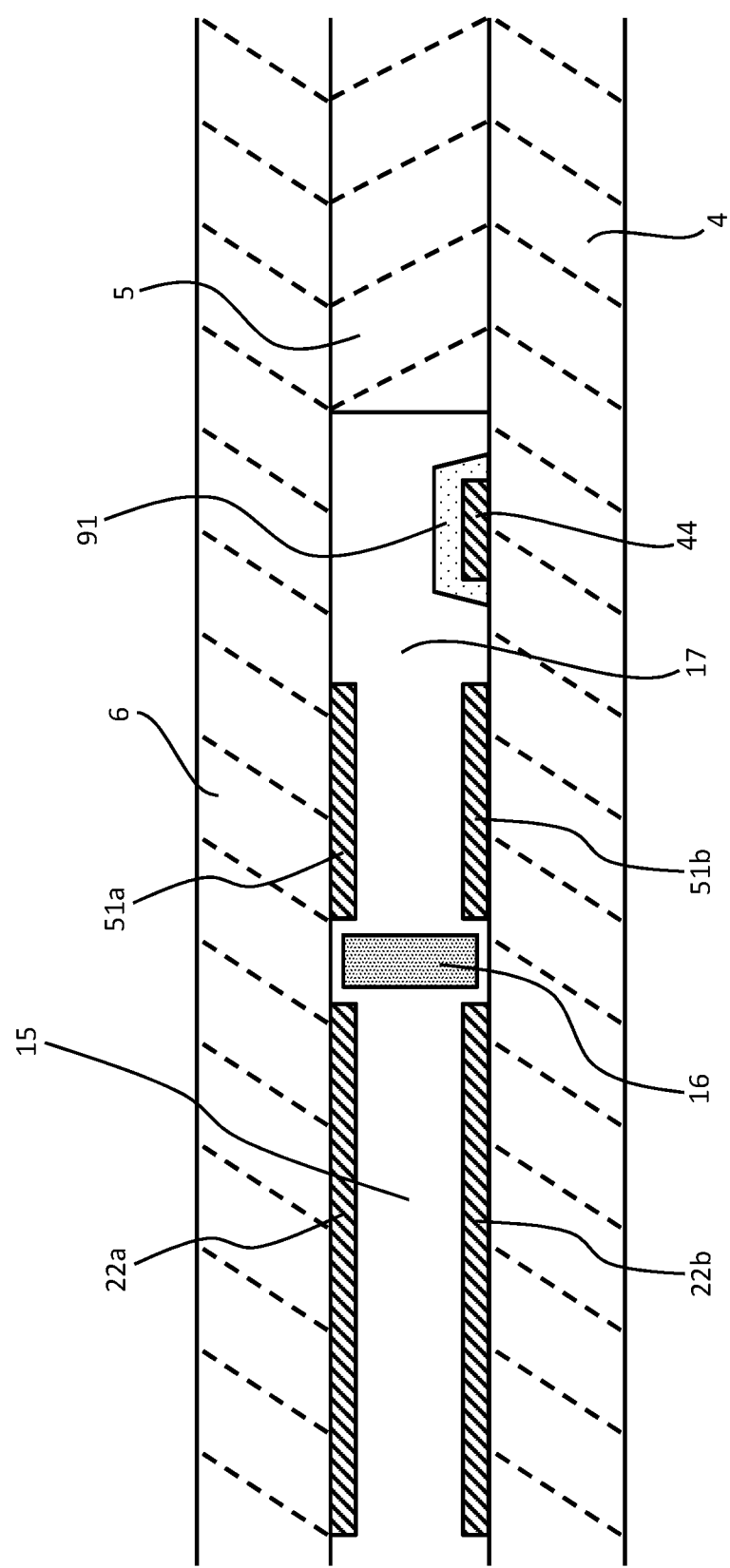
FIG. 3 is an illustrative enlarged view of key parts of the element substrate in FIG. 2.

FIG. 3 is an illustrative enlarged view of key parts of the element substrate 100. Specifically, FIG. 3 shows the details of the porous diffusion layer 91, which is a porous layer covering the measurement electrode 44 disposed in the second internal cavity 17. The diffusion resistance of the measurement target gas supplied to the measurement electrode 44 is adjusted by providing a porous layer covering the measurement electrode 44, namely the porous diffusion layer 91 whose porosity is 5% or more and 25% or less and is lower than the porosity of the leading end protection layer 200. Particularly, the porous diffusion layer 91 can make the diffusion mode of the measurement target gas (particularly, $NO_x$ gas) around the measurement electrode 44 a mode of diffusing while repeatedly colliding with a wall face of a sufficiently narrow flow path, as in Knudsen diffusion. This reduces fluctuations in $NO_x$ output and the degradation of the measurement electrode that occur when the diffusion mode around the measurement electrode 44 is molecular diffusion, even if the $H_2O$ concentration is high.

The element substrate 100 illustrated in FIG. 3 includes an internal space (the measurement target gas flow portion 7)

that is provided by hollowing out a portion of the spacer layer 5 between the first solid electrolyte layer 4 and the second solid electrolyte layer 6, as described with reference to FIG. 2. The measurement target gas flow portion 7 has an upper portion (upper face) demarcated (defined) by the lower face of the second solid electrolyte layer 6, and a lower portion (lower face) demarcated (defined) by the upper face of the first solid electrolyte layer 4. The measurement target gas flow portion 7 includes the first internal cavity 15 and the second internal cavity 17.

The first internal cavity 15 is a space for adjusting the oxygen partial pressure in the measurement target gas by means of the main pump cell 21, which is constituted by the internal pump electrode 22 (the ceiling electrode portion 22a and the bottom electrode 22b), the external pump electrode 23 (not shown in FIG. 3), and the second solid electrolyte layer 6.

The third diffusion control portion 16 applies predetermined diffusion resistance to the measurement target gas whose oxygen concentration (oxygen partial pressure) has been controlled by operation of the main pump cell 21 in the first internal cavity 15, and guides the measurement target gas to the second internal cavity 17. That is, the third diffusion control portion 16 forms a flow path of the measurement target gas from the first internal cavity 15 to the second internal cavity 17.

In the second internal cavity 17, the auxiliary pump cell 50 further adjusts the oxygen partial pressure in the measurement target gas. The auxiliary pump cell 50 is constituted by the auxiliary pump electrode 51 (the ceiling electrode portion 51a and the bottom electrode portion 51b), the external pump electrode 23 (not shown in FIG. 3), and the second solid electrolyte layer 6.

In the second internal cavity 17, the measurement target gas whose oxygen partial pressure has been adjusted by the auxiliary pump cell 50 is subjected to measurement of the nitrogen oxide concentration by the measurement pump cell 41. The measurement pump cell 41 is constituted by the measurement electrode 44, the second solid electrolyte layer 6, the spacer layer 5, the first solid electrolyte layer 4, and the external pump electrode 23 (not shown in FIG. 3).

The measurement electrode 44 is covered by the porous diffusion layer 91 whose porosity is 5% or more and 25% or less and is lower than the porosity of the leading end protection layer 200. This porous diffusion layer 91 can make the diffusion mode of the measurement target gas (particularly, $NO_x$ gas) around the measurement electrode 44 a mode of diffusing while repeatedly colliding with a wall face of a sufficiently narrow flow path, as in Knudsen diffusion.

Here, if the porous diffusion layer 91 having large diffusion resistance is located around the measurement electrode 44, it is possible that the porous diffusion layer 91 will be clogged with poisonous substances or the like. To prevent this, the gas sensor element 101 has the leading end protection layer 200 that covers at least the face of the element substrate 100 in which the gas inlet 10 is open, as illustrated in FIG. 1. Further, the porosity of the porous diffusion layer 91 is lower than the porosity of the leading end protection layer 200, i.e. the porosity of the leading end protection layer 200 is higher than the porosity of the porous diffusion layer 91.

Adopting this configuration allows poisonous substances or the like that cause clogging in the porous diffusion layer 91 to be captured in advance in the leading end protection layer 200. Thus, the amount of poisonous substances or the like in the measurement target gas reaching the porous diffusion layer 91 and the measurement electrode 44 is negligible. This can reduce the likelihood that the porous diffusion layer 91 will be clogged with poisonous substances or the like. Even if a poisonous substance or the like reaches the measurement electrode 44 and adheres to the measurement electrode 44, this poisonous substance hardly affects the oxidation/reduction capacity of the electrode metal.

Thus, the gas sensor element 101 according to the present embodiment can prevent clogging in the porous diffusion layer 91 caused by poisonous substances or the like, and can also reduce the impact of poisonous substances or the like on the oxidation/reduction capacity of the measurement electrode 44. Specifically, a decrease in the measurement accuracy of the gas sensor element 101 resulting from use is favorably prevented, i.e. the measurement accuracy thereof is kept stable even after repeated use.

If the two faces of the porous diffusion layer 91 in the thickness direction, namely the internal face opposing the measurement electrode 44 and the external face have different porosities, the porous diffusion layer 91 has an average porosity that is 5% or more and 25% or less and is lower than the porosity of the leading end protection layer 200. In other words, if the two faces of the porous diffusion layer 91 in the thickness direction, namely the face closer to the measurement electrode 44 and the face further away therefrom have different porosities, the porous diffusion layer 91 has an average porosity that is 5% or more and 25% or less and is lower than the porosity of the leading end protection layer 200. For example, if the porous diffusion layer 91 includes a plurality of faces (layers) with different porosities, the average porosity of the porous diffusion layer 91 that is calculated from the porosity of each of the plurality of faces (layers) is 5% or more and 25% or less, and is lower than the porosity of the leading end protection layer 200. An example of the porous diffusion layer that covers the measurement electrode 44 and has a face closer to the measurement electrode 44 (i.e. the internal face) and a face further away therefrom (i.e. the external face) that have different porosities will be described in detail later with reference to FIG. 5.

Need for Contact Between Porous Diffusion Layer and Measurement Electrode

The porous diffusion layer 91, whose porosity is 5% or more and 25% or less and is lower than the porosity of the leading end protection layer 200, is provided to make the diffusion mode around the measurement electrode 44 favorable, specifically, such that the distance d2 to the measurement electrode 44 is 0.15 mm or less. The porous diffusion layer 91 may cover the measurement electrode 44 in contact therewith, or may cover the measurement electrode 44 without being in contact therewith such that the distance d2 to the measurement electrode 44 is 0.15 mm or less. The following is a detailed description, with reference to FIGS. 4 to 6, of the porous diffusion layer that covers the measurement electrode 44 and has a porosity that is 5% or more and 25% or less and is lower than the porosity of the leading end protection layer 200, for an example of being in contact with the measurement electrode 44 and an example of not being in contact with the measurement electrode 44.

Figure 4:
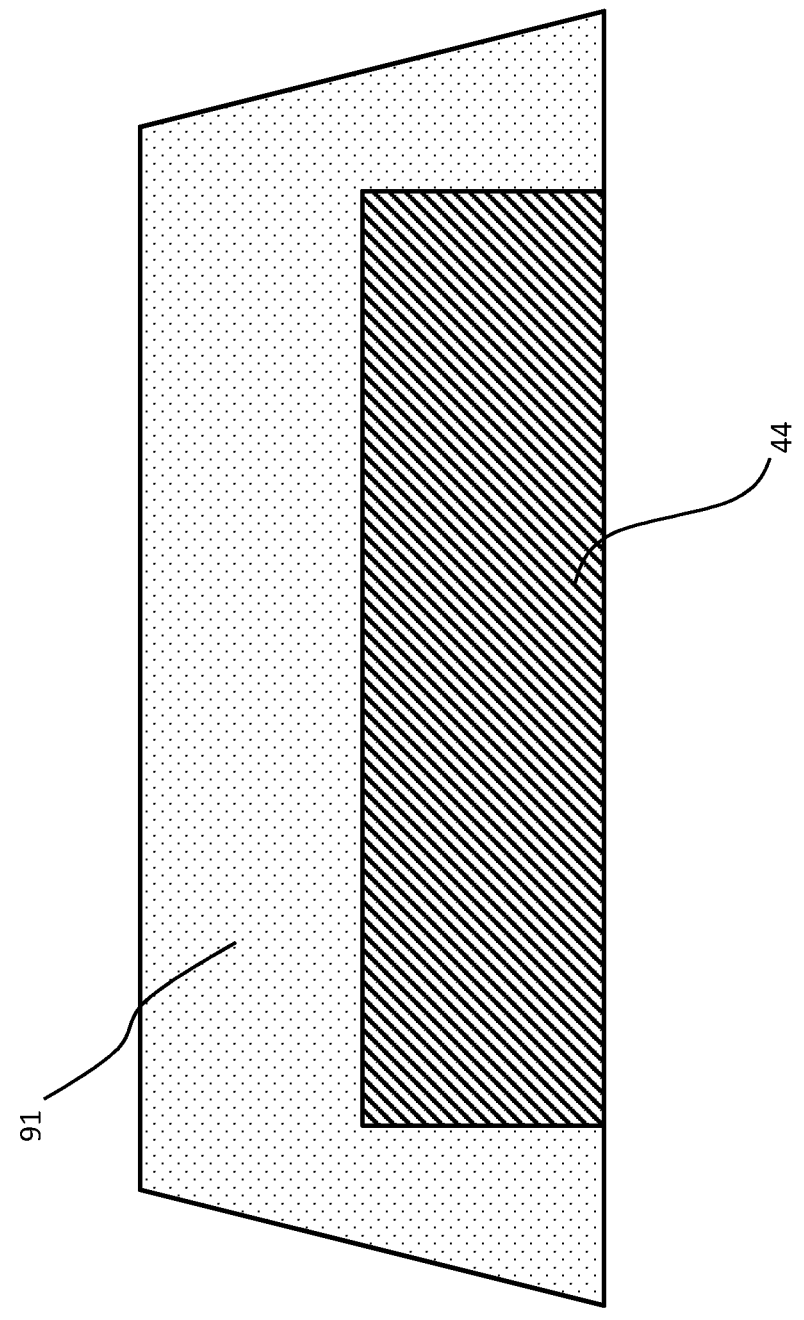
FIG. 4 shows an example of the relationship between a measurement electrode and a porous diffusion layer of the element substrate in FIG. 2.

Example where Porous Diffusion Layer and Measurement Electrode are in Contact with Each Other FIG. 4 shows an example of the relationship between the measurement electrode 44 and the porous diffusion layer 91 of the element substrate 100. Specifically, FIG. 4 shows an example of the porous diffusion layer 91 that covers the measurement electrode 44 in contact with the measurement electrode 44. The porous diffusion layer 91 illustrated in FIG. 4 is a porous layer having a constant porosity that is 5% or more and 25% or less over the entirety thereof, and covers the measurement electrode 44 in contact with the upper, front, and back faces of the measurement electrode 44. The porous diffusion layer 91, which covers the measurement electrode 44 in contact with the measurement electrode 44, can make the diffusion mode of the measurement target gas (particularly, $NO_x$ gas) moving toward the measurement electrode 44 a mode of diffusing while repeatedly colliding with a wall face of a sufficiently narrow flow path, as in Knudsen diffusion. In the gas sensor element 101, the porous diffusion layer that covers the measurement electrode 44 and whose porosity is 5% or more and 25% or less and is lower than the porosity of the leading end protection layer 200 may be in contact with the measurement electrode 44, as illustrated in FIG. 4. However, it is not essential for the gas sensor element 101 that the porous diffusion layer is in contact with the measurement electrode 44. In the gas sensor element 101, the porous diffusion layer that covers the measurement electrode 44 and whose porosity is 5% or more and 25% or less and is lower than the porosity of the leading end protection layer 200 need not be in contact with the measurement electrode 44. An example of the porous diffusion layer that is not in contact with the measurement electrode 44 will be described later with reference to FIG. 6.

Figure 5:
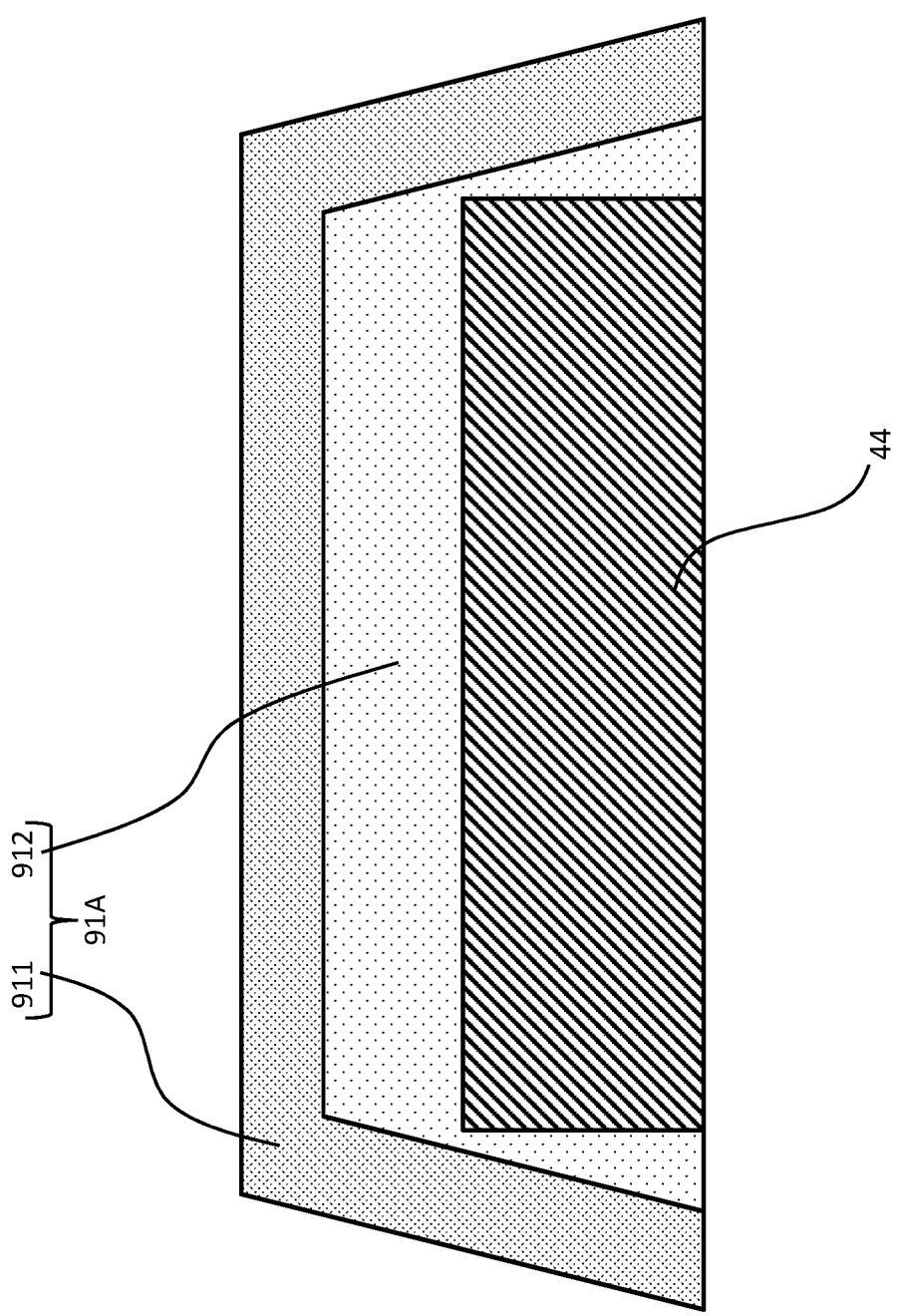
FIG. 5 shows an example of a porous diffusion layer according to a variation.

FIG. 5 shows an example of a porous diffusion layer 91A according to a variation. Specifically, FIG. 5 shows an example of the porous diffusion layer 91A whose porosity is not constant throughout, i.e. that includes a plurality of faces (layers) with different porosities. The porous diffusion layer 91 illustrated in FIG. 4 has a porosity that is constant throughout and is 5% or more and 25% or less. However, it is not essential for the gas sensor element 101 (the element substrate 100) that the porosity of the porous diffusion layer surrounding the measurement electrode 44 is constant over the entire porous diffusion layer. In the gas sensor element 101 (the element substrate 100), the porous diffusion layer surrounding the measurement electrode 44 may have an internal face opposing the measurement electrode 44 and an external face that have different porosities, as the porous diffusion layer 91A illustrated in FIG. 5 does. In other words, the two faces of the porous diffusion layer covering the measurement electrode 44 in the thickness direction, namely the internal face opposing the measurement electrode 44 and the external face not opposing the measurement electrode 44 may have different porosities. The gas sensor element 101 may have the porous diffusion layer 91A instead of the porous diffusion layer 91.

The porous diffusion layer 91A illustrated in FIG. 5 includes a first porous diffusion layer 911 (external face), which is a porous layer facing the measurement target gas flow portion 7 (the second internal cavity 17), and a second porous diffusion layer 912 (internal face), which is a porous layer opposing the measurement electrode 44. The first porous diffusion layer 911 and the second porous diffusion layer 912 have different porosities, with the porosity of the second porous diffusion layer 912 being higher than the porosity of the first porous diffusion layer 911. In other words, the internal face (the second porous diffusion layer 912) opposing the measurement electrode 44, of the two faces of the porous diffusion layer 91A in the thickness direction, has a porosity higher than the porosity of the external face (the first porous diffusion layer 911). In the example shown in FIG. 5, of the two faces of the porous diffusion layer 91A in the thickness direction, the internal face (the second porous diffusion layer 912) opposes the measurement electrode 44, and the external face (the first porous diffusion layer 911) faces (opposes) the measurement target gas flow portion 7.

The following effects can be achieved as a result of the porosity of the internal face opposing the measurement electrode 44, of the two faces of the porous diffusion layer 91A in the thickness direction, being higher than the porosity of the external face (e.g. the face facing the measurement target gas flow portion 7). That is, it is possible to reduce the impact of $H_2O$ on the surface of the measurement electrode 44 being decomposed to generate $H_2$, and shorten the light-off time required from when the gas sensor starts until when it enters a steady operation state. This is for the following reasons.

If $H_2O$ on the surface of the measurement electrode 44 decomposes to generate $H_2$ immediately after the gas sensor is driven, the potential difference (i.e. oxygen concentration difference) between the measurement electrode 44 and the reference electrode 42 increases. Thus, pumping oxygen into the measurement electrode 44 may result in an undershoot waveform and a longer light-off time.

However, the gas sensor element 101 achieves the following effects as a result of the porosity of the internal face (on the side closer to the measurement electrode 44; the second porous diffusion layer 912) opposing the measurement electrode 44 being higher than the porosity of the external face (the first porous diffusion layer 911), as in the porous diffusion layer 91A. That is, making the porosity of the internal face opposing the measurement electrode 44 higher than the porosity of the external face enables the gas sensor element 101 to quickly diffuse $H_2$ generated in the vicinity of the surface of the measurement electrode 44. In other words, $H_2$ generated due to decomposition of $H_2O$ on the surface of the measurement electrode 44 can be quickly diffused by the second porous diffusion layer 912 (internal face opposing the measurement electrode 44), which has a higher porosity than the porosity of the first porous diffusion layer 911 (external face). Thus, the potential difference between the measurement electrode 44 and the reference electrode 42 does not excessively increase during constant control in the gas sensor element 101, and the gas sensor element 101 can shorten the light-off time. In other words, even if $H_2$ is generated due to decomposition of $H_2O$ on the surface of the measurement electrode 44, the gas sensor element 101 can reduce the impact of $H_2$ and prevent an increase in the light-off time.

Particularly, in the case where no space is provided between the porous diffusion layer 91A and the measurement electrode 44, i.e. they are in contact with each other, it is desirable that the porosity of the second porous diffusion layer 912 is higher than the porosity of the first porous diffusion layer 911. In other words, if the porous diffusion layer 91A and the measurement electrode 44 are in contact with each other, it is desirable that the porosity of the internal face of the porous diffusion layer 91A that is in contact with the measurement electrode 44 is higher than the porosity of the external face (the face not in contact with the measurement electrode 44 on the surface side; e.g. the face facing the measurement target gas flow portion 7). The porous diffusion layer 91A can achieve the following effects as a result of the porosity of the internal face of the porous diffusion layer 91A that is in contact with the measurement electrode 44 being higher than the porosity of the external face, even in the case where the porous diffusion layer 91A and the measurement electrode 44 are in contact with each other. That is, the porous diffusion layer 91A can reduce the impact of $H_2$ generated due to decomposition of $H_2O$ on the surface of the measurement electrode 44, and shorten the light-off time.

Note that the porosity is a value derived, for example, by applying a known image processing method (e.g. binarization) to an image (SEM image) obtained by observation using a scanning electron microscope (SEM). Specifically, the porosity of the face (the second porous diffusion layer 912) of the porous diffusion layer 91A that is closer to the measurement electrode 44 was derived as follows, for example. That is, first, a SEM image was obtained in the vicinity of the center of the measurement electrode 44 when viewed in the lengthwise direction (the axial direction of the sensor element), in the range from 10 to 15 μm from the interface between the measurement electrode 44 and the porous diffusion layer 91A (the second porous diffusion layer 912). Next, the porosity of the face (the second porous diffusion layer 912) of the porous diffusion layer 91A that is closer to the measurement electrode 44 was obtained by applying a known image processing method, such as binarization, to the obtained SEM image. The same approach was applied to obtain the porosity on the surface side of the porous diffusion layer 91A (the face facing the measurement target gas flow portion 7; specifically, the first porous diffusion layer 911). That is, the porosity of the on the surface side of the porous diffusion layer 91A was derived by obtaining a SEM image in the range from 10 to 15 μm from the surface (e.g. upper face) of the porous diffusion layer 91A (the first porous diffusion layer 911) and applying a known image processing method to the obtained SEM image.

As mentioned above, the porosity of the second porous diffusion layer 912 of the porous diffusion layer 91A is higher than the porosity of the first porous diffusion layer 911, e.g. by 10% or more. That is, the porosity of the internal face (the second porous diffusion layer 912) opposing the measurement electrode 44, of the two faces of the porous diffusion layer 91A in the thickness direction, is 10% or more higher than the porosity of the external face (the first porous diffusion layer 911).

As mentioned above, the following effects can be achieved as a result of the porosity of the second porous diffusion layer 912 (internal face opposing the measurement electrode 44) of the porous diffusion layer 91A being higher than the porosity of the first porous diffusion layer 911 (external face). That is, this configuration enables the porous diffusion layer 91A to quickly diffuse $H_2$ generated in the vicinity of the surface of the measurement electrode 44 and prevent an increase in the light-off time. Further, the inventors confirmed that the light-off time is shorter when the porosity of the internal face opposing the measurement electrode 44, of the two faces of the porous diffusion layer 91A in the thickness direction, is 10% or more higher than the porosity of the external face, than when the porosity of the internal face is less than 10% higher than the porosity of the external face. Hence, it is desirable in the porous diffusion layer 91A that the difference between the porosity of the internal face opposing the measurement electrode 44 (the face closer to the measurement electrode 44; the second porous diffusion layer 912) and the external face (the first porous diffusion layer 911) is 10% or more. Specifically, it is desirable in the porous diffusion layer 91A that the porosity of the internal face opposing the measurement electrode 44 is 10% or more higher than the porosity of the external face. The gas sensor element 101 can shorten the light-off time as a result of the porosity of the second porous diffusion layer 912 of the porous diffusion layer 91A being 10% or more higher than the porosity of the first porous diffusion layer 911, compared to when the porosity of the second porous diffusion layer 912 is less than 10% higher than the porosity of the first porous diffusion layer 911. That is, the gas sensor element 101 can further shorten the light-off time as a result of the porosity of the internal face opposing the measurement electrode 44, of the two faces of the porous diffusion layer 91A in the thickness direction, being at least 10% higher than the porosity of the external face (the face facing the measurement target gas flow portion 7).

As described above, the porosity of the internal face opposing the measurement electrode 44, of the two faces of the porous diffusion layer 91A in the thickness direction, is higher than the porosity of the external face (e.g. the face facing the measurement target gas flow portion 7), particularly by 10% or more. Here, the mode in which the porosity changes in the porous diffusion layer 91A from the internal face opposing the measurement electrode 44 toward the external face not opposing the measurement electrode 44 (e.g. the face facing the measurement target gas flow portion 7) is not particularly limited.

That is, the porosity of the porous diffusion layer 91A may change stepwise (discontinuously) from the internal face opposing the measurement electrode 44 toward the external face, as illustrated in FIG. 5. The porous diffusion layer 91A illustrated in FIG. 5 has an external face (e.g. upper face) facing the measurement target gas flow portion 7 that is constituted by the first porous diffusion layer 911, and an internal face (e.g. lower face) opposing (facing) the measurement electrode 44 that is constituted by the second porous diffusion layer 912. The first porous diffusion layer 911 and the second porous diffusion layer 912 have different porosities; specifically, the porosity of the first porous diffusion layer 911 is lower than the porosity of the second porous diffusion layer 912, e.g. by 10% or more. In other words, the porous diffusion layer 91A includes a plurality of layers with different porosities, and the porosity of the porous diffusion layer 91A changes stepwise (discontinuously) from the internal face opposing the measurement electrode 44 toward the external face.

Alternatively, the porosity of the porous diffusion layer 91A may change continuously from the internal face opposing (facing) the measurement electrode 44 toward the external face (e.g. the face facing the measurement target gas flow portion 7). For example, the porous diffusion layer 91A may be configured such that the porosity gradually decreases from the internal face opposing (facing) the measurement electrode 44 toward the external face (e.g. the face facing the measurement target gas flow portion 7), resulting in a difference in the porosity therebetween being 10% or more.

As described above, the porosity of the internal face opposing the measurement electrode 44, of the two faces of the porous diffusion layer 91A in the thickness direction, is higher than the porosity of the external face, specifically by 10% or more. The mode in which the porosity of the porous diffusion layer 91A changes from the internal face opposing the measurement electrode 44 toward the external face is not particularly limited; for example, the porosity may change stepwise (discontinuously) or continuously.

If, in the gas sensor element 101, the porous diffusion layer surrounding the measurement electrode 44 includes a plurality of faces (layers) with different porosities, as the porous diffusion layer 91A does, the average porosity of the porous diffusion layer satisfies the following conditions. That is, if the porous diffusion layer surrounding the measurement electrode 44 includes a plurality of faces with different porosities, the average porosity of the porous diffusion layer is 5% or more and 25% or less, and is lower than the porosity of the leading end protection layer 200. For example, in the porous diffusion layer 91A with different porosities between the face closer to the measurement electrode 44 (i.e. the internal face) to the face farther away therefrom (i.e. the external face) as illustrated in FIG. 5, the average porosity of the porous diffusion layer 91A is 5% or more and 25% or less, and is lower than the porosity of the leading end protection layer 200. Specifically, the average porosity of the porous diffusion layer 91A that is calculated based on the porosity of the first porous diffusion layer 911 and the porosity of the second porous diffusion layer 912 is 5% or more and 25% or less, and is lower than the porosity of the leading end protection layer 200. That is, if the porous diffusion layer 91A includes a plurality of faces (layers), particularly if the porous diffusion layer 91A includes a plurality of faces with different porosities, the average porosity of the porous diffusion layer 91A is 5% or more and 25% or less, and is lower than the porosity of the leading end protection layer 200.

FIG. 5 shows an example where the porous diffusion layer 91A, which has different porosities between the internal face opposing the measurement electrode 44 and the external face not opposing the measurement electrode 44, covers the measurement electrode 44 in contact with the measurement electrode 44. However, it is not essential for the porous diffusion layer 91A to cover the measurement electrode 44 in contact with the measurement electrode 44. A space (gap) may be provided between the porous diffusion layer 91A and the measurement electrode 44. Similarly, a space (gap) may be provided between the porous diffusion layer 91 and the measurement electrode 44. That is, in the gas sensor element 101, the porous diffusion layer that covers the measurement electrode 44 and has a porosity that is 5% or more and 25% or less and is lower than the porosity of the leading end protection layer 200 need not be in contact with the measurement electrode 44, and a space may be provided therebetween. A description will be given below, with reference to FIG. 6, of an example of the gas sensor element 101 where the porous diffusion layer covering the measurement electrode 44 is not in contact with the measurement electrode 44.

Figure 6:
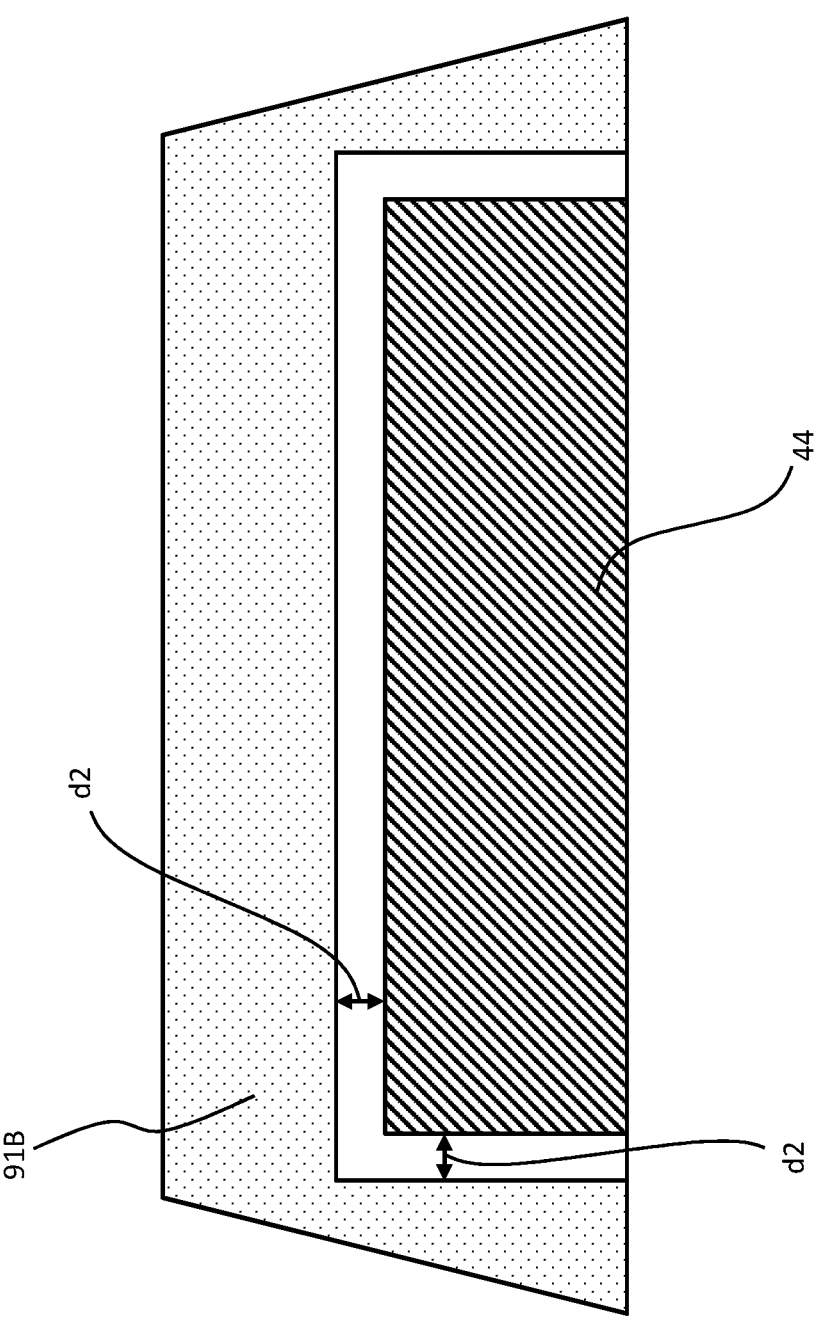
FIG. 6 shows an example of the relationship between a measurement electrode and a porous diffusion layer according to a variation.

Example where Porous Diffusion Layer and Measurement Electrode are not in Contact with Each Other FIG. 6 shows an example of the relationship between the measurement electrode 44 and a porous diffusion layer 91 (porous diffusion layer 91B) according to a variation. Specifically, FIG. 6 shows an example of a porous diffusion layer 91B that covers the measurement electrode 44 without being in contact with the measurement electrode 44, and the distance d2 to the measurement electrode 44 is 0.15 mm or less. The porous diffusion layers 91 and 91A illustrated in FIGS. 4 and 5 cover the measurement electrode 44 in contact with the measurement electrode 44. However, it is not essential that, in the gas sensor element 101 (the element substrate 100), the porous diffusion layer surrounding the measurement electrode 44 is in contact with the measurement electrode 44. Like the porous diffusion layer 91B illustrated in FIG. 6, the porous diffusion layer in the gas sensor element 101 may alternatively cover the measurement electrode 44 without being in contact with the measurement electrode 44. In other words, a space (gap) may be present between the porous diffusion layer and the measurement electrode 44. The gas sensor element 101 may have the porous diffusion layer 91B that covers the measurement electrode 44 without being in contact with the measurement electrode 44 and has a porosity that is 5% or more and 25% or less and is lower than the porosity of the leading end protection layer 200, instead of the porous diffusion layer 91.

The porous diffusion layer 91B illustrated in FIG. 6 is not in contact with the measurement electrode 44. That is, a space (gap) is provided between the measurement electrode 44 and the porous diffusion layer 91B located around the measurement electrode 44. Note that the distance d2 between the measurement electrode 44 and the porous diffusion layer 91B surrounding the measurement electrode 44 is 0.15 mm or less. The distance d2 between the porous diffusion layer 91B and the measurement electrode 44 refers to, for example, the distance from the face of the porous diffusion layer 91B that faces (opposes) the measurement electrode 44 to the measurement electrode 44 (particularly, the surface thereof; the face facing (opposing) the porous diffusion layer 91B).

The porous diffusion layer 91B is not in contact with the measurement electrode 44, and here, the distance d2 to the measurement electrode 44 is 0.15 mm or less, i.e. the distance d2 between the porous diffusion layer 91B and the measurement electrode 44 is 0.15 mm or less. As mentioned above, if $H_2O$ on the surface of the measurement electrode 44 decomposes to generate $H_2$ immediately after the sensor is driven, there are cases where $H_2$ around the measurement electrode 44 increases the light-off time required from when the gas sensor starts until when it enters a steady operation state. In the gas sensor element 101, a space (gap) is provided between the measurement electrode 44 and the porous diffusion layer 91B, thus allowing $H_2$ generated in the vicinity of the surface of the measurement electrode 44 to be quickly diffused. As a result, even if $H_2O$ on the surface of the measurement electrode 44 is decomposed to generate $H_2$, the gas sensor element 101 can reduce the impact of $H_2$ and prevent an increase in the light-off time. That is, providing a space between the porous diffusion layer 91 and the measurement electrode 44 allows the gas sensor element 101 to quickly diffuse $H_2$ generated due to the decomposition of $H_2O$ on the surface of the measurement electrode 44. Accordingly, the potential difference between the measurement electrode 44 and the reference electrode 42 does not excessively increase during constant control, and the gas sensor element 101 can shorten the light-off time.

However, providing an excessively large gap between the measurement electrode 44 and the porous diffusion layer 91B will reduce the effect of changing the diffusion mode around the measurement electrode 44 into a mode of diffusing while repeatedly colliding with a wall face of a sufficiently narrow flow path, as in Knudsen diffusion, achieved by the porous diffusion layer 91B. In the gas sensor element 101, the distance between the measurement electrode 44 and the porous diffusion layer 91B is 0.15 mm or less. The inventors confirmed that the porous diffusion layer 91B can make the diffusion mode around the measurement electrode 44 favorable, as in the case where they were in contact with each other, by setting the distance between the measurement electrode 44 and the porous diffusion layer 91B to 0.15 mm or less. That is, it was confirmed that the porous diffusion layer 91B that is separated from the measurement electrode 44 by a distance of 0.15 mm or less can make the diffusion mode around the measurement electrode 44 a mode of diffusing while repeatedly colliding with a wall face of a sufficiently narrow flow path, as in Knudsen diffusion. Accordingly, the gas sensor element 101 can suppress fluctuations in $NO_x$ output and the degradation of the measurement electrode 44, which are considered to be caused by molecular diffusion of $NO_x$ under high $H_2O$ concentration, by means of the porous diffusion layer 91B that is separated from the measurement electrode 44 by a distance of 0.15 mm or less. In other words, the gas sensor element 101 can reduce the impact of $H_2O$ gas on $NO_x$ gas (and $O_2$ gas) by means of the porous diffusion layer 91B that is separated from the measurement electrode 44 by a distance of 0.15 mm or less.

Note that the porous diffusion layer that covers the measurement electrode 44 without being in contact with the measurement electrode 44, such as the porous diffusion layer 91B, may also have an internal face opposing the measurement electrode 44 that has a porosity higher than the porosity of an external face. For example, the porosity of the internal face opposing the measurement electrode 44, of the two faces of the porous diffusion layer 91B in the thickness direction, may be higher than the porosity of the external face. The porous diffusion layer, which is separated from the measurement electrode 44 by a distance d2 of 0.15 mm or less and covers the measurement electrode 44 without being in contact with the measurement electrode 44, can diffuse $H_2$ more quickly as a result of including the internal face opposing the measurement electrode 44 that has a porosity higher than the porosity of the external face. Accordingly, the gas sensor element 101 that includes the above porous diffusion layer can further shorten the light-off time.

Position at which Measurement Electrode is Disposed

So far, an example where the measurement electrode 44 is disposed in the second internal cavity 17 has been described with reference to FIGS. 2 to 6. However, it is not essential for the gas sensor element 101 that the measurement electrode 44 is disposed in the second internal cavity 17. The measurement electrode 44 may alternatively be disposed in the first internal cavity 15. Further, it is not essential that the element substrate of the gas sensor element 101 has a two-cavity structure, i.e. includes the first internal cavity 15 and the second internal cavity 17. For example, the element substrate of the gas sensor element 101 may alternatively have a one-cavity structure, i.e. a configuration without the diffusion control portion. Further, the element substrate of the gas sensor element 101 may have three or more cavities, e.g. a three-cavity structure (i.e. a structure with three internal cavities), or a structure with four or more internal cavities. An example where the element substrate of the gas sensor element 101 has a three-cavity structure will be described below with reference to FIG. 7.

Example where Measurement Electrode is Disposed in Third Internal Cavity

Figure 7:
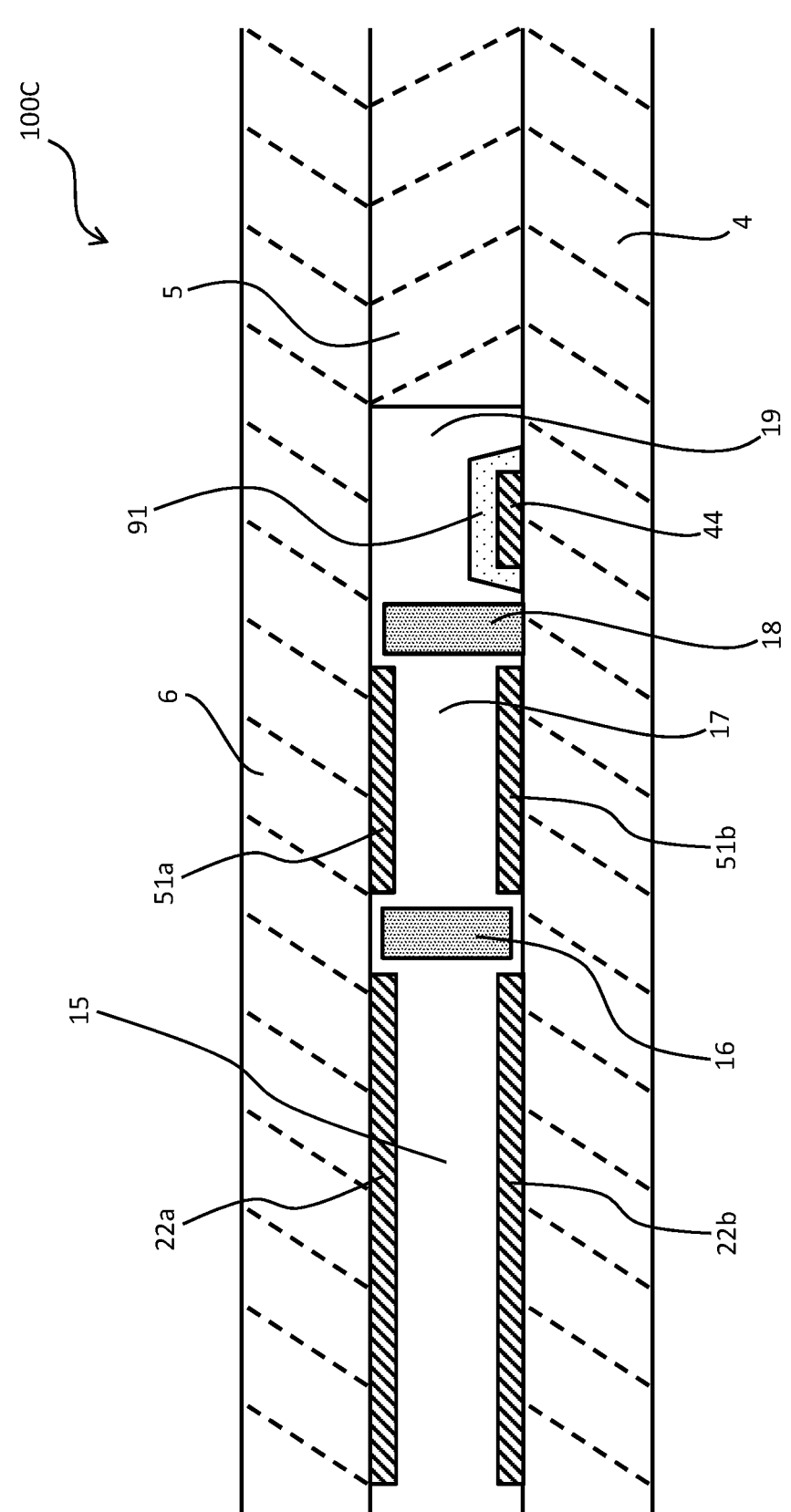
FIG. 7 is an illustrative enlarged view of key parts of an element substrate according to a variation.

FIG. 7 is an illustrative enlarged view of key parts of an element substrate 100C according to a variation. Specifically, FIG. 7 is an illustrative enlarged view of key parts of the element substrate 100C, which includes three internal cavities (the first internal cavity 15, the second internal cavity 17, and a third internal cavity 19). The gas sensor element 101 may have the element substrate 100C, which will be described in detail below, instead of the element substrate 100.

Like the element substrate 100, the element substrate 100C includes a laminate formed by stacking the first substrate layer 1, the second substrate layer 2, the third substrate layer 3, the first solid electrolyte layer 4, the spacer layer 5, and the second solid electrolyte layer 6 in this order from the bottom. Further, like the element substrate 100, the element substrate 100C also includes an internal space (a measurement target gas flow portion 7C) into which the measurement target gas is introduced at one leading end portion of the element substrate 100C, between the lower face of the second solid electrolyte layer 6 and the upper face of the first solid electrolyte layer 4.

The configuration of the measurement target gas flow portion 7C is the same as the configuration of the internal space (the measurement target gas flow portion 7) included in the element substrate 100, from the gas inlet 10 to the second internal cavity 17. Meanwhile, the element substrate 100C additionally includes a fourth diffusion control portion 18 and the third internal cavity 19. Specifically, the measurement target gas flow portion 7C is constituted by the gas inlet 10, the first diffusion control portion 11, the buffer space 12, the second diffusion control portion 13, the first internal cavity 15, the third diffusion control portion 16, the second internal cavity 17, the fourth diffusion control portion 18, and the third internal cavity 19, which are adjacent and connected to each other in this order. That is, the measurement target gas flow portion 7C has a three-chamber structure (the first internal cavity 15, the second internal cavity 17, and the third internal cavity 19), and is a portion (internal space) from the gas inlet 10 to the third internal cavity 19. The measurement target gas flow portion 7C is provided by hollowing out a portion of the spacer layer 5. An upper portion of the measurement target gas flow portion 7C is demarcated by the lower face of the second solid electrolyte layer 6. A lower portion of the measurement target gas flow portion 7C is demarcated by the upper face of the first solid electrolyte layer 4. Side portions of the measurement target gas flow portion 7C are demarcated by the side faces of the spacer layer 5.

The gas inlet 10, the first diffusion control portion 11, the buffer space 12, the second diffusion control portion 13, the first internal cavity 15, the third diffusion control portion 16, and the second internal cavity 17 included in the measurement target gas flow portion 7C are the same as those included in the measurement target gas flow portion 7, and a description thereof is omitted.

The fourth diffusion control portion 18 is a member (portion) that applies predetermined diffusion resistance to the measurement target gas. In the example shown in FIG. 7, the fourth diffusion control portion 18 forms a hole (a flow path through which the measurement target gas flows) whose length in a direction perpendicular to the drawing is shorter than that of the third internal cavity 19. Specifically, the fourth diffusion control portion 18 forms one slit that is laterally elongated (i.e. has an opening whose lengthwise direction is perpendicular to the drawing) formed as a gap between the fourth diffusion control portion 18 and the lower face of the second solid electrolyte layer 6. That is, the fourth diffusion control portion 18 is in contact with the upper face of the first solid electrolyte layer 4. For example, the fourth diffusion control portion 18 serves as a bridging portion (fourth bridging portion) that bridges the hollowed space in the spacer layer 5, and the space between the fourth diffusion control portion 18 and the layer 6 serves as a slit, i.e. the flow path CH through which the measurement target gas flows. Meanwhile, the fourth diffusion control portion 18 may form two laterally elongated slits (i.e. have openings whose lengthwise direction is perpendicular to the drawing), similarly to the first diffusion control portion 11, the second diffusion control portion 13, and the third diffusion control portion 16. That is, the fourth diffusion control portion 18 need not be in contact with the upper face of the first solid electrolyte layer 4. The fourth diffusion control portion 18 need only be capable of applying predetermined diffusion resistance to the measurement target gas flowing from the second internal cavity 17 to the third internal cavity 19, and forming a flow path of the measurement target gas from the second internal cavity 17 to the third internal cavity 19.

As mentioned above, the fourth diffusion control portion 18 is a portion that applies predetermined diffusion resistance to the measurement target gas whose oxygen concentration (oxygen partial pressure) has been controlled by operation of the auxiliary pump cell 50 in the second internal cavity 17, and guides this measurement target gas to the third internal cavity 19.

The third internal cavity 19 is provided as a space for performing processing regarding measurement of the concentration of nitrogen oxide ($NO_x$) in the measurement target gas that was introduced via the fourth diffusion control portion 18. The $NO_x$ concentration is measured by operation of the measurement pump cell 41. In the element substrate 100C, the oxygen concentration (oxygen partial pressure) is pre-adjusted in the first internal cavity 15. Then, in the second internal cavity 17, the measurement target gas introduced through the flow path formed by the third diffusion control portion 16 is subjected to a further adjustment of the oxygen partial pressure by the auxiliary pump cell 50. This allows the oxygen concentration of the measurement target gas introduced from the second internal cavity 17 to the third internal cavity 19 to be kept constant with high accuracy. Accordingly, the element substrate 100C can measure the $NO_x$ concentration with high accuracy.

The measurement pump cell 41 in the element substrate 100C is the same as the measurement pump cell 41 in the element substrate 100 except that the nitrogen oxide concentration in the measurement target gas is measured in the third internal cavity 19, instead of the second internal cavity 17. That is, the measurement target gas whose oxygen concentration has been adjusted in the second internal cavity 17 is subjected to measurement of the $NO_x$ concentration by operation of the measurement pump cell 41. The measurement pump cell 41 is an electro-chemical pump cell constituted by the measurement electrode 44, the external pump electrode 23, the second solid electrolyte layer 6, the spacer layer 5, and the first solid electrolyte layer 4. In one example in FIG. 7, the measurement electrode 44 is provided on the upper face of the first solid electrolyte layer 4 that adjoins (faces) the third internal cavity 19. The measurement electrode 44 is surrounded by the porous diffusion layer 91.

The measurement electrode 44 in the element substrate 100C is the same as the measurement electrode 44 in the element substrate 100. Meanwhile, the measurement electrode 44 in the element substrate 100C also functions as a $NO_x$ reduction catalyst that reduces $NO_x$ present in the atmosphere in the third internal cavity 19.

As described with reference to FIG. 7, the gas sensor element 101 may include a diffusion control portion (the fourth diffusion control portion 18) that applies predetermined diffusion resistance to the measurement target gas in the internal space (the measurement target gas flow portion 7C) into which the measurement target gas is introduced from the gas inlet 10. In this case, the measurement electrode 44 is disposed in an internal cavity (the third internal cavity 19) that is demarcated by the fourth diffusion control portion 18 on the upstream side in the flow direction of the measurement target gas. The third internal cavity 19 is a cavity into which the measurement target gas is introduced from the second internal cavity 17 through the flow path (slit) formed by the fourth diffusion control portion 18. The second internal cavity 17 is a cavity in which the auxiliary pump cell 50 capable of adjusting the oxygen partial pressure in the measurement target gas is disposed, i.e. a cavity through which oxygen is pumped out to or pumped in from the external space. That is, the measurement electrode 44 is disposed in the third internal cavity 19 into which the measurement target gas is introduced through the flow path (slit) formed by the fourth diffusion control portion 18, from the second internal cavity 17 in which the auxiliary pump cell 50 is disposed. This configuration enables the gas sensor element 101 to achieve the following effects. That is, the gas sensor element 101 can bring the diffusion mode of $NO_x$ gas reaching the measurement electrode 44 closer to a mode of diffusing while repeatedly colliding with a wall face of a sufficiently narrow flow path, as in Knudsen diffusion, than in the case where the fourth diffusion control portion 18 is not provided.

Example where Leading End Protection Layer has Multi-Layer Structure

The leading end protection layer 200 illustrated in FIG. 1 has a constant porosity throughout. However, it is not essential that the leading end protection layer of the gas sensor element 101 has a porosity that is constant throughout. The leading end protection layer of the gas sensor element 101 may alternatively have a multi-layer structure; for example, the leading end protection layer may include a plurality of layers with different porosities. An example where the leading end protection layer of the gas sensor element 101 has a multi-layer structure will be described below with reference to FIG. 8.

Figure 8:
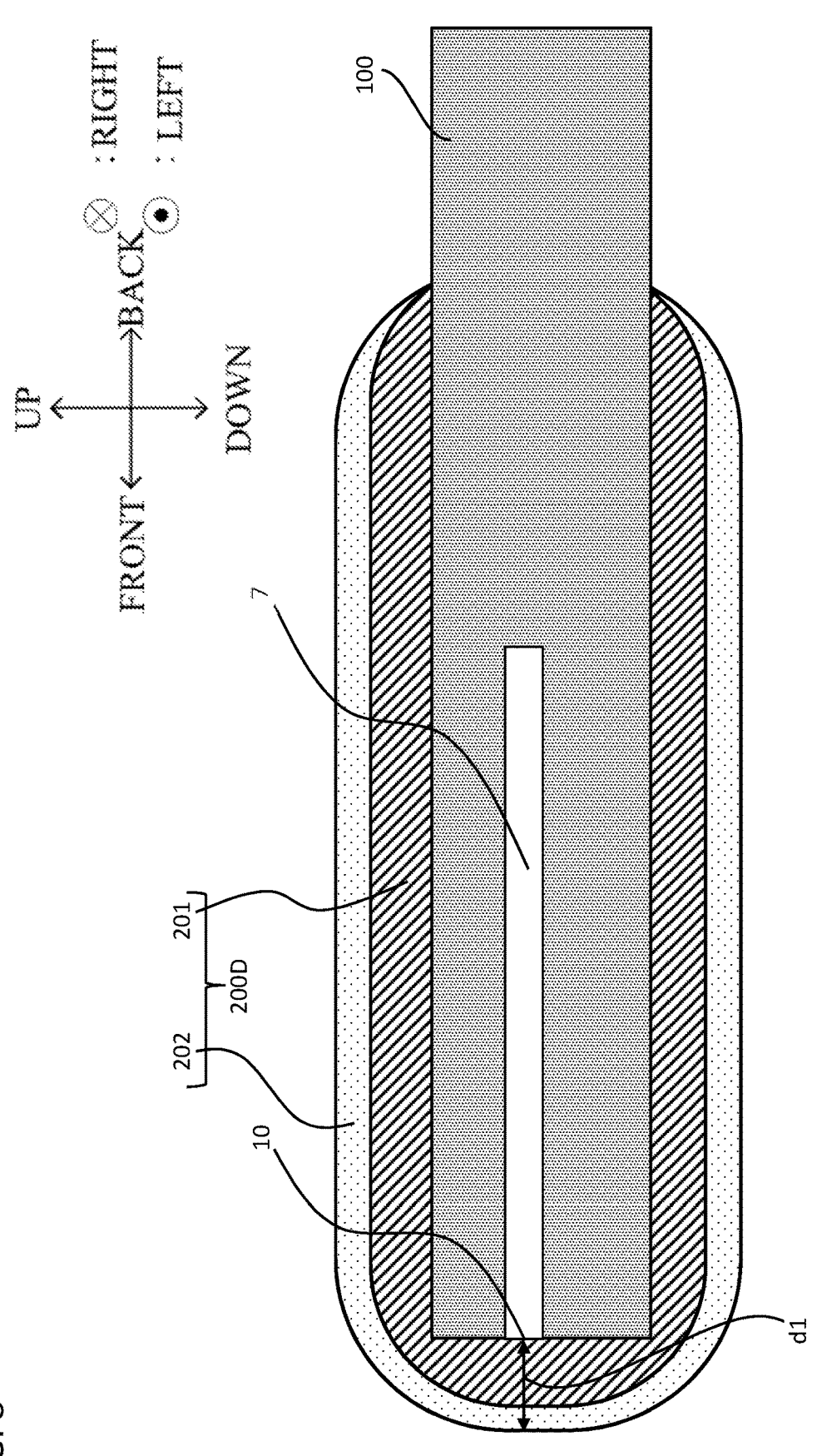
FIG. 8 is a cross-sectional schematic view that schematically shows an example of a configuration of a sensor element that includes a leading end protection layer according to a variation.

FIG. 8 is a cross-sectional schematic view that schematically shows an example of a configuration of the gas sensor element 101 that includes a leading end protection layer 200D according to a variation. Specifically, FIG. 8 shows an example of the leading end protection layer 200D that includes an internal leading end protection layer 201 and an external leading end protection layer 202, which have different porosities. The gas sensor element 101 may have the leading end protection layer 200D illustrated in FIG. 8 that includes the internal leading end protection layer 201 and the external leading end protection layer 202, instead of the leading end protection layer 200 illustrated in FIG. 1.

The leading end protection layer 200D covers at least the face of the element substrate 100 in which the gas inlet 10 is open (i.e. the leading end face of the element substrate 100). In the example shown in FIG. 8, the leading end protection layer 200D covers the leading end face of the element substrate 100 and four side faces of the element substrate 100 that are continuous with the leading end face.

The leading end protection layer 200D includes at least the internal leading end protection layer 201 and the external leading end protection layer 202. The internal leading end protection layer 201 is in contact with the face of the element substrate 100 in which the gas inlet 10 is open. The external leading end protection layer 202 constitutes the outermost face of the leading end protection layer 200D. The porosity of the internal leading end protection layer 201 is larger than the porosity of the external leading end protection layer 202, and the thickness of the internal leading end protection layer 201 is 30% or more and 90% or less of the thickness of the leading end protection layer 200D. That is, the leading end protection layer 200D includes the internal leading end protection layer 201 and the external leading end protection layer 202, with the porosity of the internal leading end protection layer 201 being larger than the porosity of the external leading end protection layer 202, and the thickness of the internal leading end protection layer 201 being 30% to 90% of the thickness of the leading end protection layer 200D.

In this configuration, the leading end protection layer 200D includes at least two layers, and the internal layer (e.g. the internal leading end protection layer 201) has a porosity larger than the porosity of the external layer (e.g. the external leading end protection layer 202). The gas sensor element 101 can prevent clogging caused by poisonous substances or the like in the vicinity of the gas inlet 10 and avoid a decrease in $NO_x$ sensitivity, as a result of the porosity of the internal layer (the internal leading end protection layer 201) being larger than the porosity of the external layer (the external leading end protection layer 202).

Particularly, the gas sensor element 101 achieves the following effects due to a large thickness of the internal leading end protection layer 201, which has a porosity larger than the porosity of the external leading end protection layer 202, i.e. due to a high proportion of the thickness of the internal leading end protection layer 201 to the thickness of the leading end protection layer 200. That is, ensuring a sufficient thickness of the internal leading end protection layer 201 having a large porosity prevents clogging caused by poisonous substances or the like in the vicinity of the gas inlet 10, and particularly, reduces the likelihood of clogging in the layer closer to the gas inlet 10 (i.e. the internal leading end protection layer 201). Specifically, the internal leading end protection layer 201 in contact with the gas inlet 10 can be prevented from being clogged with poisonous substances or the like by setting the proportion of the thickness of the internal leading end protection layer 201 having a large porosity to the thickness of the leading end protection layer 200 to 30% to 90%.

Like the leading end protection layer 200, the leading end protection layer 200D has a predetermined thickness; specifically, the distance d1 from the outermost face of the leading end protection layer 200D to the gas inlet 10 is 0.2 mm or more. That is, in the example shown in FIG. 8, the distance d1 from the outermost face of the external leading end protection layer 202 to the gas inlet 10 is 0.2 mm or more. The following effects can be achieved as a result of the distance d1 from the outermost face of the leading end protection layer 200D to the gas inlet 10 being sufficiently long (specifically, 0.2 mm or more), i.e. the leading end protection layer 200D being sufficiently thick. That is, even in a harsh environment with a large amount of poisonous substances or the like, the poisonous substances or the like can be reliably trapped (captured) in the leading end protection layer 200D to prevent clogging caused by poisonous substances or the like in the vicinity of the gas inlet 10 and prevent a decrease in $NO_x$ sensitivity.

The leading end protection layer 200D illustrated in FIG. 8 includes the internal leading end protection layer 201 and the external leading end protection layer 202, i.e. has a two-layer structure. Note that it is not essential that the leading end protection layer 200D has a two-layer structure, and the leading end protection layer 200D may alternatively include three or more layers. That is, the leading end protection layer 200D may include yet another layer in addition to the internal leading end protection layer 201 and the external leading end protection layer 202, e.g. may have a three-layer structure, or a multi-layer structure with four or more layers. The leading end protection layer 200D need only include at least the internal leading end protection layer 201 that is in contact with the face of the element substrate 100 in which the gas inlet 10 is open, and the external leading end protection layer 202 that constitutes the outermost face of the leading end protection layer 200D, and may additionally include yet another layer therebetween. The leading end protection layer 200D need only be such that the porosity of the internal leading end protection layer 201 is larger than the porosity of the external leading end protection layer 202, and the thickness of the internal leading end protection layer 201 is 30% or more and 90% or less of the thickness of the leading end protection layer 200D.

Features

As described above, the gas sensor element 101 according to the present embodiment includes the element substrate 100 (or 100C), the leading end protection layer 200 (or 200D), the measurement electrode 44, and the porous diffusion layer 91 (or either 91A or 91B). For example, the element substrate 100 includes the measurement target gas flow portion 7 serving as an internal space, and the measurement target gas is introduced into the measurement target gas flow portion 7 from the gas inlet 10, which is open in the surface of the element substrate 100. For example, the leading end protection layer 200 covers at least the face of the element substrate 100 in which the gas inlet 10 is open. The measurement electrode 44 is provided in the measurement target gas flow portion 7 and contains at least either silica or alumina. For example, the porous diffusion layer 91 covers the measurement electrode 44 and has a porosity that is 5% or more and 25% or less and is lower than the porosity of the leading end protection layer 200. In the porous diffusion layer 91A that includes a plurality of faces (layers) with different porosities, the average porosity of the porous diffusion layer 91A is 5% or more and 25% or less, and is lower than the porosity of the leading end protection layer 200.

In this configuration, the porous diffusion layer 91 is located around the measurement electrode 44. Specifically, the measurement electrode 44 is covered by the porous diffusion layer 91 whose porosity is 5% or more and 25% or less and is lower than the porosity of the leading end protection layer 200. The porous diffusion layer 91 covering the measurement electrode 44 enables the diffusion mode around the measurement electrode 44 to be changed to a mode of diffusing while repeatedly colliding with a wall face of a sufficiently narrow flow path, as in Knudsen diffusion. Thus, even if $H_2O$ gas is present in the measurement target gas, the gas sensor element 101 can reduce the impact of $H_2O$ gas on $NO_x$ gas (and $O_2$ gas) by means of the porous diffusion layer 91 covering the measurement electrode 44. Specifically, the gas sensor element 101 can suppress fluctuations in $NO_x$ output and the degradation of the measurement electrode 44, which are considered to be caused by molecular diffusion of $NO_x$ under high $H_2O$ concentration, by means of the porous diffusion layer 91 covering the measurement electrode 44.

Here, if the porous diffusion layer 91 having large diffusion resistance is located around the measurement electrode 44, there is a possibility that the porous diffusion layer 91 will be clogged with poisonous substances or the like. The gas sensor element 101 includes the leading end protection layer 200 that covers at least the face (leading end face) of the element substrate 100 in which the gas inlet 10 is open. This enables the gas sensor element 101 to trap poisonous substances or the like by means of the leading end protection layer 200, i.e. capture poisonous substances or the like by means of the leading end protection layer 200.

Particularly, in the gas sensor element 101, the porosity of the leading end protection layer 200 is higher (larger) than the porosity of the porous diffusion layer 91 (91A, 91B) that surrounds the measurement electrode 44. The gas sensor element 101 can avoid a situation where the leading end protection layer 200 is clogged with poisonous substances or the like, resulting in a decrease in $NO_x$ output, as a result of the porosity of the leading end protection layer 200 being higher than the porosity of the porous diffusion layer 91.

The measurement electrode 44 of the gas sensor element 101 contains at least either silica or alumina. Here, when $NO_x$ is measured at a high temperature (e.g. 700 to 800 degrees Celsius), the measurement electrode 44 constantly repeats expansion and contraction. Even in such an environment, the gas sensor element 101 can achieve the following effects as a result of the measurement electrode 44 containing at least either silica or alumina. That is, the gas sensor element 101 can suppress the expansion and contraction of the measurement electrode 44. That is, the gas sensor element 101 can prevent cracks, splitting, or the like from occurring in the porous diffusion layer 91 that covers the measurement electrode 44, and prevent the measurement electrode 44 from peeling away from the element substrate 100.

The gas sensor according to one aspect of the present invention may measure the amount of a specific gas component in the measurement target gas, i.e. the concentration of a specific gas component, using the gas sensor element 101. This gas sensor changes the diffusion mode of $NO_x$ that reaches the measurement electrode 44 from molecular diffusion to a mode of diffusing while repeatedly colliding with a wall face of a sufficiently narrow flow path. Thus, the gas sensor suppresses fluctuations in $NO_x$ output and the deterioration of the measurement electrode 44, which are considered to be caused by molecular diffusion of $NO_x$ under high $H_2O$ concentration, by means of the porous diffusion layer 91 (91A, 91B) covering the measurement electrode 44.

Variations

Although an embodiment of the present invention has been described above, the description of the above embodiment is merely an illustration of the invention in all respects. Various improvements and variations may be made to the above embodiment. The constituent elements of the above embodiment may be omitted, replaced, and added as appropriate. The shape and dimensions of each constituent element of the above embodiment may be changed as appropriate, according to the mode of implementation. For example, the following changes are possible. Note that, in the following, the same constituent elements as those of the above embodiment are assigned the same reference numerals, and the description of the same features as the above embodiment is omitted as appropriate. The following variations can be combined as appropriate.

Variation 1

Although an example has been described where the measurement electrode 44 is disposed on the upper face of the first solid electrolyte layer 4, it is not essential for the gas sensor element 101 that the measurement electrode 44 is disposed on the upper face of the first solid electrolyte layer 4. For example, the measurement electrode 44 may alternatively be located on the lower face of the second solid electrolyte layer 6.

Variation 2

The above description has been given of an example where the measurement electrode 44 is disposed in the internal cavity (e.g. the second internal cavity 17 or the third internal cavity 19) in which a diffusion control portion (e.g. the third diffusion control portion 16 or the fourth diffusion control portion 18) is provided on the upstream side. However, it is not essential that the measurement electrode 44 is disposed in the internal cavity in which a diffusion control portion is provided on the upstream side. It is not essential, either, that the gas sensor element 101 includes a plurality of internal cavities (e.g. two or three cavities). For example, the gas sensor element 101 may alternatively have a one-cavity structure. That is, it is not essential for the gas sensor element 101 to include the diffusion control portion (at least one of the first diffusion control portion 11, the second diffusion control portion 13, the third diffusion control portion 16, and the fourth diffusion control portion 18). The gas sensor element 101 need only have the porous diffusion layer (the porous diffusion layer 91, 91A, or 91B) covering the measurement electrode 44, and the leading end protection layer (either the leading end protection layer 200 or 200D) covering at least the face of the element substrate 100 in which the gas inlet 10 is open. The location of the measurement electrode 44 in the gas sensor element 101 can be selected as appropriate, according to the usage status or the like.

EXAMPLES

As described above, the gas sensor element 101 achieves the following effects as a result of including the porous diffusion layer (91, 91A, or 91B) covering the measurement electrode 44, and the leading end protection layer (200 or 200D) covering at least the face of the element substrate 100 in which the gas inlet 10 is open. That is, the gas sensor element 101 can suppress the deterioration of the measurement electrode 44 in an environment with high $H_2O$ concentration and improve the durability, by means of the porous diffusion layer 91. Further, the gas sensor element 101 can, for example, prevent the porous diffusion layer 91 from being clogged with poisonous substances or the like and maintain the measurement accuracy over a long period of time, by means of the leading end protection layer 200.

The inventors produced gas sensors according to the following examples and comparative examples, and conducted various tests to verify the above-described effects. Note that the present invention is not limited to the following examples.

TABLE 1

| Criteria | Distance between measurement electrode and porous diffusion layer [mm] | Average porosity of porous diffusion layer [%] | Porosity of surface of porous diffusion layer [%] | Porosity on electrode side of porous diffusion layer [%] | Difference in porosity porous diffusion layer [%] | With/without leading end protection layer | Porosity of leading end protection layer [%] | Porosity of internal protection layer [%] | Shortest distance between protection layer and gas inlet [mm] |
|---|---|---|---|---|---|---|---|---|---|
| Example 1 | 0.1 | 12 | 12 | 12 | 0 | With | 20 | — | 300 |
| Example 2 | 0.0 | 8 | 6 | 10 | 4 | With | 25 | — | 280 |
| Example 3 | 0.0 | 12 | 8 | 18 | 10 | With | 20 | 60 | 1020 |
| Example 4 | 0.0 | 25 | 20 | 30 | 10 | With | 20 | 60 | 1000 |
| Example 5 | 0.0 | 15 | 10 | 20 | 10 | With | 25 | 65 | 990 |
| Example 6 | 0.0 | 10 | 7 | 15 | 8 | With | 15 | 50 | 1050 |
| Example 7 | 0.1 | 15 | 8 | 18 | 10 | With | 23 | 55 | 500 |
| Example 8 | 0.13 | 20 | 17 | 22 | 5 | With | 30 | — | 200 |
| Example 9 | 0.1 | 25 | 25 | 25 | 0 | With | 15 | 45 | 900 |
| Example 10 | 0.15 | 10 | 12 | 10 | −2 | With | 20 | — | 300 |
| Example 11 | 0.1 | 10 | 7 | 12 | 5 | With | 20 | — | 100 |
| Example 12 | 0.2 | 15 | 12 | 14 | 2 | With | 25 | — | 300 |
| Example 13 | 0.0 | 11 | 15 | 6 | −9 | With | 25 | — | 280 |
| Comparative Example 1 | 0.0 | 10 | 6 | 12 | 6 | Without | — | — | — |
| Comparative Example 2 | — | — | — | — | — | With | 15 | — | 250 |
| Comparative Example 3 | 0.0 | 35 | 30 | 40 | 10 | With | 30 | — | 280 |

| Criteria | Thickness of external protection layer [um] | Thickness of internal protection layer [um] | Proportion of internal protection laye [%] | Evaluation 1 | Evaluation 2 | Evaluation 3 | Evaluation 4 | Evaluation 5 |
|---|---|---|---|---|---|---|---|---|
| Example 1 | 300 | — | — | B | B | A | B | A |
| Example 2 | 280 | — | — | A | A | A | B | B |
| Example 3 | 280 | 740 | 73 | A | A | A | A | A |
| Example 4 | 300 | 700 | 70 | A | A | A | A | A |
| Example 5 | 360 | 630 | 64 | A | A | A | A | A |
| Example 6 | 200 | 850 | 81 | A | A | A | A | B |
| Example 7 | 350 | 150 | 30 | A | A | A | A | A |
| Example 8 | 200 | — | — | A | A | B | B | A |
| Example 9 | 300 | 600 | 67 | B | B | A | B | A |
| Example 10 | 300 | — | — | B | B | A | B | A |
| Example 11 | 100 | — | — | A | A | B | F | A |
| Example 12 | 300 | — | — | B | B | A | B | A |
| Example 13 | 280 | — | — | A | A | A | B | C |
| Comparative Example 1 | — | — | — | A | A | F | — | B |
| Comparative Example 2 | 250 | — | — | F | F | A | A | A |
| Comparative Example 3 | 280 | — | — | F | F | A | B | A |

Table 1 shows the configurations of each gas sensor element and the test results of evaluations 1 to 5 for gas sensors that include gas sensor elements according to examples 1 to 13 and comparative examples 1 to 3. In the following description, there are cases where the gas sensors that include the gas sensor elements according to the examples 1 to 13 and the comparative examples 1 to 3 are abbreviated as gas sensors (NO$_x$ sensors) according to the examples 1 to 13 and the comparative examples 1 to 3.

Details of Examples 1 to 13 and Comparative
Examples 1 to 3

The example 1 is a gas sensor that includes the gas sensor element 101 that has the leading end protection layer 200 illustrated in FIG. 1 and the porous diffusion layer 91B illustrated in FIG. 6. Specifically, a space (gap) is present between the measurement electrode 44 and the porous diffusion layer 91B, and the distance d2 therebetween is 0.1 mm, namely 0.15 mm or less. In the gas sensor according to the example 1, the porous diffusion layer 91B is a porous layer having a porosity that is constant at 5% or more and 25% or less throughout; specifically, the porosity of the porous diffusion layer 91B is 12%. Also, the porosity of the surface (the external face facing the measurement target gas flow portion 7) of the porous diffusion layer 91B and the porosity of the face on the electrode side (the internal face opposing the measurement electrode 44; the face facing the measurement electrode 44) are both 12%, and the porosity difference therebetween is 0%. That is, the external face and the internal face of the porous diffusion layer 91B in the thickness direction both have a porosity of 12%. The gas sensor according to the example 1 has the leading end protection layer 200 ('with' in the table), and the leading end protection layer 200 does not include the internal leading end protection layer 201; i.e. the leading end protection layer 200 has a porosity that is constant throughout. Specifically, the porosity of the leading end protection layer 200 is 20%, which is higher than the porosity of the porous diffusion layer 91B. That is, in the gas sensor according to the example 1, the porosity (12%) of the porous diffusion layer 91B is lower than the porosity (20%) of the leading end protection layer 200. Further, the shortest distance (d1) between the leading end protection layer 200 and the gas inlet 10, i.e. the distance d1 from the outermost face of the leading end protection layer 200 to the gas inlet 10 is 300 μm, namely 200 μm (0.2 mm) or more. In the gas sensor according to the example 1, the leading end protection layer 200 does not include the internal leading end protection layer 201, as mentioned above. Thus, the thickness of the external leading end protection layer 202 is the same as the distance d1 from the outermost face of the leading end protection layer 200 to the gas inlet 10, namely 300 μm. The porosity of the internal leading end protection layer 201, the thickness of the internal leading end protection layer 201, and the thickness proportion of the internal leading end protection layer 201 are all '‑' in the table.

The example 2 is a gas sensor that includes the gas sensor element 101 that has the leading end protection layer 200 illustrated in FIG. 1 and the porous diffusion layer 91A illustrated in FIG. 5. Specifically, in the example 2, no space (gap) is present between the measurement electrode 44 and the porous diffusion layer 91A, and the distance d2 therebetween is 0 mm, unlike the example 1. Meanwhile, in the example 2, the distance d2 between the measurement electrode 44 and the porous diffusion layer 91A is 0.15 mm or less, like the example 1. In the gas sensor according to the example 2, the porous diffusion layer 91A has different porosities between the surface (the external face facing the measurement target gas flow portion 7) and the face on the electrode side (the internal face opposing the measurement electrode 44; the face facing (in contact with) the measurement electrode 44). Specifically, in the gas sensor according to the example 2, the porosity of the surface of the porous diffusion layer 91A is 6%, and the porosity of the face on the electrode side is 10%. That is, in the gas sensor of the example 2, the porosity (10%) of the internal face (the face on the electrode side) of the porous diffusion layer 91A that opposes the measurement electrode 44 is higher than the porosity (6%) of the external face (surface). Meanwhile, the difference therebetween is less than 10% (specifically, 4%); i.e. the porosity (10%) of the internal face of the porous diffusion layer 91A that opposes the measurement electrode 44 is 4% higher than the porosity (6%) of the external face. In the example 2, the porosity of the internal face (10%) opposing the measurement electrode 44, of the two faces of the porous diffusion layer 91A in the thickness direction, is higher than the porosity (6%) of the external face, specifically by 4% higher. The average porosity of the porous diffusion layer 91A is 8%, namely 5% or more and 25% or less. The gas sensor according to the example 2 has the leading end protection layer 200 ('with' in the table), and the leading end protection layer 200 does not include the internal leading end protection layer 201; i.e. the porosity of the leading end protection layer 200 is constant throughout. Specifically, the porosity of the leading end protection layer 200 is 25%, which is higher than the porosity (average porosity) of the porous diffusion layer 91A. In other words, in the gas sensor according to the example 2, the porosity (average porosity) (8%) of the porous diffusion layer 91A is lower than the porosity (25%) of the leading end protection layer 200. The shortest distance (d1) between the leading end protection layer 200 and the gas inlet 10, i.e. the distance d1 from the outermost face of the leading end protection layer 200 to the gas inlet 10 is 280 μm, namely 200 μm (0.2 mm) or more. As mentioned above, in the gas sensor according to the example 2, the leading end protection layer 200 does not include the internal leading end protection layer 201, and therefore, the thickness of the external leading end protection layer 202 is the same as the distance d1 from the outermost face of the leading end protection layer 200 to the gas inlet 10, i.e. 280 μm. The porosity of the internal leading end protection layer 201, the thickness of the internal leading end protection layer 201, and the thickness proportion of the internal leading end protection layer 201 are all '‑' in the table.

The example 3 is a gas sensor that includes the gas sensor element 101 that has the leading end protection layer 200D illustrated in FIG. 8 and the porous diffusion layer 91A illustrated in FIG. 5. Specifically, no space (gap) is present between the measurement electrode 44 and the porous diffusion layer 91A, and the distance d2 therebetween is 0 mm. Meanwhile, in the example 3, the distance d2 between the measurement electrode 44 and the porous diffusion layer 91A is 0.15 mm or less, like the example 1 and 2. In the gas sensor according to the example 3, the porous diffusion layer 91A has different porosities between the surface (the external face facing the measurement target gas flow portion 7) and the face on the electrode side (the internal face opposing the measurement electrode 44; the face facing (in contact with) the measurement electrode 44). Specifically, in the gas sensor according to the example 3, the surface of the porous diffusion layer 91A has a porosity of 8%, and the face on the electrode side has a porosity of 18%. In other words, in the gas sensor of the example 3, the internal face of the porous diffusion layer 91A (the face thereof on the electrode side) that opposes the measurement electrode 44 has a porosity (18%) higher than the porosity (8%) of the external face (surface). Further, unlike the example 2, the difference between the porosity (18%) of the internal face of the porous diffusion layer 91A that opposes the measurement electrode 44 and the porosity (8%) of the external face is 10% or more (specifically, 10%). The average porosity of the porous diffusion layer 91A is 12%, namely 5% or more and 25% or less. The gas sensor according to the example 3 has the leading end protection layer 200D ('with' in the table). Further, unlike the examples 1 and 2, the leading end protection layer 200D includes the internal leading end protection layer 201. Specifically, the porosity (average porosity) of the leading end protection layer 200D is 20%, which is higher than the porosity (average porosity) of the porous diffusion layer 91A. In other words, in the gas sensor according to the example 3, the porosity (average porosity) (12%) of the porous diffusion layer 91A is lower than the porosity (average porosity) (20%) of the leading end protection layer 200D. The internal leading end protection layer 201 included in the leading end protection layer 200D has a porosity of 60%. The shortest distance (d1) between the leading end protection layer 200D and the gas inlet 10, i.e. the distance d1 from the outermost face of the leading end protection layer 200D to the gas inlet 10 is 1020 μm, namely 200 μm (0.2 mm) or more. The external leading end protection layer 202 included in the leading end protection layer 200D has a thickness of 280 μm, and the internal leading end protection layer 201 included in the leading end protection layer 200D has a thickness of 740 μm. Hence, the thickness proportion of the internal leading end protection layer 201, i.e. the proportion of the thickness of the internal leading end protection layer 201 to the thickness of the leading end protection layer 200D is 73%, namely 30% or more and 90% or less.

The example 4 is a gas sensor that includes the gas sensor element 101 that has the leading end protection layer 200D illustrated in FIG. 8 and the porous diffusion layer 91A illustrated in FIG. 5. Specifically, no space (gap) is present between the measurement electrode 44 and the porous diffusion layer 91A, and the distance d2 therebetween is 0 mm. Meanwhile, in the example 4, the distance d2 between the measurement electrode 44 and the porous diffusion layer 91A is 0.15 mm or less, like the examples 1 to 3. In the gas sensor according to the example 4, the porous diffusion layer 91A has different porosities between the surface (the external face facing the measurement target gas flow portion 7) and the face on the electrode side (the internal face opposing the measurement electrode 44; the face facing (in contact with) the measurement electrode 44). Specifically, in the gas sensor according to the example 4, the surface of the porous diffusion layer 91A has a porosity of 20%, and the face on the electrode side has a porosity of 30%. In other words, in the gas sensor of the example 4, the internal face of the porous diffusion layer 91A (the face on the electrode side) that opposes the measurement electrode 44 has a porosity (30%) higher than the porosity (20%) of the external face (surface). Further, unlike the example 2, the difference between the porosity (30%) of the internal face of the porous diffusion layer 91A that opposes the measurement electrode 44 and the porosity (20%) of the external face is 10% or more (specifically, 10%). The average porosity of the porous diffusion layer 91A is 25%, namely 5% or more and 25% or less. The gas sensor according to the example 4 has the leading end protection layer 200D ('with' in the table).

Further, unlike the examples 1 and 2, the leading end protection layer 200D includes the internal leading end protection layer 201. Specifically, the porosity (average porosity) of the leading end protection layer 200D is 20%, which is lower than the porosity (average porosity) of the porous diffusion layer 91A, unlike the example 3. In other words, in the gas sensor according to the example 4, the porosity (average porosity) (25%) of the porous diffusion layer 91A is higher than the porosity (average porosity) (20%) of the leading end protection layer 200D, unlike the example 3. Meanwhile, the porosity of the internal leading end protection layer 201 included in the leading end protection layer 200D is 60%, which is higher than the porosity (average porosity) (25%) of the porous diffusion layer 91A. The shortest distance (d1) between the leading end protection layer 200D and the gas inlet 10, i.e. the distance d1 from the outermost face of the leading end protection layer 200D to the gas inlet 10 is 1000 μm, namely 200 μm (0.2 mm) or more. The thickness of the external leading end protection layer 202 included in the leading end protection layer 200D is 300 μm, and the thickness of the internal leading end protection layer 201 included in the leading end protection layer 200D is 700 μm. Hence, the thickness proportion of the internal leading end protection layer 201, i.e. the proportion of the thickness of the internal leading end protection layer 201 to the thickness of the leading end protection layer 200D is 70%, namely 30% or more and 90% or less.

The example 5 is a gas sensor that includes the gas sensor element 101 that has the leading end protection layer 200D illustrated in FIG. 8 and the porous diffusion layer 91A illustrated in FIG. 5. Specifically, no space (gap) is present between the measurement electrode 44 and the porous diffusion layer 91A, and the distance d2 therebetween is 0 mm. Meanwhile, in the example 5, the distance d2 between the measurement electrode 44 and the porous diffusion layer 91A is 0.15 mm or less, like the examples 1 to 4. In the gas sensor according to the example 5, the porous diffusion layer 91A has different porosities between the surface (the external face facing the measurement target gas flow portion 7) and the face on the electrode side (the internal face opposing the measurement electrode 44; the face facing (in contact with) the measurement electrode 44). Specifically, in the gas sensor according to the example 5, the surface of the porous diffusion layer 91A has a porosity of 10%, and the face on the electrode side has a porosity of 20%. In other words, in the gas sensor of the example 5, the internal face of the porous diffusion layer 91A (the face on the electrode side) that opposes the measurement electrode 44 has a porosity (20%) higher than the porosity (10%) of the external face (surface). Further, unlike the example 2, the difference between the porosity (20%) of the internal face of the porous diffusion layer 91A that opposes the measurement electrode 44 and the porosity (10%) of the external face is 10% or more (specifically, 10%). The average porosity of the porous diffusion layer 91A is 15%, namely 5% or more and 25% or less. The gas sensor according to the example 5 has the leading end protection layer 200D ('with' in the table). Further, unlike the examples 1 and 2, the leading end protection layer 200D includes the internal leading end protection layer 201. Specifically, the porosity (average porosity) of the leading end protection layer 200D is 25%, which is higher than the porosity (average porosity) of the porous diffusion layer 91A. In other words, in the gas sensor according to the example 5, the porosity (average porosity) (15%) of the porous diffusion layer 91A is lower than the porosity (average porosity) (25%) of the leading end protection layer 200D. The internal leading end protection layer

201 included in the leading end protection layer 200D has a porosity of 65%. The shortest distance (d1) between the leading end protection layer 200D and the gas inlet 10, i.e. the distance d1 from the outermost face of the leading end protection layer 200D to the gas inlet 10 is 990 μm, namely 200 μm (0.2 mm) or more. The thickness of the external leading end protection layer 202 included in the leading end protection layer 200D is 360 μm, and the thickness of the internal leading end protection layer 201 included in the leading end protection layer 200D is 630 μm. Hence, the thickness proportion of the internal leading end protection layer 201, i.e. the proportion of the thickness of the internal leading end protection layer 201 to the thickness of the leading end protection layer 200D is 64%, namely 30% or more and 90% or less.

The example 6 is a gas sensor that includes the gas sensor element 101 that has the leading end protection layer 200D illustrated in FIG. 8 and the porous diffusion layer 91A illustrated in FIG. 5. Specifically, no space (gap) is present between the measurement electrode 44 and the porous diffusion layer 91A, and the distance d2 therebetween is 0 mm. Meanwhile, in the example 6, the distance d2 between the measurement electrode 44 and the porous diffusion layer 91A is 0.15 mm or less, like the examples 1 to 5. In the gas sensor according to the example 6, the porous diffusion layer 91A has different porosities between the surface (the external face facing the measurement target gas flow portion 7) and the face on the electrode side (the internal face opposing the measurement electrode 44; the face facing (in contact with) the measurement electrode 44). Specifically, in the gas sensor according to the example 6, the surface of the porous diffusion layer 91A has a porosity of 7%, and the face on the electrode side has a porosity of 15%. In other words, in the gas sensor of the example 6, the internal face of the porous diffusion layer 91A (the face on the electrode side) that opposes the measurement electrode 44 has a porosity (15%) higher than the porosity (7%) of the external face (surface). Meanwhile, unlike the examples 3, 4, and 5, the difference therebetween is less than 10% (specifically, 8%); i.e. the porosity (15%) of the internal face of the porous diffusion layer 91A that opposes the measurement electrode 44 is 8% higher than the porosity (7%) of the external face. The average porosity of the porous diffusion layer 91A is 10%, namely 5% or more and 25% or less. The gas sensor according to the example 6 has the leading end protection layer 200D ('with' in the table). Further, unlike the examples 1 and 2, the leading end protection layer 200D includes the internal leading end protection layer 201. Specifically, the porosity (average porosity) of the leading end protection layer 200D is 15%, which is higher than the porosity (average porosity) of the porous diffusion layer 91A. In other words, in the gas sensor according to the example 6, the porosity (average porosity) (10%) of the porous diffusion layer 91A is lower than the porosity (average porosity) (15%) of the leading end protection layer 200D. The internal leading end protection layer 201 included in the leading end protection layer 200D has a porosity of 50%. The shortest distance (d1) between the leading end protection layer 200D and the gas inlet 10, i.e. the distance d1 from the outermost face of the leading end protection layer 200D to the gas inlet 10 is 1050 μm, namely 200 μm (0.2 mm) or more. The thickness of the external leading end protection layer 202 included in the leading end protection layer 200D is 200 μm, and the thickness of the internal leading end protection layer 201 included in the leading end protection layer 200D is 850 μm. Hence, the thickness proportion of the internal leading end protection layer 201, i.e. the proportion of the thickness of the internal leading end protection layer 201 to the thickness of the leading end protection layer 200D is 81%, namely 30% or more and 90% or less.

The example 7 is a gas sensor that includes the gas sensor element 101 that has the leading end protection layer 200D illustrated in FIG. 8 and the porous diffusion layer 91B illustrated in FIG. 6 (with different porosities between the surface and the face on the electrode side). Specifically, a space (gap) is present between the measurement electrode 44 and the porous diffusion layer 91B, and the distance d2 therebetween is 0.1 mm. Meanwhile, in the example 7, the distance d2 between the measurement electrode 44 and the porous diffusion layer 91B is 0.15 mm or less, like the examples 1 to 6. In the gas sensor according to the example 7, unlike the example 1, the porous diffusion layer 91B has different porosities between the surface (the external face facing the measurement target gas flow portion 7) and the face on the electrode side (the internal face opposing the measurement electrode 44; the face facing the measurement electrode 44). Specifically, in the gas sensor according to the example 7, the porosity of the surface of the porous diffusion layer 91B is 8%, and the porosity of the face on the electrode side is 18%. In other words, in the gas sensor of the example 7, the internal face of the porous diffusion layer 91B (the face on the electrode side) that opposes the measurement electrode 44 has a porosity (18%) higher than the porosity (8%) of the external face (surface), and the difference therebetween is 10% or more (specifically, 10%). The average porosity of the porous diffusion layer 91B is 15%, namely 5% or more and 25% or less. The gas sensor according to the example 7 has the leading end protection layer 200D ('with' in the table). Further, unlike the examples 1 and 2, the leading end protection layer 200D includes the internal leading end protection layer 201. Specifically, the porosity (average porosity) of the leading end protection layer 200D is 23%, which is higher than the porosity (average porosity) of the porous diffusion layer 91B. In other words, in the gas sensor according to the example 7, the porosity (average porosity) (15%) of the porous diffusion layer 91B is lower than the porosity (average porosity) (23%) of the leading end protection layer 200D. The internal leading end protection layer 201 included in the leading end protection layer 200D has a porosity of 55%. Further, the shortest distance (d1) between the leading end protection layer 200D and the gas inlet 10, i.e. the distance d1 from the outermost face of the leading end protection layer 200D to the gas inlet 10 is 500 μm, namely 200 μm (0.2 mm) or more. The thickness of the external leading end protection layer 202 included in the leading end protection layer 200D is 350 μm, and the thickness of the internal leading end protection layer 201 included in the leading end protection layer 200D is 150 μm. Hence, the thickness proportion of the internal leading end protection layer 201, i.e. the proportion of the thickness of the internal leading end protection layer 201 to the thickness of the leading end protection layer 200D is 30%, namely 30% or more and 90% or less.

The example 8 is a gas sensor that includes the gas sensor element 101 that has the leading end protection layer 200 illustrated in FIG. 1 and the porous diffusion layer 91B illustrated in FIG. 6 (with different porosities between the surface and the face on the electrode side). Specifically, a space (gap) is present between the measurement electrode 44 and the porous diffusion layer 91B, and the distance d2 therebetween is 0.13 mm. Meanwhile, in the example 8, the distance d2 between the measurement electrode 44 and the porous diffusion layer 91B is 0.15 mm or less, like the examples 1 to 7. In the gas sensor according to the example 8, unlike the example 1, the porous diffusion layer 91B has different porosities between the surface (the external face facing the measurement target gas flow portion 7) and the face on the electrode side (the internal face opposing the measurement electrode 44; the face facing the measurement electrode 44). Specifically, in the gas sensor according to the example 8, the porosity of the surface of the porous diffusion layer 91B is 17%, and the porosity of the face on the electrode side is 22%. In other words, in the gas sensor of the example 8, the internal face of the porous diffusion layer 91B (the face on the electrode side) that opposes the measurement electrode 44 has a porosity (22%) higher than the porosity (17%) of the external face (surface). Meanwhile, unlike the examples 3, 4, 5, and 7, the difference therebetween is less than 10% (specifically, 5%); i.e. the porosity (22%) of the internal face of the porous diffusion layer 91B that opposes the measurement electrode 44 is 5% higher than the porosity (17%) of the external face. The average porosity of the porous diffusion layer 91B is 20%, namely 5% or more and 25% or less. The gas sensor according to the example 8 includes the leading end protection layer 200 ('with' in the table). Unlike the examples 3 to 7, the leading end protection layer 200 does not include the internal leading end protection layer 201; i.e. the porosity of the leading end protection layer 200 is constant throughout. Specifically, the porosity of the leading end protection layer 200 is 30%, which is higher than the porosity (average porosity) of the porous diffusion layer 91B. That is, in the gas sensor according to the example 8, the porosity (average porosity) (20%) of the porous diffusion layer 91B is lower than the porosity (30%) of the leading end protection layer 200. Further, the shortest distance (d1) between the leading end protection layer 200 and the gas inlet 10, i.e. the distance d1 from the outermost face of the leading end protection layer 200 to the gas inlet 10 is 200 μm, namely 200 μm (0.2 mm) or more. In the gas sensor according to the example 8, the leading end protection layer 200 does not include the internal leading end protection layer 201, as mentioned above. Thus, the thickness of the external leading end protection layer 202 is the same as the distance d1 from the outermost face of the leading end protection layer 200 to the gas inlet 10, namely 200 μm. The porosity of the internal leading end protection layer 201, the thickness of the internal leading end protection layer 201, and the thickness proportion of the internal leading end protection layer 201 are all '-' in the table.

The example 9 is a gas sensor that includes the gas sensor element 101 that has the leading end protection layer 200D illustrated in FIG. 8 and the porous diffusion layer 91B illustrated in FIG. 6. Specifically, a space (gap) is present between the measurement electrode 44 and the porous diffusion layer 91B, and the distance d2 therebetween is 0.1 mm. Meanwhile, in the example 9, the distance d2 between the measurement electrode 44 and the porous diffusion layer 91B is 0.15 mm or less, like the examples 1 to 8. In the gas sensor according to the example 9, unlike the examples 2 to 8, the porous diffusion layer 91B is a porous layer having a porosity that is constant at 5% or more and 25% or less throughout; specifically, the porosity of the porous diffusion layer 91B is 25%. The surface (the external face facing the measurement target gas flow portion 7) of the porous diffusion layer 91B and the face on the electrode side (the internal face opposing the measurement electrode 44; the face facing the measurement electrode 44) both have a porosity of 25%, and the porosity difference therebetween is 0%. The gas sensor according to the example 9 has the leading end protection layer 200D ('with' in the table).

Unlike the examples 1 and 2, the leading end protection layer 200D includes the internal leading end protection layer 201. Specifically, the porosity (average porosity) of the leading end protection layer 200D is 15%, which is lower than the porosity (average porosity) of the porous diffusion layer 91B. That is, in the gas sensor according to the example 9, the porosity (25%) of the porous diffusion layer 91B is higher than the porosity (average porosity) (15%) of the leading end protection layer 200D, unlike the examples 1 to 3 and 5 to 8. However, the porosity of the internal leading end protection layer 201 included in the leading end protection layer 200D is 45%, which is higher than the porosity (25%) of the porous diffusion layer 91B. The shortest distance (d1) between the leading end protection layer 200D and the gas inlet 10, i.e. the distance d1 from the outermost face of the leading end protection layer 200D to the gas inlet 10 is 900 μm, namely 200 μm (0.2 mm) or more. The thickness of the external leading end protection layer 202 included in the leading end protection layer 200D is 300 μm, and the thickness of the internal leading end protection layer 201 included in the leading end protection layer 200D is 600 μm. Hence, the thickness proportion of the internal leading end protection layer 201, i.e. the proportion of the thickness of the internal leading end protection layer 201 to the thickness of the leading end protection layer 200D is 67%, namely 30% or more and 90% or less.

The example 10 is a gas sensor that includes the gas sensor element 101 that has the leading end protection layer 200 illustrated in FIG. 1 and the porous diffusion layer 91B illustrated in FIG. 6 (with different porosities between the surface and the face on the electrode side). Specifically, a space (gap) is present between the measurement electrode 44 and the porous diffusion layer 91B, and the distance d2 therebetween is 0.15 mm. Meanwhile, in the example 10, the distance d2 between the measurement electrode 44 and the porous diffusion layer 91B is 0.15 mm or less, like the examples 1 to 9. In the gas sensor according to the example 10, unlike the example 1, the porous diffusion layer 91B has different porosities between the surface (the external face facing the measurement target gas flow portion 7) and the face on the electrode side (the internal face opposing the measurement electrode 44; the face facing the measurement electrode 44). Specifically, in the gas sensor according to the example 10, the surface of the porous diffusion layer 91B has a porosity of 12%, and the face on the electrode side has a porosity of 10%. In other words, in the gas sensor of the example 10, the internal face of the porous diffusion layer 91B (the face on the electrode side) that opposes the measurement electrode 44 has a porosity (10%) lower than the porosity (12%) of the external face (surface), specifically by 2%, unlike the examples 3, 4, 5, and 7. The average porosity of the porous diffusion layer 91B is 10%, namely 5% or more and 25% or less. The gas sensor according to the example 10 has the leading end protection layer 200 ('with' in the table). Further, unlike the examples 3 to 7, the leading end protection layer 200 does not include the internal leading end protection layer 201, i.e. the porosity of the leading end protection layer 200 is constant throughout. Specifically, the porosity of the leading end protection layer 200 is 20%, which is higher than the porosity (average porosity) of the porous diffusion layer 91B. That is, in the gas sensor according to the example 10, the porosity (average porosity) (10%) of the porous diffusion layer 91B is lower than the porosity (20%) of the leading end protection layer 200. Further, the shortest distance (d1) between the leading end protection layer 200 and the gas inlet 10, i.e. the distance d1 from the outermost face of the leading end protection layer 200 to the gas inlet 10 is 300 μm, namely 200 μm (0.2 mm) or more. In the gas sensor according to the example 10, the leading end protection layer 200 does not include the internal leading end protection layer 201, as mentioned above. Thus, the thickness of the external leading end protection layer 202 is the same as the distance d1 from the outermost face of the leading end protection layer 200 to the gas inlet 10, namely 300 μm. The porosity of the internal leading end protection layer 201, the thickness of the internal leading end protection layer 201, and the thickness proportion of the internal leading end protection layer 201 are all ﹀_﹐ in the table.

The example 11 is a gas sensor that includes the gas sensor element 101 that has the leading end protection layer 200 illustrated in FIG. 1 and the porous diffusion layer 91B illustrated in FIG. 6 (with different porosities between the surface and the face on the electrode side). Specifically, a space (gap) is present between the measurement electrode 44 and the porous diffusion layer 91B, and the distance d2 therebetween is 0.1 mm. Meanwhile, in the example 11, the distance d2 between the measurement electrode 44 and the porous diffusion layer 91B is 0.15 mm or less, like the examples 1 to 10. In the gas sensor according to the example 11, unlike the example 1, the porous diffusion layer 91B has different porosities between the surface (the external face facing the measurement target gas flow portion 7) and the face on the electrode side (the internal face opposing the measurement electrode 44; the face facing the measurement electrode 44). Specifically, in the gas sensor according to the example 11, the porosity of the surface of the porous diffusion layer 91B is 7%, and the porosity of the face on the electrode side is 12%. In other words, in the gas sensor of the example 11, the internal face of the porous diffusion layer 91B (the face on the electrode side) that opposes the measurement electrode 44 has a porosity (12%) higher than the porosity (7%) of the external face (surface). Meanwhile, unlike the examples 3, 4, 5, and 7, the difference therebetween is less than 10% (specifically, 5%). The average porosity of the porous diffusion layer 91B is 10%, namely 5% or more and 25% or less. The gas sensor according to the example 11 has the leading end protection layer 200 ('with' in the table). Unlike the examples 3 to 7, the leading end protection layer 200 does not include the internal leading end protection layer 201; i.e. the porosity of the leading end protection layer 200 is constant throughout. Specifically, the porosity of the leading end protection layer 200 is 20%, which is higher than the porosity (average porosity) of the porous diffusion layer 91B. In other words, in the gas sensor according to the example 11, the porosity (average porosity) (10%) of the porous diffusion layer 91B is lower than the porosity (20%) of the leading end protection layer 200. In the gas sensor according to the example 11, the shortest distance (d1) between the leading end protection layer 200 and the gas inlet 10, i.e. the distance d1 from the outermost face of the leading end protection layer 200 to the gas inlet 10 is 100 μm. In other words, in the example 11, the distance d1 from the outermost face of the leading end protection layer 200 to the gas inlet 10 is less than 200 μm (0.2 mm), unlike the examples 1 to 10. In the gas sensor according to the example 11, the leading end protection layer 200 does not include the internal leading end protection layer 201, as mentioned above. Thus, the thickness of the external leading end protection layer 202 is the same as the distance d1 from the outermost face of the leading end protection layer 200 to the gas inlet 10, i.e. 100 μm. The porosity of the internal leading end protection layer 201, the thickness of the internal leading end protection layer 201, and the thickness proportion of the internal leading end protection layer 201 are all ﹀_﹐ in the table.

The example 12 is a gas sensor that includes the gas sensor element 101 that has the leading end protection layer 200 illustrated in FIG. 1 and the porous diffusion layer 91B illustrated in FIG. 6 (with different porosities between the surface and the face on the electrode side). Specifically, a space (gap) is present between the measurement electrode 44 and the porous diffusion layer 91B, and the distance d2 therebetween is 0.2 mm. In other words, in the example 12, the distance d2 from the porous diffusion layer 91B to the measurement electrode 44 is 0.2 mm, which is more than 0.15 mm, unlike the examples 1 to 11. In the gas sensor according to the example 12, unlike the example 1, the porous diffusion layer 91B has different porosities between the surface (the external face facing the measurement target gas flow portion 7) and the face on the electrode side (the internal face opposing the measurement electrode 44; the face facing the measurement electrode 44). Specifically, in the gas sensor according to the example 12, the porosity of the surface of the porous diffusion layer 91B is 12%, and the porosity of the face on the electrode side is 14%. In other words, in the gas sensor of the example 12, the internal face of the porous diffusion layer 91B (the face on the electrode side) that opposes the measurement electrode 44 has a porosity (14%) higher than the porosity (12%) of the external face (surface). Meanwhile, unlike the examples 3, 4, 5, and 7, the difference therebetween is less than 10% (specifically, 2%). The average porosity of the porous diffusion layer 91B is 15%, namely 5% or more and 25% or less. The gas sensor according to the example 12 has the leading end protection layer 200 ('with' in the table). Unlike the examples 3 to 7, the leading end protection layer 200 does not include the internal leading end protection layer 201; i.e. the porosity of the leading end protection layer 200 is constant throughout. Specifically, the porosity of the leading end protection layer 200 is 25%, which is higher than the porosity (average porosity) of the porous diffusion layer 91B. In other words, in the gas sensor according to the example 12, the porosity (average porosity) (15%) of the porous diffusion layer 91B is lower than the porosity (25%) of the leading end protection layer 200. The shortest distance (d1) between the leading end protection layer 200 and the gas inlet 10, i.e. the distance d1 from the outermost face of the leading end protection layer 200 to the gas inlet 10 is 300 μm, namely 200 μm (0.2 mm) or more. In the gas sensor according to the example 12, the leading end protection layer 200 does not include the internal leading end protection layer 201, as mentioned above. Thus, the thickness of the external leading end protection layer 202 is the same as the distance d1 from the outermost face of the leading end protection layer 200 to the gas inlet 10, i.e. 300 μm. The porosity of the internal leading end protection layer 201, the thickness of the internal leading end protection layer 201, and the thickness proportion of the internal leading end protection layer 201 are all '-' in the table.

The example 13 is a gas sensor that includes the gas sensor element 101 that has the leading end protection layer 200 illustrated in FIG. 1 and the porous diffusion layer 91A illustrated in FIG. 5. Specifically, in the example 13, no space (gap) is present between the measurement electrode 44 and the porous diffusion layer 91A, and the distance d2 therebetween is 0 mm, unlike the example 1. Meanwhile, in the example 13, the distance d2 between the measurement electrode 44 and the porous diffusion layer 91A is 0.15 mm or less, like the examples 1 to 11. In the gas sensor according to the example 13, the porous diffusion layer 91A has different porosities between the surface (the external face facing the measurement target gas flow portion 7) and the face on the electrode side (the internal face opposing the measurement electrode 44; the face facing (in contact with) the measurement electrode 44). Specifically, in the gas sensor according to the example 13, the porosity of the surface of the porous diffusion layer 91A is 15%, and the porosity of the face on the electrode side is 6%. In other words, in the gas sensor of the example 13, the internal face of the porous diffusion layer 91A (the face on the electrode side) that opposes the measurement electrode 44 has a porosity (6%) lower than the porosity (15%) of the external face (surface), unlike the examples 1 to 9, 11, and 12. Specifically, the internal face of the porous diffusion layer 91A that opposes the measurement electrode 44 has a porosity (6%) that is 9% lower than the porosity of the external face (15%). The average porosity of the porous diffusion layer 91A is 11%, namely 5% or more and 25% or less. The gas sensor according to the example 13 has the leading end protection layer 200 ('with' in the table). Unlike the examples 3 to 7, the leading end protection layer 200 does not include the internal leading end protection layer 201; i.e. the porosity of the leading end protection layer 200 is constant throughout. Specifically, the porosity of the leading end protection layer 200 is 25%, which is higher than the porosity (average porosity) of the porous diffusion layer 91A. In other words, in the gas sensor according to the example 13, the porosity (average porosity) (11%) of the porous diffusion layer 91A is lower than the porosity (25%) of the leading end protection layer 200. Further, the shortest distance (d1) between the leading end protection layer 200 and the gas inlet 10, i.e. the distance d1 from the outermost face of the leading end protection layer 200 to the gas inlet 10 is 280 μm, namely 200 μm (0.2 mm) or more. In the gas sensor according to the example 13, the leading end protection layer 200 does not include the internal leading end protection layer 201, as mentioned above. Thus, the thickness of the external leading end protection layer 202 is the same as the distance d1 from the outermost face of the leading end protection layer 200 to the gas inlet 10, i.e. 280 μm. The porosity of the internal leading end protection layer 201, the thickness of the internal leading end protection layer 201, and the thickness proportion of the internal leading end protection layer 201 are all ‹_› in the table.

The comparative example 1 is a gas sensor that includes a sensor element with the same structure as the example 2, except that the sensor element does not include the leading end protection layer 200. Specifically, in the comparative example 1, no space (gap) is present between the measurement electrode 44 and the porous diffusion layer 91A, and the distance d2 therebetween is 0 mm, unlike the example 1. Meanwhile, in the comparative example 1, the distance d2 between the measurement electrode 44 and the porous diffusion layer 91A is 0.15 mm or less, like the examples 1 to 11 and 13. In the gas sensor according to the comparative example 1, the porous diffusion layer 91A has different porosities between the surface (the external face facing the measurement target gas flow portion 7) and the face on the electrode side (the internal face opposing the measurement electrode 44; the face facing (in contact with) the measurement electrode 44). Specifically, in the gas sensor according to the comparative example 1, the porosity of the surface of the porous diffusion layer 91A is 6% and the porosity of the face on the electrode side is 12%. That is, in the gas sensor of the comparative example 1, the internal face (the face on the electrode side) of the porous diffusion layer 91A that opposes the measurement electrode 44 has a porosity (12%) higher than the porosity (6%) of the external face (surface). Meanwhile, unlike the examples 3 to 7, the difference therebetween is less than 10% (specifically, 6%), i.e. the internal face of the porous diffusion layer 91A that opposes the measurement electrode 44 has a porosity (12%) that is 6% higher than the porosity (6%) of the external face. The average porosity of the porous diffusion layer 91A is 10%, namely 5% or more and 25% or less. The gas sensor according to the comparative example 1 does not include the leading end protection layer 200 ('without' in the table) as mentioned above, and the porosity of the leading end protection layer 200 and the porosity of the internal leading end protection layer 201 are both ‹_› in the table. Also, the shortest distance between the leading end protection layer 200 and the gas inlet 10, the thickness of the external leading end protection layer 202, the thickness of the internal leading end protection layer 201, and the thickness proportion of the internal leading end protection layer 201 are all ‹_› in the table.

The comparative example 2 is a gas sensor that includes a sensor element that does not have a porous diffusion layer (the porous diffusion layer 91, 91A, or 91B) but has only the leading end protection layer 200 illustrated in FIG. 1. The comparative example 2 does not include the porous diffusion layer, and accordingly, the distance between the measurement electrode 44 and the porous diffusion layer, the average porosity of the porous diffusion layer, and the porosity of the surface of the porous diffusion layer (the external face facing the measurement target gas flow portion 7) are all ‹_› in the table. Also, the porosity of the face of the porous diffusion layer on the electrode side (the internal face opposing the measurement electrode 44; the face facing the measurement electrode 44) and the porosity difference (between the surface and the face of the measurement electrode 44 side) in the porous diffusion layer are all ‹_› in the table. The gas sensor according to the comparative example 2 has the leading end protection layer 200 ('with' in the table). However, unlike the examples 3 to 7, the leading end protection layer 200 does not include the internal leading end protection layer 201, i.e. the porosity of the leading end protection layer 200 is constant throughout. Specifically, the porosity of the leading end protection layer 200 is 15%. Further, the shortest distance (d1) between the leading end protection layer 200 and the gas inlet 10, i.e. the distance d1 from the outermost face of the leading end protection layer 200 to the gas inlet 10 is 250 μm, namely 200 μm (0.2 mm) or more. In the gas sensor according to the comparative example 2, the leading end protection layer 200 does not include the internal leading end protection layer 201, as mentioned above. Thus, the thickness of the external leading end protection layer 202 is the same as the distance d1 from the outermost face of the leading end protection layer 200 to the gas inlet 10, namely 250 μm. The porosity of the internal leading end protection layer 201, the thickness of the internal leading end protection layer 201, and the thickness proportion of the internal leading end protection layer 201 are all '-' in the table.

The comparative example 3 is a gas sensor that has the same structure as the example 2 and includes the gas sensor element 101 in which the average porosity of the porous diffusion layer 91A is larger (higher) than 25% and higher than the porosity of the leading end protection layer 200. Specifically, in the comparative example 3, no space (gap) is present between the measurement electrode 44 and the porous diffusion layer 91A, and the distance d2 therebetween is 0 mm, unlike the example 1. Meanwhile, in the comparative example 3, the distance d2 between the measurement electrode 44 and the porous diffusion layer 91A is 0.15 mm or less, like the examples 1 to 11 and 13. In the gas sensor according to the comparative example 3, the porous diffusion layer 91A has different porosities between the surface (the external face facing the measurement target gas flow portion 7) and the face on the electrode side (the internal face opposing the measurement electrode 44; the face facing (in contact with) the measurement electrode 44). Specifically, in the gas sensor according to the comparative example 3, the porosity of the surface of the porous diffusion layer 91A is 30%, and the porosity of the face on the electrode side is 40%. That is, in the gas sensor of the comparative example 3, the internal face (the face on the electrode side) of the porous diffusion layer 91A that opposes the measurement electrode 44 has a porosity (40%) higher than the porosity (30%) of the external face (surface), and the difference therebetween is 10 or more (specifically, 10%). Unlike the examples 1 to 3, 5 to 8, and 10 to 13, the average porosity of the porous diffusion layer 91A is 35% and is larger (higher) than 25%. The gas sensor according to the comparative example 3 has the leading end protection layer 200 ('with' in the table). Meanwhile, unlike the examples 3 to 7, the leading end protection layer 200 does not include the internal leading end protection layer 201, i.e. the porosity of the leading end protection layer 200 is constant throughout. Specifically, the porosity of the leading end protection layer 200 is 30%, which is lower than the porosity (average porosity) of the porous diffusion layer 91A. That is, in the gas sensor according to the comparative example 3, the porosity (average porosity) (35%) of the porous diffusion layer 91A is higher than the porosity (30%) of the leading end protection layer 200, unlike the examples 1 to 3, 5 to 8, and 10 to 13. Further, the shortest distance (d1) between the leading end protection layer 200 and the gas inlet 10, i.e. the distance d1 from the outermost face of the leading end protection layer 200 to the gas inlet 10 is 280 μm, namely 200 μm (0.2 mm) or more. In the gas sensor according to the comparative example 3, the leading end protection layer 200 does not include the internal leading end protection layer 201, as mentioned above. Thus, the thickness of the external leading end protection layer 202 is the same as the distance d1 from the outermost face of the leading end protection layer 200 to the gas inlet 10, namely 280 μm. The porosity of the internal leading end protection layer 201, the thickness of the internal leading end protection layer 201, and the thickness proportion of the internal leading end protection layer 201 are all '-' in the table.

Details of Evaluations 1 to 5

The evaluation 1 is for verifying the effect of suppressing the deterioration of the measurement electrode caused by high $H_2O$ concentration. Specifically, first, an environment with a $H_2O$ concentration=25% and an $O_2$ concentration=20.5% was prepared. A 2000-hour long-term durability test was conducted in this environment on the $NO_x$ sensors according to the examples 1 to 13 and the comparative examples 1 to 3. The inventors conducted the long-term durability test under the following accelerated deterioration test conditions in order to determine the degree of deterioration of properties (deterioration of the measurement electrode caused by high $H_2O$ concentration) in the case where the $NO_x$ sensors according to the examples 1 to 13 and the comparative examples 1 to 3 were continuously used for a long period of time. That is, the inventors conducted the long-term durability test under accelerated deterioration test conditions in which the heating temperature of the heat generating unit 72 was a predetermined temperature (100 degrees Celsius in the long-term durability test) higher than the sensor element drive temperature. The sensor element drive temperature is the heating temperature of the heat generating unit 72 when each $NO_x$ sensor is used (actually used), and can be considered as the heating temperature when the gas sensor element 101 is driven. An evaluation was conducted using a model gas to investigate the degree of change in $NO_x$ output when $NO_x$=500 ppm flowed, before and after the test. The symbol 'A' indicates that the $NO_x$ sensitivity change rate was within plus or minus 10%. The symbol 'B' indicates that the $NO_x$ sensitivity change rate was larger than plus or minus 10% and within 20%. The symbol 'F' indicates that the $NO_x$ sensitivity change rate was larger than plus or minus 20%.

The evaluation 2 is for verifying the effect of reducing $H_2O$ dependence and increasing the measurement accuracy while the $NO_x$ gas is flowing. Specifically, the following verification (investigation) was carried out. That is, after the test for the evaluation 1, the $NO_x$ concentration was changed to 500 ppm and the $H_2O$ concentration was changed 15%, with a $NO_x$ concentration=500 ppm and a $H_2O$ concentration=3% as a base, for the $NO_x$ sensors according to the examples 1 to 13 and the comparative examples 1 to 3. The degree of change in $NO_x$ output during the change was then investigated. The symbol 'A' indicates that the change rate (degree of change) in the $NO_x$ sensitivity from when $H_2O$ concentration=3% to when $H_2O$ concentration=15% was within plus or minus 5%. The symbol 'B' indicates that the change rate of the $NO_x$ sensitivity from when $H_2O$ concentration=3% to when $H_2O$ concentration=15% was within plus or minus 10%. The symbol 'F' indicates that the change rate of the $NO_x$ sensitivity from when $H_2O$ concentration=3% to when $H_2O$ concentration=15% was larger than plus or minus 10%.

The evaluation 3 is for verifying the effect of trapping a poisonous substance and preventing clogging around the measurement electrode (e.g. the porous diffusion layer) that is achieved by the leading end protection layer, and the following Mg poisoning test was conducted on the $NO_x$ sensors according to the examples 1 to 13 and the comparative examples 1 to 3. That is, a cycle of dropping 10 μL of Mg ion solution with a Mg ion concentration of 5 mmol/L onto the $NO_x$ sensors, leaving these $NO_x$ sensors to stand for 1 minute, and then driving each gas sensor at 800 degrees Celsius for 10 minutes was repeated 10 times. Thus, a total of 100 μL of the Mg ion solution was dropped. The degree of change (change rate) in $NO_x$ output before and after the test was then investigated. Specifically, first, the $NO_x$ sensitivity was measured in a $NO_x$ model gas with a $NO_x$ concentration=500 ppm using each of the $NO_x$ sensors according to the examples 1 to 13 and the comparative examples 1 to 3, and the measured sensitivity was used as an initial $NO_x$ sensitivity. Then, a cycle of dropping 10 μL of the aforementioned Mg ion solution into the gas inlet of each $NO_x$ sensor, leaving the $NO_x$ gas sensor to stand for 1 minute, and then driving the gas sensor at 800 degrees Celsius for 10 minutes was repeated 10 times. Thus, a total of 100 μL of the Mg ion solution was dropped. Then, the $NO_x$ sensitivity was measured again in the aforementioned $NO_x$ model gas using each $NO_x$ sensor, and a sensitivity decrease rate was calculated by comparing the measured $NO_x$ sensitivity with the initial $NO_x$ sensitivity. The symbol 'A' indicates that the $NO_x$ sensitivity change rate was within plus or minus 10%. The symbol 'B' indicates that the $NO_x$ sensitivity change rate was larger than plus or minus 20% and within 30%. The symbol 'F' indicates that the $NO_x$ sensitivity change rate was larger than 30%.

The evaluation 4 is, like the evaluation 3, for verifying the effect of reducing clogging around the measurement electrode that is achieved by the leading end protection layer, while the effect is verified under more severe conditions than with the method used in the evaluation 3. Specifically, the likelihood of clogging in the leading end protection layer was increased. That is, in the evaluation 4, the same Mg poisoning test as in the evaluation 3 was conducted, except that the total amount of Mg ion solution dropped was 500 μL. The degree of change (change rate) in $NO_x$ output before and after the test was then investigated, i.e. the degree of change in $NO_x$ output when $NO_x$ model gas with a $NO_x$ concentration=500 ppm flowed was investigated. The symbol 'A' indicates that the $NO_x$ sensitivity change rate was within plus or minus 10%. The symbol 'B' indicates that the $NO_x$ sensitivity change rate was larger than plus or minus 20% and within 30%. The symbol 'F' indicates that the $NO_x$ sensitivity change rate was larger than plus or minus 30%.

The evaluation 5 is for verifying (measuring) the light-off time (the time required from when the $NO_x$ sensor starts until when the $NO_x$ sensor enters the steady operation state). Specifically, a mixed gas environment was produced where a $NO_x$ concentration=100 ppm, a $H_2O$ concentration=9%, and the remainder was N2, and the light-off time was measured with the $NO_x$ sensors according to the examples 1 to 13 and the comparative examples 1 to 3 each attached to a chamber and the aforementioned mixed gas flowing through the chamber. The light-off time was obtained as a time with which the $NO_x$ concentration value fell within the range of 90 ppm to 110 ppm, after a current began to flow through the gas sensor element. The symbol 'A' indicates that the light-off time was within 100 seconds. The symbol 'B' indicates that the light-off time was more than 100 seconds and within 130 seconds. The symbol 'C' indicates that the light-off time was more than 130 seconds and within 200 seconds.

Summary of Facts Confirmed from Table 1

The following is a summary of the facts that can be confirmed from Table 1 that shows the test results of the evaluations 1 to 5 for the gas sensors that include the sensor elements according to the examples 1 to 13 and the comparative examples 1 to 3.

As indicated by the results of comparing the examples 1 to 13 with the comparative example 1 in the evaluation 3, the gas sensor can achieve the following effects as a result of including the leading end protection layer 200 (or the leading end protection layer 200D). That is, the results (A or B) of the evaluation 3 for the examples 1 to 13 with the leading end protection layer 200 or the leading end protection layer 200D are all better than the result (F) of the evaluation 3 for the comparative example 1 without the leading end protection layer 200 or the leading end protection layer 200D. Accordingly, it was confirmed that the gas sensor can trap poisonous substances and prevent clogging around the measurement electrode 44 (e.g. the porous diffusion layer 91) as a result of including the leading end protection layer 200 (or the leading end protection layer 200D).

As indicated by the results of comparing the examples 1 to 13 with the comparative example 2 in the evaluation 1 and the evaluation 2, it was confirmed that the gas sensor can achieve the following effects as a result of including the porous diffusion layer (e.g. the porous diffusion layer 91) that makes the diffusion mode around the measurement electrode 44 favorable. That is, the results (A or B) of the evaluation 1 for the examples 1 to 13 with the porous diffusion layer 91 or the like are better than the result (F) of the evaluation 1 for the comparative example 2 without the porous diffusion layer 91 or the like. Accordingly, it was confirmed that the gas sensor can suppress the deterioration of the measurement electrode (particularly, deterioration of the measurement electrode caused by high $H_2O$ concentration) as a result of including the porous diffusion layer (e.g. the porous diffusion layer 91) that makes the diffusion mode around the measurement electrode 44 favorable (evaluation 1). Further, the results (A or B) of the evaluation 2 for the examples 1 to 13 with the porous diffusion layer 91 or the like are all better than the result (F) of the evaluation 2 for the comparative example 2 without the porous diffusion layer 91 or the like. Accordingly, it was confirmed that the gas sensor can reduce $H_2O$ dependence of $NO_x$ sensitivity ($NO_x$ output) and increase the measurement accuracy (evaluation 2) as a result of including the porous diffusion layer (e.g. the porous diffusion layer 91) that makes the diffusion mode around the measurement electrode 44 favorable.

The results of the evaluations 1 and 2 significantly differ between the example 2 and the comparative example 3, depending on whether or not the porosity of the porous diffusion layer 91A, which covers the measurement electrode 44 in contact therewith, is 5% or more and 25% or less and is lower than the porosity of the leading end protection layer. Specifically, the results of the evaluations 1 and 2 for the example 2, which includes the porous diffusion layer 91A having a porosity that is 5% or more and 25% or less and is lower than the porosity of the leading end protection layer, are both A. In contrast, the results of the evaluations 1 and 2 for the comparative example 3, which includes the porous diffusion layer 91A having a porosity that is larger than 25% and higher than the porosity of the leading end protection layer, are both F. Accordingly, it was confirmed that the gas sensor can achieve the following effects as a result of the porosity of the porous diffusion layer 91A being 5% or more and 25% or less and being lower than the porosity of the leading end protection layer. That is, it was confirmed that the gas sensor suppressed the deterioration of the measurement electrode that is caused by high $H_2O$ concentration, as a result of the porosity of the porous diffusion layer 91A being 5% or more and 25% or less and being lower than the porosity of the leading end protection layer (evaluation 1). It was also confirmed that the gas sensor reduced the $H_2O$ dependence of $NO_x$ sensitivity ($NO_x$ output) and increased the measurement accuracy as a result of the porosity of the porous diffusion layer 91A being 5% or more and 25% or less and being lower than the porosity of the leading end protection layer (evaluation 2).

Note that in the examples 4 and 9, the porosity (average porosity) of the porous diffusion layers 91A and 91B is 5% or more and 25% or less, but is higher than the porosity (average porosity) of the leading end protection layer 200D, unlike the examples 1 to 3, 5 to 8, and 10 to 13. Meanwhile, in the examples 4 and 9, the porosity (average porosity) of the porous diffusion layers 91A and 91B is lower than the porosity of the internal leading end protection layer 201, i.e. is lower than the porosity of the internal leading end protection layer 201 that is in contact with the face of the element substrate 100 in which the gas inlet 10 is open. The result of the evaluation 2 for the example 4 is A, and the result of the evaluation 2 for the example 9 is B. In contrast, in the comparative example 3, the leading end protection layer 200 does not include the internal leading end protection layer 201, and the porosity of the porous diffusion layer 91 is larger than 25% and higher than the porosity of the leading end protection layer 200. The result of the evaluation 2 for the comparative example 3 is F. Therefore, it can be considered that the following effects can be achieved as a result of the porosity of the porous diffusion layers 91A and 91B being 5% or more and 25% or less and being at least lower than the porosity of the internal leading end protection layer 201 that is in contact with the face of the element substrate 100 in which the gas inlet 10 is open. In other words, it can be considered that $H_2O$ dependence of the $NO_x$ sensitivity ($NO_x$ output) can be reduced, and the measurement accuracy can be increased.

The examples 2 and 13 have the same configuration, except for whether or not the porosity of the internal face (the face on the electrode side) opposing the measurement electrode 44, of the two faces of the porous diffusion layer 91A in the thickness direction, is higher than the porosity of the external face (surface). The result of the evaluation 5 for the example 2 is 'B', while the result of the evaluation 5 for the example 13 is 'C'. Thus, it was confirmed that making the porosity of the internal face of the porous diffusion layer 91A that opposes the measurement electrode 44 higher than the porosity of the external face enables the gas sensor to achieve the following effects. That is, it was confirmed that the light-off time of the gas sensor can be shortened by making the porosity of the internal face of the porous diffusion layer 91A that opposes the measurement electrode 44 higher than the porosity of the external face (evaluation 5).

The examples 8 and 12 have the same configuration, except for whether or not the distance d2 from the porous diffusion layer 91B to the measurement electrode 44 is 0.15 mm or less. The results of the evaluations 1 and 2 for the example 8 are both 'A', while the results of the evaluations 1 and 2 for the example 12 are both 'B'. Thus, it was confirmed that setting the distance d2 from the porous diffusion layer 91B to the measurement electrode 44 to 0.15 mm or less enables the gas sensor to achieve the following effects. Specifically, it was confirmed that setting the distance d2 from the porous diffusion layer 91B to the measurement electrode 44 to 0.15 mm or less enables the gas sensor to suppress the deterioration of the measurement electrode due to high $H_2O$ concentration (evaluation 1). It was also confirmed that setting the distance d2 from the porous diffusion layer 91B to the measurement electrode 44 to 0.15 mm or less enables the gas sensor to reduce $H_2O$ dependence of $NO_x$ sensitivity ($NO_x$ output) and increase the measurement accuracy (evaluation 2).

The examples 5 and 6 have the same configuration, except for whether or not the internal face (the face on the electrode side) opposing the measurement electrode 44, of the two faces of the porous diffusion layer 91A in the thickness direction, is 10% or more higher than the porosity of the external face (surface). The result of the evaluation 5 for the example 5 is 'A', while the result of the evaluation 5 for the example 6 is 'B'. Thus, it was confirmed that making the porosity of the internal face of the porous diffusion layer 91A that opposed the measurement electrode 44 10% or more higher than the porosity of the external face enables the gas sensor to achieve the following effects. That is, it was confirmed that the light-off time of the gas sensor can be shortened by making the porosity of the internal face of the porous diffusion layer 91A that opposes the measurement electrode 44 10% or more higher than the porosity of the external face (evaluation 5).

The examples 8 and 11 have the same configuration, except for whether or not the distance d1 from the outermost face of the leading end protection layer 200 to the gas inlet 10 is 0.2 mm (200 μm) or more. The result of the evaluation 4 for the example 8 is 'B', while the result of the evaluation 4 for the example 11 is 'F'. Thus, it was confirmed that setting the distance d1 from the outermost face of the leading end protection layer 200 to the gas inlet 10 to 0.2 mm or more enables the gas sensor to achieve the following effects. Specifically, it was confirmed that setting the distance d1 to 0.2 mm or more enables the gas sensor to trap poisonous substances and prevent clogging around the measurement electrode, even in a harsh environment with a large amount of poisonous substances or the like that could cause clogging in the leading end protection layer itself (evaluation 4).

The examples 2 and 6 have the same structure, except for whether the gas sensor includes the leading end protection layer 200 or the leading end protection layer 200D that includes the internal leading end protection layer 201 and the external leading end protection layer 202. That is, the example 6 has the leading end protection layer 200D, the porosity of the internal leading end protection layer 201 is larger than the porosity of the external leading end protection layer 202, and the thickness of the internal leading end protection layer 201 is 30% or more and 90% or less of the thickness of the leading end protection layer 200D. The result of the evaluation 4 for the example 2 is 'B', while the result of the evaluation 4 for the example 6 is 'A'. Thus, it was confirmed that the gas sensor can achieve at least the following effects related to the evaluation 4, as a result of including the leading end protection layer 200D, with the thickness of the internal leading end protection layer 201 being 30% or more and 90% or less of the thickness of the leading end protection layer 200D. Specifically, it was confirmed that including the leading end protection layer 200D having the above-described configuration enables the gas sensor to trap poisonous substances and prevent clogging around the measurement electrode, even in a harsh environment with a large amount of poisonous substances or the like that could cause clogging in the leading end protection layer itself (evaluation 4).

$NO_x$ Sensitivity Change Rate

Figure 9:
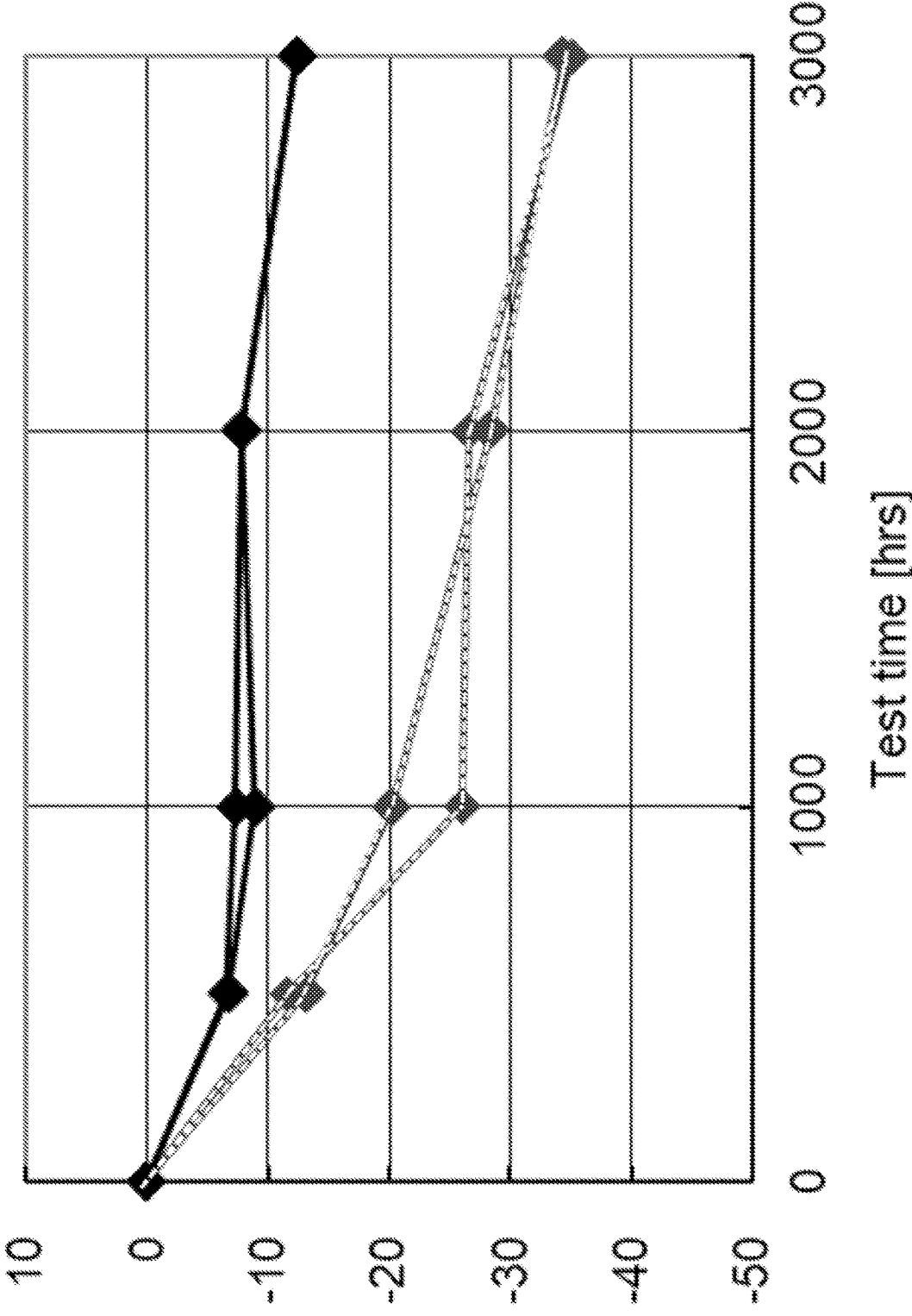
FIG. 9 is a graph showing differences in change in $NO_x$ output over time with and without a porous diffusion layer covering a measurement electrode.

FIG. 9 is a graph showing differences in the change over time in $NO_x$ output with and without the porous diffusion layer covering the measurement electrode. Specifically, FIG. 9 shows the change over time in $NO_x$ output of each $NO_x$ sensor under high $H_2O$ concentration (e.g. $H_2O$ concentration=25%) regarding $NO_x$ sensors with the same structure, except for the presence of the porous diffusion layer (any of the porous diffusion layers 91, 91A, and 91B) that covers the measurement electrode 44. In the graph in FIG. 9, the horizontal axis indicates time (drive time), and the vertical axis indicates the $NO_x$ sensitivity change rate. Solid black lines indicate the change over time in $NO_x$ output of the $NO_x$ sensors that include the porous diffusion layer that covers the measurement electrode 44. Dotted lines indicate the change over time in $NO_x$ output of the $NO_x$ sensors that do not include the porous diffusion layer that covers the measurement electrode 44 (specifically, conventional $NO_x$ sensors that merely have a slit structure using a diffusion control portion).

Specifically, an $NO_x$ current (pump current Ip2) was measured for the aforementioned $NO_x$ sensors in a model gas atmosphere with a $NO_x$ concentration=500 ppm and the remainder being nitrogen, using a model gas apparatus. The graph shown in FIG. 9 was created by plotting the $NO_x$ sensitivity ($NO_x$ sensitivity change rate) calculated from the measurement results at each driving time.

As shown in FIG. 9, the $NO_x$ sensitivity significantly varies during the long-term drive test under high $H_2O$ concentration in the $NO_x$ sensors that do not have the porous diffusion layer around the measurement electrode 44 (conventional $NO_x$ sensors that merely have a slit structure using a diffusion control portion). This is possibly because molecular diffusion is a dominant diffusion mode around the measurement electrode 44 in the conventional slit structure using a diffusion control portion. In contrast, the $NO_x$ sensors that include the porous diffusion layer can suppress fluctuations (change over time) in the $NO_x$ sensitivity even under high $H_2O$ concentration by making the diffusion mode around the measurement electrode 44 a favorable diffusion mode, such as Knudsen diffusion.

$H_2O$ Dependence of $NO_x$ Output

Figure 10:
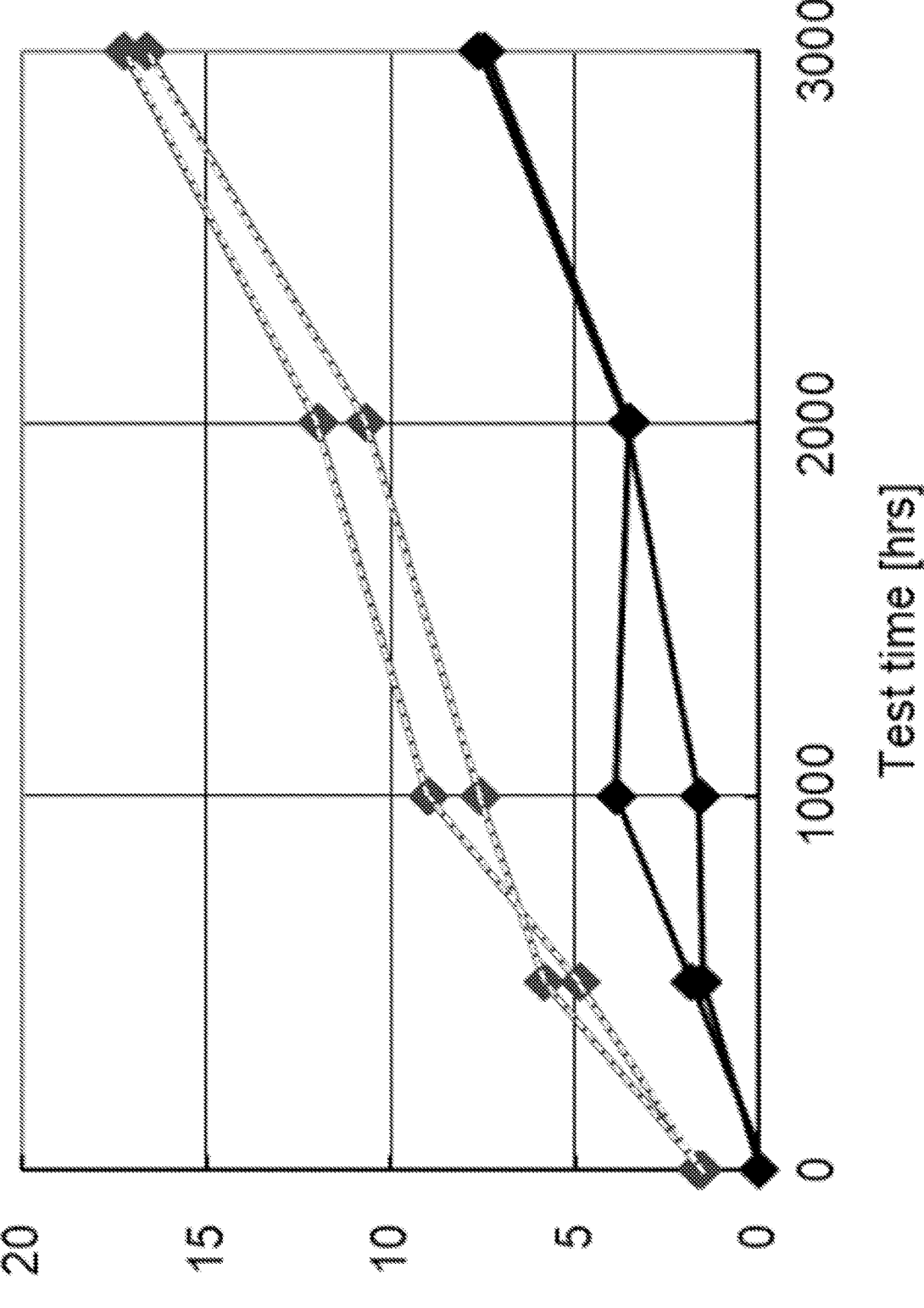
FIG. 10 is a graph showing differences in $H_2O$ dependence of $NO_x$ output with and without the porous diffusion layer covering the measurement electrode.
Figure 11:
FIG. 11 shows an example of molecular diffusion.
Figure 12:
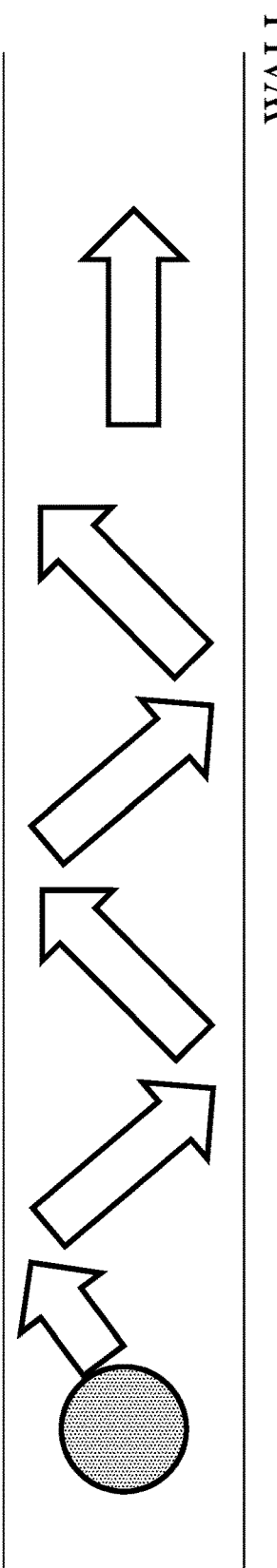
FIG. 12 shows an example of Knudsen diffusion.

FIG. 10 is a graph showing differences in $H_2O$ dependence of the $NO_x$ output with and without the porous diffusion layer covering the measurement electrode. Specifically, FIG. 10 shows differences in $H_2O$ dependence of the $NO_x$ output for the $NO_x$ sensors with the same structure, except for the presence of the porous diffusion layer (any of the porous diffusion layers 91, 91A, and 91B) that covers the measurement electrode 44. In the graph in FIG. 10, the horizontal axis indicates time (drive time), and the vertical axis indicates $H_2O$ dependence of $NO_x$ sensitivity. Solid black lines indicate the change over time in $H_2O$ dependence of the $NO_x$ output of the $NO_x$ sensors that include the porous diffusion layer that covers the measurement electrode 44. Dotted lines indicate the change over time in $H_2O$ dependence of $NO_x$ output of the $NO_x$ sensors that do not include the porous diffusion layer that covers the measurement electrode 44 (specifically, conventional $NO_x$ sensors that merely have a slit structure using a diffusion control portion).

The $H_2O$ dependence of $NO_x$ output was obtained based on the degree of change (change rate) in the $NO_x$ current (pump current Ip2) measured under the following conditions. That is, the $H_2O$ dependence of $NO_x$ output was calculated based on the change rate of the $NO_x$ current when $NO_x$ concentration=500 ppm and a $H_2O$ concentration=15%, with a $NO_x$ concentration=500 ppm and a $H_2O$ concentration=3% as a base. The graph shown in FIG. 10 was created by plotting the $H_2O$ dependence of $NO_x$ output (change rate of the $NO_x$ current) at each drive time.

As shown in FIG. 10, the $H_2O$ dependence of $NO_x$ output significantly varies during the long-term drive test under high $H_2O$ concentration with the $NO_x$ sensors that do not include the porous diffusion layer around the measurement electrode 44 (conventional the $NO_x$ sensors that merely have a slit structure using a diffusion control portion). This is possibly because molecular diffusion is a dominant diffusion mode around the measurement electrode 44 in the conventional slit structure using a diffusion control portion. In contrast, the $NO_x$ sensors that include the porous diffusion layer make the diffusion mode around the measurement electrode 44 a mode of diffusing while repeatedly colliding with a wall face of a sufficiently narrow flow path, as in Knudsen diffusion, thus reducing the $H_2O$ dependence of $NO_x$ output, even under high $H_2O$ concentration. Further, the $NO_x$ sensors that include the porous diffusion layer can suppress fluctuations (change over time) in the $H_2O$ dependence of $NO_x$ output even under high $H_2O$ concentration by making the diffusion mode around the measurement electrode 44 a favorable mode, such as Knudsen diffusion.

Facts Confirmed Through Verifications

Some of the above-described test results (verification results) shown in Table 1 and FIGS. 9 and 10 can also be summarized as follows. That is, the $NO_x$ sensitivity and the $NO_x$ output relative to high $H_2O$ concentration significantly vary in the long-term drive test under high $H_2O$ concentration with the gas sensors (conventional $NO_x$ sensors) that do not include the porous diffusion layer around the measurement electrode 44 and merely have the slit structure using a diffusion control portion. This is possibly because molecular diffusion is a dominant diffusion mode around the measurement electrode 44 in the conventional slit structure using the diffusion control portion.

The porous diffusion layer (e.g. the porous diffusion layer 91) having a porosity that is 5% or more and 25% or less covers the measurement electrode 44, and particularly, the distance d2 from the porous diffusion layer to the measurement electrode 44 was made sufficiently small (specifically, 0.15 mm or less). The following effects were confirmed with the gas sensors that adopted this configuration. That is, these gas sensors can suppress fluctuations in $NO_x$ sensitivity. This is possibly because, when Knudsen diffusion is dominant around the measurement electrode 44, the ease of diffusion of $NO_x$ and $O_2$ gases is less likely to change even in the presence of $H_2O$ gas, which has a smaller molecular weight, and the increase in $NO_x$ and $O_2$ gases that reach the measurement electrode 44 is also smaller.

As indicated by the results in Table 1, it is preferable that the shortest distance (distance d1) from the outermost face of the leading end protection layer (200, 200D) to the gas inlet 10 is 0.2 mm or more. The gas sensor can prevent clogging in the vicinity of the gas inlet 10 and prevent a decrease in $NO_x$ sensitivity even if the gas sensor is exposed to a harsh environment with a large amount of a clogging material (e.g. poisonous substance), due to a large distance d1 from the outermost face of the leading end protection layer to the gas inlet 10. That is, the gas sensor can prevent clogging in the vicinity of the gas inlet 10 and prevent a decrease in $NO_x$ sensitivity even if the gas sensor is exposed to a harsh environment with a large amount of poisonous substances or the like, as a result of the distance d1 from the outermost face of the leading end protection layer to the gas inlet 10 being 0.2 mm or more.

Furthermore, it is desirable that the leading end protection layer includes at least two layers, and the internal layer (the internal leading end protection layer 201) has a porosity larger (higher) than the porosity of the external layer (the external leading end protection layer 202). Particularly, it is desirable in the leading end protection layer that the proportion of the thickness of the internal layer to the thickness of the entire leading end protection layer is 30% or more and 90% or less. The likelihood that a layer closer to the gas inlet 10 (i.e. internal layer) will be clogged with poisonous substances or the like can be reduced as a result of the proportion of the thickness of the internal layer, which has a porosity larger than the porosity of the external layer, to the thickness of the entire leading end protection layer being larger than that of the external layer.

LIST OF REFERENCE NUMERALS

100, 100C Element substrate
101 Gas sensor element
10 Gas inlet
7, 7C Measurement target gas flow portion (internal space)
44 Measurement electrode
18 Fourth diffusion control portion (diffusion control portion)
91, 91A, 91B Porous diffusion layer
19 Third internal cavity (internal cavity)
911 First porous diffusion layer (external face)

912 Second porous diffusion layer (internal face opposing measurement electrode)
200, 200D Leading end protection layer
201 Internal leading end protection layer
202 External leading end protection layer

What is claimed is:

1. A gas sensor element comprising:
an element substrate having a surface in which a gas inlet is open, and including an internal space into which a measurement target gas is introduced from the gas inlet;
a leading end protection layer covering at least a face of the element substrate in which the gas inlet is open;
a measurement electrode provided in the internal space and containing at least either silica or alumina; and
a porous diffusion layer covering the measurement electrode and having a porosity that is 5% or more and 25% or less and is lower than a porosity of the leading end protection layer,
wherein the porous diffusion layer has two faces in a thickness direction that are an internal face opposing the measurement electrode and an external face, and the internal face has a porosity higher than a porosity of the external face.

2. The gas sensor element according to claim 1, further comprising:
a diffusion control portion configured to apply a predetermined diffusion resistance to the measurement target gas in the internal space,
wherein the measurement electrode is disposed in an internal cavity that is demarcated by the diffusion control portion on an upstream side in a flow direction of the measurement target gas.

3. The gas sensor element according to claim 1,
wherein a distance from an outermost face of the leading end protection layer to the gas inlet is 0.2 mm or more.

4. The gas sensor element according to claim 1,
wherein the leading end protection layer includes at least:
an internal leading end protection layer in contact with the face of the element substrate in which the gas inlet is open; and
an external leading end protection layer constituting an outermost face of the leading end protection layer,
wherein the internal leading end protection layer has a porosity larger than a porosity of the external leading end protection layer, and
wherein the internal leading end protection layer has a thickness that is 30% or more and 90% or less of a thickness of the leading end protection layer.

5. A gas sensor comprising the gas sensor element according to claim 1 and configured to measure an amount of a specific gas component in the measurement target gas.

6. The gas sensor element according to claim 1,
wherein the measurement electrode and the porous diffusion layer are not in contact with each other, and
wherein a distance between the measurement electrode and the porous diffusion layer is 0.15 mm or less.

7. The gas sensor element according to claim 1,
wherein the porous diffusion layer has two faces in a thickness direction that are an internal face opposing the measurement electrode and an external face, and the internal face has a porosity that is at least 10% higher than a porosity of the external face.

8. A gas sensor element comprising:
an element substrate having a surface in which a gas inlet is open, and including an internal space into which a measurement target gas is introduced from the gas inlet;
a leading end protection layer covering at least a face of the element substrate in which the gas inlet is open;
a measurement electrode provided in the internal space and containing at least either silica or alumina; and
a porous diffusion layer covering the measurement electrode and having a porosity that is 5% or more and 25% or less and is lower than a porosity of the leading end protection layer,
wherein the measurement electrode and the porous diffusion layer are not in contact with each other, and
wherein a distance between the measurement electrode and the porous diffusion layer is 0.15 mm or less.

9. The gas sensor element according to claim 8, further comprising:
a diffusion control portion configured to apply a predetermined diffusion resistance to the measurement target gas in the internal space,
wherein the measurement electrode is disposed in an internal cavity that is demarcated by the diffusion control portion on an upstream side in a flow direction of the measurement target gas.

10. The gas sensor element according to claim 8,
wherein a distance from an outermost face of the leading end protection layer to the gas inlet is 0.2 mm or more.

11. The gas sensor element according to claim 8,
wherein the leading end protection layer includes at least:
an internal leading end protection layer in contact with the face of the element substrate in which the gas inlet is open; and
an external leading end protection layer constituting an outermost face of the leading end protection layer,
wherein the internal leading end protection layer has a porosity larger than a porosity of the external leading end protection layer, and
wherein the internal leading end protection layer has a thickness that is 30% or more and 90% or less of a thickness of the leading end protection layer.

12. A gas sensor comprising the gas sensor element according to claim 8 and configured to measure an amount of a specific gas component in the measurement target gas.

13. The gas sensor element according to claim 8,
wherein the porous diffusion layer has two faces in a thickness direction that are an internal face opposing the measurement electrode and an external face, and the internal face has a porosity that is at least 10% higher than a porosity of the external face.

14. A gas sensor element comprising:
an element substrate having a surface in which a gas inlet is open, and including an internal space into which a measurement target gas is introduced from the gas inlet;
a leading end protection layer covering at least a face of the element substrate in which the gas inlet is open;
a measurement electrode provided in the internal space and containing at least either silica or alumina; and
a porous diffusion layer covering the measurement electrode and having a porosity that is 5% or more and 25% or less and is lower than a porosity of the leading end protection layer,
wherein the porous diffusion layer has two faces in a thickness direction that are an internal face opposing the measurement electrode and an external face, and the internal face has a porosity that is at least 10% higher than a porosity of the external face.

15. The gas sensor element according to claim 14, further comprising:

a diffusion control portion configured to apply a predetermined diffusion resistance to the measurement target gas in the internal space, wherein the measurement electrode is disposed in an internal cavity that is demarcated by the diffusion control portion on an upstream side in a flow direction of the measurement target gas.

16. The gas sensor element according to claim 14, wherein the measurement electrode and the porous diffusion layer are not in contact with each other, and wherein a distance between the measurement electrode and the porous diffusion layer is 0.15 mm or less.

17. The gas sensor element according to claim 14, wherein a distance from an outermost face of the leading end protection layer to the gas inlet is 0.2 mm or more.

18. The gas sensor element according to claim 14, wherein the leading end protection layer includes at least:

an internal leading end protection layer in contact with the face of the element substrate in which the gas inlet is open; and an external leading end protection layer constituting an outermost face of the leading end protection layer, wherein the internal leading end protection layer has a porosity larger than a porosity of the external leading end protection layer, and wherein the internal leading end protection layer has a thickness that is 30% or more and 90% or less of a thickness of the leading end protection layer.

19. A gas sensor comprising the gas sensor element according to claim 14 and configured to measure an amount of a specific gas component in the measurement target gas.

* * * * *